US011857555B2

(12) United States Patent
Chen et al.

(10) Patent No.: US 11,857,555 B2
(45) Date of Patent: *Jan. 2, 2024

(54) AQUEOUS PHARMACEUTICAL FORMULATION OF HYDROCORTISONE SODIUM PHOSPHATE AND MONOTHIOGLYCEROL

(71) Applicant: ANTARES PHARMA, INC., Ewing, NJ (US)

(72) Inventors: Xiaoming Chen, Westfield, NJ (US); Shaowei Ong, Belle Mead, NJ (US)

(73) Assignee: ANTARES PHARMA, INC., Ewing, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/056,997

(22) Filed: Nov. 18, 2022

(65) Prior Publication Data

US 2023/0099165 A1 Mar. 30, 2023

Related U.S. Application Data

(63) Continuation of application No. 17/494,340, filed on Oct. 5, 2021, which is a continuation of application No. PCT/US2021/051349, filed on Sep. 21, 2021.

(60) Provisional application No. 63/081,164, filed on Sep. 21, 2020.

(51) Int. Cl.
| | |
|---|---|
| *A61K 31/573* | (2006.01) |
| *A61K 47/18* | (2017.01) |
| *A61K 47/02* | (2006.01) |
| *A61K 47/20* | (2006.01) |
| *A61K 9/08* | (2006.01) |

(52) U.S. Cl.
CPC .............. *A61K 31/573* (2013.01); *A61K 9/08* (2013.01); *A61K 47/02* (2013.01); *A61K 47/183* (2013.01); *A61K 47/20* (2013.01)

(58) Field of Classification Search
CPC ...... A61K 31/573; A61K 47/20; A61K 47/02; A61K 47/183
See application file for complete search history.

(56) References Cited

U.S. PATENT DOCUMENTS

| | | | |
|---|---|---|---|
| 2,970,944 A | 2/1961 | Charnicki et al. | |
| 3,696,195 A * | 10/1972 | Crivellaro | .............. A61K 31/66 514/973 |
| 5,173,488 A | 12/1992 | Haeger | |
| 5,733,572 A | 3/1998 | Unger | |
| 6,028,066 A | 2/2000 | Unger | |
| 8,021,335 B2 | 9/2011 | Lesch, Jr. | |

(Continued)

FOREIGN PATENT DOCUMENTS

| | | |
|---|---|---|
| EP | 3189855 B1 | 3/2018 |
| WO | 2018078285 A1 | 5/2018 |

(Continued)

OTHER PUBLICATIONS

Efcortesol hydrocortisone sodium phosphate injection, Patient Information Leaflet, 102451-52/LF/057/03, Amdipharm, 1 page.

(Continued)

*Primary Examiner* — Timothy P Thomas
(74) *Attorney, Agent, or Firm* — Morgan, Lewis & Bockius LLP

(57) ABSTRACT

Aqueous hydrocortisone sodium phosphate and monothioglycerol formulations are disclosed.

14 Claims, 13 Drawing Sheets

(56) References Cited

U.S. PATENT DOCUMENTS

| | | |
|---|---|---|
| 8,814,834 B2 | 8/2014 | Sund et al. |
| 8,945,063 B2 | 2/2015 | Wotton et al. |
| 10,300,207 B2 | 5/2019 | Newton et al. |
| 10,456,355 B1 * | 10/2019 | Bardonnaud ............ A61P 11/06 |
| 10,653,839 B2 | 5/2020 | Vigot |
| 2001/0018072 A1 | 8/2001 | Unger |
| 2007/0105761 A1 | 5/2007 | Chappell |
| 2020/0255462 A1 | 8/2020 | Siddiqui-Jain et al. |

FOREIGN PATENT DOCUMENTS

| | | | | |
|---|---|---|---|---|
| WO | WO-2018078285 A1 * | 5/2018 | ............ | A61K 31/10 |
| WO | 2019213662 A1 | 11/2019 | | |

OTHER PUBLICATIONS

"How to give an emergency injection of Efcortesol" Information for families, Great Ormond Street Hospital for Children NHS Foundation Trust University College London Hospitals NHS Trust, 4 pages.

Solu-Cortef label (hydrocortisone sodium succinate for injection, USP; Apr. 2010; Pharmacia & Upjohn Company division of Pfizer, Inc. (2010), 15 pages.

International Search Report and Written Opinion issued in PCT/US2021/051349, dated Jan. 20, 2022, 15 pages.

International Search Report and Written Opinion for PCT/US2023/064771, dated Jul. 5, 2023, 14 pages.

\* cited by examiner

AQUEOUS PHARMACEUTICAL FORMULATION OF HYDROCORTISONE SODIUM PHOSPHATE AND MONOTHIOGLYCEROL

CROSS-REFERENCE TO RELATED APPLICATION

This application is a continuation of U.S. patent application Ser. No. 17/494,340 filed Oct. 5, 2021, which is a continuation of International Patent Application No. PCT/US2021/051349 filed Sep. 21, 2021, which claims the benefit of U.S. Provisional Patent Application No. 63/081,164, filed Sep. 21, 2020, each of which is incorporated by reference herein in its entirety.

FIELD

The invention relates generally to hydrocortisone and hydrocortisone prodrugs, and pharmaceutically acceptable salts thereof, and related formulations.

BACKGROUND

Hydrocortisone is the name for the hormone cortisol when supplied as a medication. It is used in oral administration, intravenous injection, or topical application. It is used as an immunosuppressive drug, given by injection in the treatment of severe allergic reactions such as anaphylaxis and angioedema. It may be used topically for allergic rashes, eczema, psoriasis, itching and other inflammatory skin conditions.

Therapeutic hydrocortisone is a synthetic or semisynthetic analog of natural hydrocortisone hormone produced by the adrenal glands with primary glucocorticoid and minor mineralocorticoid effects. As a glucocorticoid receptor agonist, hydrocortisone promotes protein catabolism, gluconeogenesis, capillary wall stability, renal excretion of calcium, and suppresses immune and inflammatory responses.

SUMMARY

The disclosure provides an aqueous pharmaceutical formulation comprising from about 50 to about 150 mg/mL hydrocortisone sodium phosphate, from about 2.5 to about 12.5 mg/mL monothioglycerol, and water. In some embodiments, the formulation comprises from about 50 to about 60 mg/mL hydrocortisone sodium phosphate, from about 60 to about 70 mg/mL hydrocortisone sodium phosphate, or from about 70 to about 80 mg/mL hydrocortisone sodium phosphate. In some embodiments, the formulation comprises from about 60 to about 65 mg/mL hydrocortisone sodium phosphate, or from about 65 to about 70 mg/mL hydrocortisone sodium phosphate. In some embodiments, the formulation comprises from about 120 to about 130 mg/mL hydrocortisone sodium phosphate, from about 130 to about 140 mg/mL hydrocortisone sodium phosphate, or from about 140 to about 150 mg/mL hydrocortisone sodium phosphate. In some embodiments, the formulation comprises from about 130 to about 135 mg/mL hydrocortisone sodium phosphate, or from about 135 to about 140 mg/mL hydrocortisone sodium phosphate. In some embodiments, the formulation comprises about 50 mg/mL hydrocortisone sodium phosphate, about 55 mg/mL hydrocortisone sodium phosphate, about 60 mg/mL hydrocortisone sodium phosphate, about 65 mg/mL hydrocortisone sodium phosphate, about 70 mg/mL hydrocortisone sodium phosphate, about 75 mg/mL hydrocortisone sodium phosphate, about 80 mg/mL hydrocortisone sodium phosphate, about 85 mg/mL hydrocortisone sodium phosphate, about 90 mg/mL hydrocortisone sodium phosphate, about 95 mg/mL hydrocortisone sodium phosphate, about 100 mg/mL hydrocortisone sodium phosphate, about 105 mg/mL hydrocortisone sodium phosphate, about 110 mg/mL hydrocortisone sodium phosphate, about 115 mg/mL hydrocortisone sodium phosphate, about 120 mg/mL hydrocortisone sodium phosphate, about 125 mg/mL hydrocortisone sodium phosphate, about 130 mg/mL hydrocortisone sodium phosphate, about 135 mg/mL hydrocortisone sodium phosphate, about 140 mg/mL hydrocortisone sodium phosphate, about 145 mg/mL hydrocortisone sodium phosphate, or about 150 mg/mL hydrocortisone sodium phosphate. In some embodiments, the formulation comprises about 60 mg/mL hydrocortisone sodium phosphate, about 61 mg/mL hydrocortisone sodium phosphate, about 62 mg/mL hydrocortisone sodium phosphate, about 63 mg/mL hydrocortisone sodium phosphate, about 64 mg/mL hydrocortisone sodium phosphate, about 65 mg/mL hydrocortisone sodium phosphate, about 66 mg/mL hydrocortisone sodium phosphate, about 67 mg/mL hydrocortisone sodium phosphate, about 68 mg/mL hydrocortisone sodium phosphate, about 69 mg/mL hydrocortisone sodium phosphate, or about 70 mg/mL hydrocortisone sodium phosphate. In some embodiments, the formulation comprises about 67 mg/mL hydrocortisone sodium phosphate, about 67.1 mg/mL hydrocortisone sodium phosphate, about 67.2 mg/mL hydrocortisone sodium phosphate, about 67.3 mg/mL hydrocortisone sodium phosphate, about 67.4 mg/mL hydrocortisone sodium phosphate, about 67.5 mg/mL hydrocortisone sodium phosphate, about 67.6 mg/mL hydrocortisone sodium phosphate, about 67.7 mg/mL hydrocortisone sodium phosphate, about 67.8 mg/mL hydrocortisone sodium phosphate, about 67.9 mg/mL hydrocortisone sodium phosphate, or about 68 mg/mL hydrocortisone sodium phosphate. In some embodiments, the formulation comprises about 130 mg/mL hydrocortisone sodium phosphate, about 131 mg/mL hydrocortisone sodium phosphate, about 132 mg/mL hydrocortisone sodium phosphate, about 133 mg/mL hydrocortisone sodium phosphate, about 134 mg/mL hydrocortisone sodium phosphate, about 135 mg/mL hydrocortisone sodium phosphate, about 136 mg/mL hydrocortisone sodium phosphate, about 137 mg/mL hydrocortisone sodium phosphate, about 138 mg/mL hydrocortisone sodium phosphate, about 139 mg/mL hydrocortisone sodium phosphate, or about 140 mg/mL hydrocortisone sodium phosphate. In some embodiments, the formulation comprises about 134 mg/mL hydrocortisone sodium phosphate, about 134.1 mg/mL hydrocortisone sodium phosphate, about 134.2 mg/mL hydrocortisone sodium phosphate, about 134.3 mg/mL hydrocortisone sodium phosphate, about 134.4 mg/mL hydrocortisone sodium phosphate, about 134.5 mg/mL hydrocortisone sodium phosphate, about 134.6 mg/mL hydrocortisone sodium phosphate, about 134.7 mg/mL hydrocortisone sodium phosphate, about 134.8 mg/mL hydrocortisone sodium phosphate, about 134.9 mg/mL hydrocortisone sodium phosphate, or about 135 mg/mL hydrocortisone sodium phosphate.

In some embodiments, the disclosure provides a hydrocortisone sodium phosphate aqueous pharmaceutical formulation described herein, the formulation comprising from about 2.5 to about 3.5 mg/mL monothioglycerol, from about 3.5 to about 4.5 mg/mL monothioglycerol, from about 4.5 to about 5.5 mg/mL monothioglycerol, from about 5.5 to about 6.5 mg/mL monothioglycerol, from about 6.5 to about 7.5 mg/mL monothioglycerol, from about 7.5 to about 8.5 mg/mL monothioglycerol, from about 8.5 to about 9.5 mg/mL monothioglycerol, from about 9.5 to about 10.5 mg/mL monothioglycerol, from about 10.5 to about 11.5 mg/mL monothioglycerol, or from about 11.5 to about 12.5 mg/mL monothioglycerol. In some embodiments, the formulation comprises from about 4 to about 4.25 mg/mL monothioglycerol, from about 4.25 to about 4.5 mg/mL monothioglycerol, from about 4.5 to about 4.75 mg/mL monothioglycerol, from about 4.75 to about 5 mg/mL monothioglycerol, from about 5 to about 5.25 mg/mL monothioglycerol, from about 5.25 to about 5.5 mg/mL monothioglycerol, from about 5.5 to about 5.75 mg/mL monothioglycerol, or from about 5.75 to about 6 mg/mL monothioglycerol. In some embodiments, the formulation comprises from about 9 to about 9.25 mg/mL monothioglycerol, from about 9.25 to about 9.5 mg/mL monothioglycerol, from about 9.5 to about 9.75 mg/mL monothioglycerol, from about 9.75 to about 10 mg/mL monothioglycerol, from about 10 to about 10.25 mg/mL monothioglycerol, from about 10.25 to about 10.5 mg/mL monothioglycerol, from about 10.5 to about 10.75 mg/mL monothioglycerol, or from about 10.75 to about 11 mg/mL monothioglycerol. In some embodiments, the formulation comprises about 4.5 mg/mL monothioglycerol, about 4.6 mg/mL monothioglycerol, about 4.7 mg/mL monothioglycerol, about 4.8 mg/mL monothioglycerol, about 4.9 mg/mL monothioglycerol, about 5 mg/mL monothioglycerol, about 5.1 mg/mL monothioglycerol, about 5.2 mg/mL monothioglycerol, about 5.3 mg/mL monothioglycerol, about 5.4 mg/mL monothioglycerol, or about 5.5 mg/mL monothioglycerol. In some embodiments, the formulation comprises about 9.5 mg/mL monothioglycerol, about 9.6 mg/mL monothioglycerol, about 9.7 mg/mL monothioglycerol, about 9.8 mg/mL monothioglycerol, about 9.9 mg/mL monothioglycerol, about 10 mg/mL monothioglycerol, about 10.1 mg/mL monothioglycerol, about 10.2 mg/mL monothioglycerol, about 10.3 mg/mL monothioglycerol, about 10.4 mg/mL monothioglycerol, or about 10.5 mg/mL monothioglycerol.

In some embodiments, the disclosure provides a hydrocortisone sodium phosphate and monothioglycerol aqueous pharmaceutical formulation described herein, the formulation further comprising from about 0.5 to about 2.5 mg/mL monobasic sodium phosphate.

In some embodiments, the disclosure provides a hydrocortisone sodium phosphate and monothioglycerol aqueous pharmaceutical formulation described herein, the formulation further comprising from about 5 to about 25 mg/mL dibasic sodium phosphate.

In some embodiments, the disclosure provides a hydrocortisone sodium phosphate and monothioglycerol aqueous pharmaceutical formulation described herein, the formulation further comprising from about 0.1 to about 1 mg/mL disodium EDTA.

In some embodiments, the disclosure provides a hydrocortisone sodium phosphate and monothioglycerol aqueous pharmaceutical formulation described herein, wherein the pharmaceutical formulation has a pH from about 7.5 to about 9.5.

In some embodiments, the disclosure provides a hydrocortisone sodium phosphate and monothioglycerol aqueous pharmaceutical formulation described herein, wherein the pharmaceutical formulation has a pH of about 7.5, about 7.6, about 7.7, about 7.8, about 7.9, about 8, about 8.1, about 8.2, about 8.3, about 8.4, about 8.5, about 8.6, about 8.7, about, 8.8, about 8.9, or about 9.

In some embodiments, the disclosure provides a hydrocortisone sodium phosphate and monothioglycerol aqueous pharmaceutical formulation described herein, wherein the formulation comprises from no impurities to less than, or no more than 0.05% impurities upon formulation.

In some embodiments, the disclosure provides a hydrocortisone sodium phosphate and monothioglycerol aqueous pharmaceutical formulation described herein, wherein the formulation comprises from no impurities to less than, or no more than 0.07% impurities upon storage at 25° C. for about 3 months.

In some embodiments, the disclosure provides a hydrocortisone sodium phosphate and monothioglycerol aqueous pharmaceutical formulation described herein, wherein upon storage at 25° C. for about 3 months, the formulation comprises from no impurities to less than, or no more than 0.01% impurities, from no impurities to less than, or no more than 0.02% impurities, from no impurities to less than, or no more than 0.03% impurities, from no impurities to less than, or no more than 0.04% impurities, from no impurities to less than, or no more than 0.05% impurities, from no impurities to less than, or no more than 0.06% impurities, or from no impurities to less than, or no more than 0.07% impurities.

In some embodiments, the disclosure provides a hydrocortisone sodium phosphate and monothioglycerol aqueous pharmaceutical formulation described herein, wherein the formulation comprises from no impurities to less than, or no more than 0.20% impurities upon storage at 25° C. for about 6 months.

In some embodiments, the disclosure provides a hydrocortisone sodium phosphate and monothioglycerol aqueous pharmaceutical formulation described herein, wherein upon storage at 25° C. for about 6 months, the formulation comprises from no impurities to less than, or no more than 0.1% impurities, from no impurities to less than, or no more than 0.11% impurities, from no impurities to less than, or no more than 0.12% impurities, from no impurities to less than, or no more than 0.13% impurities, from no impurities to less than, or no more than 0.14% impurities, from no impurities to less than, or no more than 0.15% impurities, from no impurities to less than, or no more than 0.16% impurities, from no impurities to less than, or no more than 0.17% impurities, from no impurities to less than, or no more than 0.18% impurities, from no impurities to less than, or no more than 0.19% impurities, or from no impurities to less than, or no more than 0.2% impurities.

In some embodiments, the disclosure provides a hydrocortisone sodium phosphate and monothioglycerol aqueous pharmaceutical formulation described herein, wherein upon storage at 40° C. for about 1 month, the formulation comprises from no impurities to less than, or no more than 0.35% impurities.

In some embodiments, the disclosure provides a hydrocortisone sodium phosphate and monothioglycerol aqueous pharmaceutical formulation described herein, wherein upon storage at 40° C. for about 2 months, the formulation comprises from no impurities to less than, or no more than 0.7% impurities.

In some embodiments, the disclosure provides a hydrocortisone sodium phosphate and monothioglycerol aqueous pharmaceutical formulation described herein, wherein upon storage at 40° C. for about 3 months, the formulation comprises from no impurities to less than, or no more than 1.5% impurities.

In some embodiments, the disclosure provides a hydrocortisone sodium phosphate and monothioglycerol aqueous pharmaceutical formulation described herein, wherein upon storage at 40° C. for about 6 months, the formulation comprises from no impurities to less than, or no more than 2% impurities.

In one embodiment, the disclosure a pharmaceutical formulation comprising hydrocortisone, a hydrocortisone prodrug, and/or a pharmaceutically acceptable salt of any one thereof, and one or more inactive ingredients. In some embodiments, the hydrocortisone prodrug is a hydrocortisone ester. In some embodiments, the hydrocortisone prodrug or pharmaceutically acceptable salt thereof is selected from hydrocortisone sodium phosphate, hydrocortisone sodium succinate, hydrocortisone hydrogen succinate, hydrocortisone butyrate, hydrocortisone acetate. In some embodiments, the hydrocortisone prodrug or pharmaceutically acceptable salt thereof is hydrocortisone sodium phosphate. In some embodiments, the concentration of hydrocortisone sodium phosphate in the pharmaceutical formulation is between about 5 mg/mL and about 100 mg/mL. In some embodiments, the concentration of hydrocortisone sodium phosphate in the pharmaceutical formulation is between about 50 mg/mL and about 100 mg/mL. In some embodiments, the concentration of hydrocortisone sodium phosphate in the pharmaceutical formulation is between about 25 mg/mL and about 75 mg/mL. In some embodiments, the concentration of hydrocortisone sodium phosphate in the pharmaceutical formulation is about 50 mg/mL, about 51 mg/mL, about 52 mg/mL, about 53 mg/mL, about 54 mg/mL, about 55 mg/mL, about 56 mg/mL, about 57 mg/mL, about 58 mg/mL, about 59 mg/mL, about 60 mg/mL, about 61 mg/mL, about 62 mg/mL, about 63 mg/mL, about 64 mg/mL, about 65 mg/mL, about 66 mg/mL, about 67 mg/mL, about 68 mg/mL, about 69 mg/mL, or about 70 mg/mL. In some embodiments, the one or more inactive ingredients are selected from a buffer agent, a chelating agent, an antioxidant, a pH adjustor, and a solvent. In some embodiments, the buffer agent is selected from monobasic sodium phosphate anhydrous and dibasic sodium phosphate anhydrous. In some embodiments, the chelating agent is disodium EDTA. In some embodiments, the antioxidant is monothioglycerol. In some embodiments, the pH adjustor is selected from sodium hydroxide and HCl. In some embodiments, the solvent is water.

BRIEF DESCRIPTION OF THE DRAWINGS

The foregoing summary, as well as the following detailed description of embodiments of the invention, will be better understood when read in conjunction with the appended drawings and figures.

Figure 1:
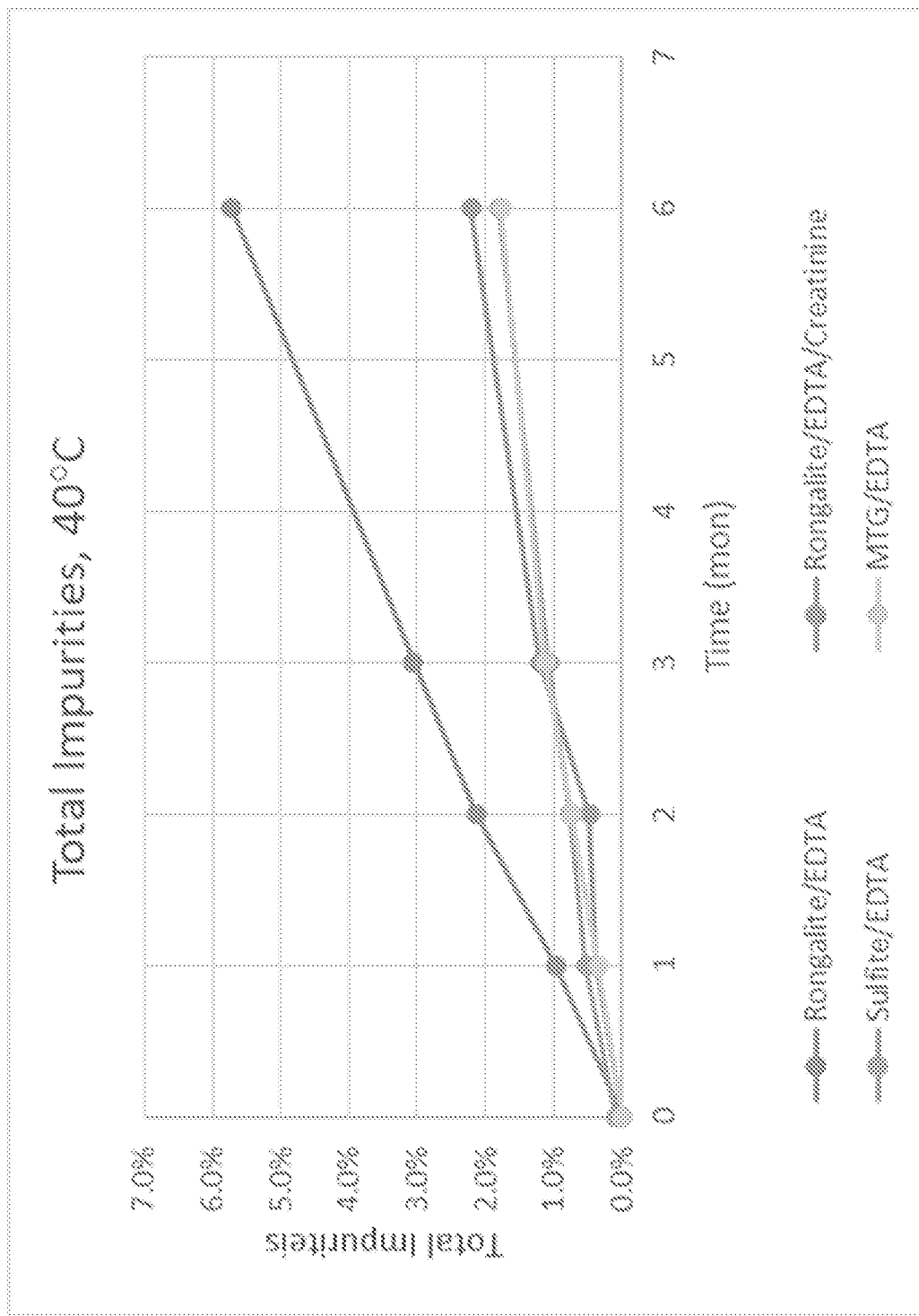
FIG. 1 illustrates the stability of three lead formulations.

While the above-identified drawings set forth presently disclosed embodiments, other embodiments are also contemplated, as noted in the discussion. This disclosure presents illustrative embodiments by way of representation and not limitation. Numerous other modifications and embodiments can be devised by those skilled in the art which fall within the scope and spirit of the principles of the presently disclosed embodiments.

DETAILED DESCRIPTION

The present invention is directed to pharmaceutical formulations including hydrocortisone, one or more hydrocortisone prodrugs, e.g., hydrocortisone esters, and/or any salts thereof, including, without limitation, stable liquid formulations using hydrocortisone sodium phosphate as the active ingredient.

Definitions

Unless defined otherwise, all technical and scientific terms used herein have the same meaning as is commonly understood by one of skill in the art to which this invention belongs. All patents and publications referred to herein are incorporated by reference in their entireties.

As used herein, the terms "administer," "administration," or "administering" refer to (1) providing, giving, dosing, and/or prescribing by either a health practitioner or his authorized agent or under his or her direction according to the disclosure, and/or (2) putting into, taking, or consuming by a subject, for example a mammal, including a human, according to the disclosure.

The terms "co-administration," "co-administering," "administered in combination with," "administering in combination with," "simultaneous," and "concurrent," as used herein, encompass administration of two or more active pharmaceutical ingredients to a subject so that both active pharmaceutical ingredients and/or their metabolites are present in the subject at the same time. Co-administration includes simultaneous administration in separate compositions, administration at different times in separate compositions, or administration in a composition in which two or more active pharmaceutical ingredients are present. In some embodiments, simultaneous administration in separate compositions and administration in a composition in which both agents are present are preferred.

The term "effective amount" or "therapeutically effective amount" refers to that amount of a compound or combination of compounds as described herein that is sufficient to effect the intended application including, but not limited to, disease treatment. A therapeutically effective amount may vary depending upon the intended application (in vitro or in vivo), or the subject and disease condition being treated (e.g., the weight, age and gender of the subject), the severity of the disease condition, the manner of administration, etc., which can readily be determined by one of ordinary skill in the art. The term also applies to a dose that will induce a particular response in target cells (e.g., the reduction of platelet adhesion and/or cell migration). The specific dose will vary depending on the subject to whom the dose is to be administered, the particular compounds chosen, the dosing regimen to be followed, whether the compound is administered in combination with other compounds, timing of administration, the tissue to which it is administered, and the physical delivery system in which the compound is carried.

A "therapeutic effect" as that term is used herein, encompasses a therapeutic benefit and/or a prophylactic benefit. A prophylactic effect includes delaying or eliminating the appearance of a disease or condition, delaying or eliminating the onset of symptoms of a disease or condition, slowing, halting, or reversing the progression of a disease or condition, or any combination thereof.

As used herein, the terms "treat," "treatment," and/or "treating" may refer to the management of a disease, disorder, or pathological condition, or symptom thereof with the intent to cure, ameliorate, stabilize, and/or control the disease, disorder, pathological condition or symptom thereof. Regarding control of the disease, disorder, or pathological condition more specifically, "control" may include the absence of condition progression, as assessed by the response to the methods recited herein, where such response may be complete (e.g., placing the disease in remission) or partial (e.g., lessening or ameliorating any symptoms associated with the condition). As used herein, the terms "prevent," "preventing," and/or "prevention" may refer to reducing the risk of developing a disease, disorder, or pathological condition.

The term "pharmaceutically acceptable salt" refers to salts derived from a variety of organic and inorganic counter ions known in the art. Pharmaceutically acceptable acid addition salts can be formed with inorganic acids and organic acids. Preferred inorganic acids from which salts can be derived include, for example, hydrochloric acid, hydrobromic acid, sulfuric acid, nitric acid and phosphoric acid. Preferred organic acids from which salts can be derived include, for example, acetic acid, propionic acid, glycolic acid, pyruvic acid, oxalic acid, maleic acid, malonic acid, phosphoric acid, succinic acid, fumaric acid, tartaric acid, citric acid, benzoic acid, cinnamic acid, mandelic acid, methanesulfonic acid, ethanesulfonic acid, p-toluenesulfonic acid and salicylic acid. Pharmaceutically acceptable base addition salts can be formed with inorganic and organic bases. Inorganic bases from which salts can be derived include, for example, sodium, potassium, lithium, ammonium, calcium, magnesium, iron, zinc, copper, manganese and aluminum. Organic bases from which salts can be derived include, for example, primary, secondary, and tertiary amines, substituted amines including naturally occurring substituted amines, cyclic amines and basic ion exchange resins. Specific examples include isopropylamine, trimethylamine, diethylamine, triethylamine, tripropylamine, and ethanolamine. In some embodiments, the pharmaceutically acceptable base addition salt is chosen from ammonium, potassium, sodium, calcium, and magnesium salts. The term "cocrystal" refers to a molecular complex derived from a number of cocrystal formers known in the art. Unlike a salt, a cocrystal typically does not involve hydrogen transfer between the cocrystal and the drug, and instead involves intermolecular interactions, such as hydrogen bonding, aromatic ring stacking, or dispersive forces, between the cocrystal former and the drug in the crystal structure.

"Pharmaceutically acceptable carrier" or "pharmaceutically acceptable excipient" or "physiologically compatible" carrier or carrier medium is intended to include any and all solvents, dispersion media, coatings, antibacterial and antifungal agents, isotonic and absorption delaying agents, and inert ingredients. The use of such pharmaceutically acceptable carriers or pharmaceutically acceptable excipients for active pharmaceutical ingredients is well known in the art. Except insofar as any conventional pharmaceutically acceptable carrier or pharmaceutically acceptable excipient is incompatible with the active pharmaceutical ingredient, its use in the therapeutic compositions of the invention is contemplated. Additional active pharmaceutical ingredients, such as other drugs, can also be incorporated into the described compositions and methods.

A "prodrug" refers to a derivative of a compound described herein, the pharmacologic action of which results from the conversion by chemical or metabolic processes in vivo to the active compound. Prodrugs include, without limitation, compounds wherein an amino acid residue, or a polypeptide chain of two or more (e.g., two, three or four) amino acid residues is covalently joined through an amide or ester bond to a free amino, hydroxyl or carboxylic acid group of hydrocortisone. The amino acid residues include but are not limited to the 20 naturally occurring amino acids commonly designated by one or three letter symbols but also include, for example, 4-hydroxyproline, hydroxylysine, desmosine, isodesmosine, 3-methylhistidine, beta-alanine, gamma-aminobutyric acid, citrulline, homocysteine, homoserine, ornithine and methionine sulfone. Additional types of prodrugs are also encompassed. For instance, free carboxyl groups can be derivatized as amides or alkyl esters (e.g., methyl esters and acetoxy methyl esters). Prodrug esters as employed herein includes esters and carbonates formed by reacting one or more hydroxyls of compounds of the method of the invention with alkyl, alkoxy, or aryl substituted acylating agents employing procedures known to those skilled in the art to generate acetates, phosphates, succinates, butyrates, pivalates, methylcarbonates, benzoates and the like. As further examples, free hydroxyl groups may be derivatized using groups including but not limited to hemisuccinates, phosphate esters, dimethylaminoacetates, and phosphoryloxymethyloxycarbonyls, as outlined in Advanced Drug Delivery Reviews, 1996, 19, 115. Carbamate prodrugs of hydroxyl and amino groups are also included, as are carbonate prodrugs, sulfonate prodrugs, sulfonate esters and sulfate esters of hydroxyl groups. Free amines can also be derivatized to amides, sulfonamides or phosphonamides. All of the stated prodrug moieties may incorporate groups including but not limited to ether, amine and carboxylic acid functionalities. Moreover, any compound that can be converted in vivo to provide the bioactive agent (e.g., hydrocortisone) is a prodrug within the scope of the invention. Various forms of prodrugs are well known in the art. A comprehensive description of prodrugs and prodrug derivatives are described in: (a) The Practice of Medicinal Chemistry, Camille G. Wermuth et al., (Academic Press, 1996); (b) Design of Prodrugs, edited by H. Bundgaard, (Elsevier, 1985); (c) A Textbook of Drug Design and Development, P. Krogsgaard-Larson and H. Bundgaard, eds., (Harwood Academic Publishers, 1991). In general, prodrugs may be designed to improve the penetration of a drug across biological membranes in order to obtain improved drug absorption, to prolong duration of action of a drug (slow release of the parent drug from a prodrug, decreased first-pass metabolism of the drug), to target the drug action (e.g., organ or tumor-targeting, lymphocyte targeting), to modify or improve aqueous solubility of a drug (e.g., i.v. preparations and eyedrops), to improve topical drug delivery (e.g., dermal and ocular drug delivery), to improve the chemical/enzymatic stability of a drug, or to decrease off-target drug effects, and more generally in order to improve the therapeutic efficacy of the compounds utilized in the invention.

Unless otherwise stated, the chemical structures depicted herein are intended to include compounds which differ only in the presence of one or more isotopically enriched atoms. For example, compounds where one or more hydrogen atoms is replaced by deuterium or tritium, or wherein one or more carbon atoms is replaced by $^{13}$C-enriched or $^{14}$C-enriched carbons, are within the scope of this invention.

When ranges are used herein to describe, for example, physical or chemical properties such as molecular weight or chemical formulae, all combinations and subcombinations of ranges and specific embodiments therein are intended to be included. Use of the term "about" when referring to a number or a numerical range means that the number or numerical range referred to is an approximation within experimental variability (or within statistical experimental error), and thus the number or numerical range may vary. The variation is typically from 0% to 15%, from 0% to 10%, from 0% to 5%, or the like, of the stated number or numerical range.

As used herein, the term "about" means that amounts, sizes, formulations, parameters, shapes and other quantities and characteristics are not, and need not be exact, but may be approximate and/or larger or smaller, as desired, reflecting tolerances, conversion factors, rounding off, measurement error and the like, and other factors known to those of skill in the art. In general, an amount, size, formulation, parameter, shape or other quantity or characteristic is "about" or "approximate" whether or not expressly stated to be such. The term "about" generally refers to a particular numeric value that is within an acceptable error range as determined by one of ordinary skill in the art, which will depend in part on how the numeric value is measured or determined, i.e., the limitations of the measurement system. For example, "about" can mean a range of ±20%, ±10%, or ±5% of a given numeric value.

The transitional terms "comprising", "consisting essentially of" and "consisting of", when used in the appended claims, in original and amended form, define the claim scope with respect to what unrecited additional claim elements or steps, if any, are excluded from the scope of the claim(s). The term "comprising" is intended to be inclusive or open-ended and does not exclude any additional, unrecited element, method, step or material. The term "consisting of" excludes any element, step or material other than those specified in the claim and, in the latter instance, impurities ordinarily associated with the specified material(s). The term "consisting essentially of" limits the scope of a claim to the specified elements, steps or material(s) and those that do not materially affect the basic and novel characteristic(s) of the claimed invention. All compounds, compositions, formulations, and methods described herein that embody the present invention can, in alternate embodiments, be more specifically defined by any of the transitional terms "comprising," "consisting essentially of," and "consisting of." The term "comprising" (and related terms such as "comprise" or "comprises" or "having" or "including") includes those embodiments such as, for example, an embodiment of any composition of matter, method, or process that "consist of" or "consist essentially of" the described features.

"Alkyl" refers to a straight or branched hydrocarbon chain radical consisting solely of carbon and hydrogen atoms, containing no unsaturation, having from one to ten carbon atoms (e.g., (C$_{1-10}$)alkyl or C$_{1-10}$ alkyl). Whenever it appears herein, a numerical range such as "1 to 10" refers to each integer in the given range, e.g., "1 to 10 carbon atoms" means that the alkyl group may consist of 1 carbon atom, 2 carbon atoms, 3 carbon atoms, etc., up to and including 10 carbon atoms, although the definition is also intended to cover the occurrence of the term "alkyl" where no numerical range is specifically designated. Typical alkyl groups include, but are in no way limited to, methyl, ethyl, propyl, isopropyl, n-butyl, isobutyl, sec-butyl isobutyl, tertiary butyl, pentyl, isopentyl, neopentyl, hexyl, septyl, octyl, nonyl and decyl. The alkyl moiety may be attached to the rest of the molecule by a single bond, such as for example, methyl (Me), ethyl (Et), n-propyl (Pr), 1-methylethyl (isopropyl), n-butyl, n-pentyl, 1,1-dimethylethyl (t-butyl) and 3-methylhexyl. Unless stated otherwise specifically in the specification, an alkyl group is optionally substituted by one or more of substituents which are independently heteroalkyl, acylsulfonamido, alkenyl, alkynyl, cycloalkyl, heterocycloalkyl, hydroxamate, aryl, arylalkyl, heteroaryl, heteroarylalkyl, hydroxy, halo, cyano, trifluoromethyl, trifluoromethoxy, nitro, trimethylsilanyl, —OR$^a$, —SR$^a$, —S(O)$_t$R$^a$— (where t is 1 or 2), —OC(O)—R$^a$, —N(R$^a$)$_2$, —C(O)R$^a$, —C(O)OR$^a$, —OC(O)N(R$^a$)$_2$, —C(O)N(R$^a$)$_2$, —N(R$^a$)C(O)OR$^a$, —N(R$^a$)C(O)R$^a$, —N(R$^a$)C(O)N(R$^a$)$_2$, N(R$^a$)C(NR$^a$)N(R$^a$)$_2$, —N(R$^a$)S(O)$_t$R$^a$ (where t is 1 or 2), —S(O)$_t$OR$^a$ (where t is 1 or 2), —S(O)$_t$N(R$^a$)$_2$ (where t is 1 or 2), or PO$_3$(R$^a$)$_2$ where each R$^a$ is independently hydrogen, alkyl, fluoroalkyl, carbocyclyl, carbocyclylalkyl, aryl, aralkyl, heterocycloalkyl, heterocycloalkylalkyl, heteroaryl or heteroarylalkyl. The alkyl moiety, whether saturated or unsaturated, may be branched, straight chain, or cyclic.

An "alkene" or "alkenyl" moiety refers to a group consisting of at least two carbon atoms and at least one carbon-carbon double bond, and an "alkyne" moiety refers to a group consisting of at least two carbon atoms and at least one carbon-carbon triple bond.

"Alkenyl" refers to a straight or branched hydrocarbon chain radical group consisting solely of carbon and hydrogen atoms, containing at least one double bond, and having from two to ten carbon atoms (i.e., (C$_{2-10}$)alkenyl or C$_{2-10}$ alkenyl). Whenever it appears herein, a numerical range such as "2 to 10" refers to each integer in the given range—e.g., "2 to 10 carbon atoms" means that the alkenyl group may consist of 2 carbon atoms, 3 carbon atoms, etc., up to and including 10 carbon atoms. The alkenyl moiety may be attached to the rest of the molecule by a single bond, such as for example, ethenyl (i.e., vinyl), prop-1-enyl (i.e., allyl), but-1-enyl, pent-1-enyl and penta-1,4-dienyl. Unless stated otherwise specifically in the specification, an alkenyl group is optionally substituted by one or more substituents which are independently alkyl, heteroalkyl, acylsulfonamido, alkenyl, alkynyl, cycloalkyl, heterocycloalkyl, hydroxamate, aryl, arylalkyl, heteroaryl, heteroarylalkyl, hydroxy, halo, cyano, trifluoromethyl, trifluoromethoxy, nitro, trimethylsilanyl, —OR$^a$, —SR$^a$, —S(O)$_t$R$^a$— (where t is 1 or 2), —OC(O)—R$^a$, —N(IV)$_2$, —C(O)R$^a$, —C(O)OR$^a$, —OC(O)N(R$^a$)$_2$, —C(O)N(R$^a$)$_2$, —N(R$^a$)C(O)OR$^a$, —N(R$^a$)C(O)R$^a$, —N(R$^a$)C(O)N(R$^a$)$_2$, N(R$^a$)C(NR$^a$)N(R$^a$)$_2$, —N(R$^a$)S(O)$_t$R$^a$ (where t is 1 or 2), —S(O)$_t$R$^a$ (where t is 1 or 2), —S(O)$_t$N(R$^a$)$_2$ (where t is 1 or 2), or PO$_3$(R$^a$)$_2$, where each R$^a$ is independently hydrogen, alkyl, fluoroalkyl, carbocyclyl, carbocyclylalkyl, aryl, aralkyl, heterocycloalkyl, heterocycloalkylalkyl, heteroaryl or heteroarylalkyl.

"Alkenyl-cycloalkyl" refers to an -(alkenyl)cycloalkyl radical where alkenyl and cycloalkyl are as disclosed herein and which are optionally substituted by one or more of the substituents described as suitable substituents for alkenyl and cycloalkyl respectively.

"Cycloalkyl" refers to a monocyclic or polycyclic radical that contains only carbon and hydrogen, and may be saturated, or partially unsaturated. Cycloalkyl groups include groups having from 3 to 10 ring atoms (i.e., ($C_{3-10}$)cycloalkyl or $C_{3-10}$ cycloalkyl). Whenever it appears herein, a numerical range such as "3 to 10" refers to each integer in the given range—e.g., "3 to 10 carbon atoms" means that the cycloalkyl group may consist of 3 carbon atoms, etc., up to and including 10 carbon atoms. Illustrative examples of cycloalkyl groups include, but are not limited to the following moieties: cyclopropyl, cyclobutyl, cyclopentyl, cyclopentenyl, cyclohexyl, cyclohexenyl, cycloheptyl, cyclooctyl, cyclononyl, cyclodecyl, norbornyl, and the like. Unless stated otherwise specifically in the specification, a cycloalkyl group is optionally substituted by one or more substituents which independently are: alkyl, heteroalkyl, alkenyl, alkynyl, cycloalkyl, acylsulfonamido, heterocycloalkyl, hydroxamate, aryl, arylalkyl, heteroaryl, heteroarylalkyl, hydroxy, halo, cyano, trifluoromethyl, trifluoromethoxy, nitro, trimethylsilanyl, —$OR^a$, —$SR^a$, —$S(O)_tR^a$— (where t is 1 or 2), —$S(O)_tR^a$— (where t is 1 or 2), —OC(O)—$R^a$, —$N(R^a)_2$, —C(O)$R^a$, —C(O)O$R^a$, —OC(O)N($R^a$)$_2$, —C(O)N($R^a$)$_2$, —N($R^a$)C(O)O$R^a$, —N($R^a$)C(O)$R^a$, —N($R^a$)C(O)N($R^a$)$_2$, N($R^a$)C(N$R^a$)N($R^a$)$_2$, —N($R^a$)S(O)$_tR^a$ (where t is 1 or 2), —S(O)$_t$O$R^a$ (where t is 1 or 2), —S(O)$_t$N($R^a$)$_2$ (where t is 1 or 2), or PO$_3$($R^a$)$_2$, where each $R^a$ is independently hydrogen, alkyl, fluoroalkyl, carbocyclyl, carbocyclylalkyl, aryl, aralkyl, heterocycloalkyl, heterocycloalkylalkyl, heteroaryl or heteroarylalkyl.

"Cycloalkyl-alkenyl" refers to a -(cycloalkyl)alkenyl radical where cycloalkyl and alkenyl are as disclosed herein and which are optionally substituted by one or more of the substituents described as suitable substituents for cycloalkyl and alkenyl, respectively.

"Acyl" refers to the groups (alkyl)-C(O)—, (aryl)-C(O)—, (heteroaryl)-C(O)—, (heteroalkyl)-C(O)— and (heterocycloalkyl)-C(O)—, wherein the group is attached to the parent structure through the carbonyl functionality. If the R radical is heteroaryl or heterocycloalkyl, the hetero ring or chain atoms contribute to the total number of chain or ring atoms. Unless stated otherwise specifically in the specification, the alkyl, aryl or heteroaryl moiety of the acyl group is optionally substituted by one or more substituents which are independently alkyl, heteroalkyl, acylsulfonamido, alkenyl, alkynyl, cycloalkyl, heterocycloalkyl, hydroxamate, aryl, arylalkyl, heteroaryl, heteroarylalkyl, hydroxy, halo, cyano, trifluoromethyl, trifluoromethoxy, nitro, trimethylsilanyl, —$OR^a$, —$SR^a$, —S(O)$_tR^a$— (where t is 1 or 2), —OC(O)—$R^a$, —$N(R^a)_2$, —C(O)$R^a$, —C(O)O$R^a$, —OC(O)N($R^a$)$_2$, —C(O)N(V)$_2$, —N($R^a$)C(O)O$R^a$, —N($R^a$)C(O)$R^a$, —N($R^a$)C(O)N($R^a$)$_2$, N($R^a$)C(N$R^a$)N($R^a$)$_2$, —N($R^a$)S(O)$_tR^a$ (where t is 1 or 2), —S(O)$_t$O$R^a$ (where t is 1 or 2), —S(O)$_t$N($R^a$)$_2$ (where t is 1 or 2), or PO$_3$($R^a$)$_2$, where each $R^a$ is independently hydrogen, alkyl, fluoroalkyl, carbocyclyl, carbocyclylalkyl, aryl, aralkyl, heterocycloalkyl, heterocycloalkylalkyl, heteroaryl or heteroarylalkyl.

"Ester" refers to, without limitation, a chemical radical of formula —COOR, where R is selected from the group consisting of alkyl, cycloalkyl, aryl, heteroaryl (bonded through a ring carbon) and heteroalicyclic (bonded through a ring carbon). The procedures and specific groups to make esters are known to those of skill in the art and can readily be found in seminal sources such as Greene and Wuts, Protective Groups in Organic Synthesis, 3rd Ed., John Wiley & Sons, New York, N.Y., 1999, which is incorporated herein by reference in its entirety. Unless stated otherwise specifically in the specification, an ester group is optionally substituted by one or more substituents which independently are: alkyl, acylsulfonamido, heteroalkyl, alkenyl, alkynyl, cycloalkyl, heterocycloalkyl, hydroxamate, aryl, arylalkyl, heteroaryl, heteroarylalkyl, hydroxy, halo, cyano, trifluoromethyl, trifluoromethoxy, nitro, trimethylsilanyl, —$OR^a$, —$SR^a$, —$S(O)_tR^a$— (where t is 1 or 2), —OC(O)—$R^a$, —$N(R^a)_2$, —C(O)$R^a$, —C(O)O$R^a$, —OC(O)N($R^a$)$_2$, —C(O)N($R^a$)$_2$, —N($R^a$)C(O)O$R^a$, —N($R^a$)C(O)$R^a$, —N($R^a$)C(O)N($R^a$)$_2$, N($R^a$)C(N$R^a$)N($R^a$)$_2$, —N($R^a$)S(O)$_tR^a$ (where t is 1 or 2), —S(O)$_t$O$R^a$ (where t is 1 or 2), —S(O)$_t$N($R^a$)$_2$ (where t is 1 or 2), or PO$_3$($R^a$)$_2$, where each $R^a$ is independently hydrogen, alkyl, fluoroalkyl, carbocyclyl, carbocyclylalkyl, aryl, aralkyl, heterocycloalkyl, heterocycloalkylalkyl, heteroaryl or heteroarylalkyl.

"Ester" also refers to, without limitation, a phosphate.

"Fluoroalkyl" refers to an alkyl radical, as defined above, that is substituted by one or more fluoro radicals, as defined above, for example, trifluoromethyl, difluoromethyl, 2,2,2-trifluoroethyl, 1-fluoromethyl-2-fluoroethyl, and the like. The alkyl part of the fluoroalkyl radical may be optionally substituted as defined above for an alkyl group.

"Isomers" are different compounds that have the same molecular formula.

"Stereoisomers" are isomers that differ only in the way the atoms are arranged in space—i.e., having a different stereochemical configuration. "Enantiomers" are a pair of stereoisomers that are non-superimposable mirror images of each other. A 1:1 mixture of a pair of enantiomers is a "racemic" mixture. The term "(±)" is used to designate a racemic mixture where appropriate. "Diastereoisomers" are stereoisomers that have at least two asymmetric atoms, but which are not mirror-images of each other. The absolute stereochemistry is specified according to the Cahn-Ingold-Prelog R—S system. When a compound is a pure enantiomer the stereochemistry at each chiral carbon can be specified by either (R) or (S). Resolved compounds whose absolute configuration is unknown can be designated (+) or (−) depending on the direction (dextro- or levorotatory) which they rotate plane polarized light at the wavelength of the sodium D line. Certain of the compounds described herein contain one or more asymmetric centers and can thus give rise to enantiomers, diastereomers, and other stereoisomeric forms that can be defined, in terms of absolute stereochemistry, as (R) or (S). The present chemical entities, pharmaceutical compositions and methods are meant to include all such possible isomers, including racemic mixtures, optically pure forms and intermediate mixtures. Optically active (R)- and (S)-isomers can be prepared using chiral synthons or chiral reagents, or resolved using conventional techniques. When the compounds described herein contain olefinic double bonds or other centers of geometric asymmetry, and unless specified otherwise, it is intended that the compounds include both E and Z geometric isomers.

"Moiety" refers to a specific segment or functional group of a molecule. Chemical moieties are often recognized chemical entities embedded in or appended to a molecule.

"Tautomers" are structurally distinct isomers that interconvert by tautomerization. "Tautomerization" is a form of isomerization and includes prototropic or proton-shift tautomerization, which is considered a subset of acid-base chemistry. "Prototropic tautomerization" or "proton-shift tautomerization" involves the migration of a proton accompanied by changes in bond order, often the interchange of a single bond with an adjacent double bond. Where tautomerization is possible (e.g., in solution), a chemical equilibrium of tautomers can be reached. An example of tautomerization is keto-enol tautomerization. A specific example of keto-enol tautomerization is the interconversion of pentane-2,4-dione and 4-hydroxypent-3-en-2-one tautomers. Another example of tautomerization is phenol-keto tautomerization. A specific example of phenol-keto tautomerization is the interconversion of pyridin-4-ol and pyridin-4(1H)-one tautomers.

"Substituted" means that the referenced group may have attached one or more additional groups, radicals or moieties individually and independently selected from, for example, acyl, alkyl, alkylaryl, cycloalkyl, aralkyl, aryl, carbohydrate, carbonate, heteroaryl, heterocycloalkyl, hydroxamate, hydroxy, alkoxy, aryloxy, mercapto, alkylthio, arylthio, cyano, halo, carbonyl, ester, thiocarbonyl, isocyanato, thiocyanato, isothiocyanato, nitro, oxo, perhaloalkyl, perfluoroalkyl, phosphate, silyl, sulfinyl, sulfonyl, sulfonamidyl, sulfoxyl, sulfonate, urea, and amino, including mono- and di-substituted amino groups, and protected derivatives thereof. The substituents themselves may be substituted, for example, a cycloalkyl substituent may itself have a halide substituent at one or more of its ring carbons. The term "optionally substituted" means optional substitution with the specified groups, radicals or moieties.

DETAILED DESCRIPTION

Formulations

In one embodiment, the invention relates to a pharmaceutical formulation including hydrocortisone, one or more hydrocortisone prodrugs, e.g., a hydrocortisone ester, and/or any salts thereof.

Hydrocortisone is the name for the hormone cortisol when supplied as a medication. It is used in oral administration, intravenous injection, or topical application. It is used as an immunosuppressive drug, given by injection in the treatment of severe allergic reactions such as anaphylaxis and angioedema. It may be used topically for allergic rashes, eczema, psoriasis, itching and other inflammatory skin conditions.

Therapeutic hydrocortisone is a synthetic or semisynthetic analog of natural hydrocortisone hormone produced by the adrenal glands with primary glucocorticoid and minor mineralocorticoid effects. As a glucocorticoid receptor agonist, hydrocortisone promotes protein catabolism, gluconeogenesis, capillary wall stability, renal excretion of calcium, and suppresses immune and inflammatory responses.

The empirical formula of Hydrocortisone is $C_{21}H_{30}O_5$. The molecular weight is 362.46 g/mol. The structural formula is:

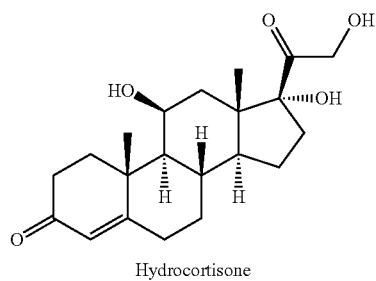

Hydrocortisone

Hydrocortisone is available as a crystalline, white powder and has bitter taste. Its melting point is 220° C. It is a water insoluble with a reported solubility of about 0.32 mg/mL in water. Reported solubility in propylene glycol is 12.7 mg/mL. The octanol/water partition coefficient value of hydrocortisone is 1.61. It is sensitive to light and unstable in strong acids and alkalies.

Hydrocortisone sodium phosphate is an organic salt. Its molecular formula is $C_{21}H_{29}Na_2O_8P$ and its molecular weight is 486.4 g/mol, and it has the following structure:

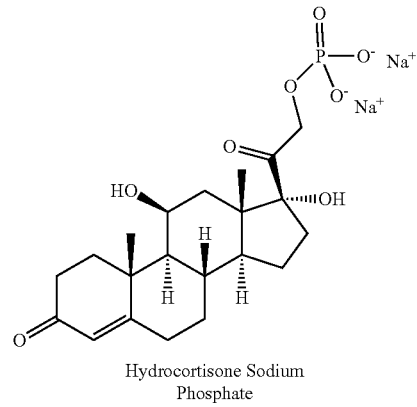

Hydrocortisone Sodium Phosphate

Any antioxidant suitable for parenteral administration can be used in the formulations of the invention. In some embodiments, the antioxidant is one or more of butylated hydroxy toluene (BHT), tocopherol, butylated hydroxy anisole (BHA), ascorbyl palmitate, ascorbic acid and salts thereof, vitamin E, niacinamide, methionine, monothioglycerol, sodium bisulfite, cysteine, dithionite sodium, gentisic acid, and/or glutamate monosodium.

Pharmaceutical Compositions

In some embodiments, the concentration of the hydrocortisone, hydrocortisone prodrug, i.e., hydrocortisone ester, or pharmaceutically acceptable salts of thereof, described herein is less than, or no more than, for example, 100%, 90%, 80%, 70%, 60%, 50%, 40%, 30%, 20%, 19%, 18%, 17%, 16%, 15%, 14%, 13%, 12%, 11%, 10%, 9%, 8%, 7%, 6%, 5%, 4%, 3%, 2%, 1%, 0.5%, 0.4%, 0.3%, 0.2%, 0.1%, 0.09%, 0.08%, 0.07%, 0.06%, 0.05%, 0.04%, 0.03%, 0.02%, 0.01%, 0.009%, 0.008%, 0.007%, 0.006%, 0.005%, 0.004%, 0.003%, 0.002%, 0.001%, 0.0009%, 0.0008%, 0.0007%, 0.0006%, 0.0005%, 0.0004%, 0.0003%, 0.0002% or 0.0001% w/w, w/v, or v/v of the pharmaceutical formulations described herein.

In some embodiments, the concentration of the hydrocortisone, hydrocortisone prodrug, i.e., hydrocortisone ester, or pharmaceutically acceptable salts of thereof, described herein is greater than 90%, 80%, 70%, 60%, 50%, 40%, 30%, 20%, 19.75%, 19.50%, 19.25% 19%, 18.75%, 18.50%, 18.25% 18%, 17.75%, 17.50%, 17.25% 17%, 16.75%, 16.50%, 16.25% 16%, 15.75%, 15.50%, 15.25% 15%, 14.75%, 14.50%, 14.25% 14%, 13.75%, 13.50%, 13.25% 13%, 12.75%, 12.50%, 12.25% 12%, 11.75%, 11.50%, 11.25% 11%, 10.75%, 10.50%, 10.25% 10%, 9.75%, 9.50%, 9.25% 9%, 8.75%, 8.50%, 8.25% 8%, 7.75%, 7.50%, 7.25% 7%, 6.75%, 6.50%, 6.25% 6%, 5.75%, 5.50%, 5.25% 5%, 4.75%, 4.50%, 4.25%, 4%, 3.75%, 3.50%, 3.25%, 3%, 2.75%, 2.50%, 2.25%, 2%, 1.75%, 1.50%, 125%, 1%, 0.5%, 0.4%, 0.3%, 0.2%, 0.1%, 0.09%, 0.08%, 0.07%, 0.06%, 0.05%, 0.04%, 0.03%, 0.02%, 0.01%, 0.009%, 0.008%, 0.007%, 0.006%, 0.005%, 0.004%, 0.003%, 0.002%, 0.001%, 0.0009%, 0.0008%, 0.0007%, 0.0006%, 0.0005%, 0.0004%, 0.0003%, 0.0002% or 0.0001% w/w, w/v, or v/v of the pharmaceutical formulations described herein.

In some embodiments, the concentration of the hydrocortisone, hydrocortisone prodrug, i.e., hydrocortisone ester, or pharmaceutically acceptable salts of thereof, described herein is in the range from about 0.0001% to about 50%, about 0.001% to about 40%, about 0.01% to about 30%, about 0.02% to about 29%, about 0.03% to about 28%, about 0.04% to about 27%, about 0.05% to about 26%, about 0.06% to about 25%, about 0.07% to about 24%, about 0.08% to about 23%, about 0.09% to about 22%, about 0.1% to about 21%, about 0.2% to about 20%, about 0.3% to about 19%, about 0.4% to about 18%, about 0.5% to about 17%, about 0.6% to about 16%, about 0.7% to about 15%, about 0.8% to about 14%, about 0.9% to about 12% or about 1% to about 10% w/w, w/v, or v/v of the pharmaceutical formulations described herein.

In some embodiments, the concentration of the hydrocortisone, hydrocortisone prodrug, i.e., hydrocortisone ester, or pharmaceutically acceptable salts of thereof, described herein is in the range from about 0.001% to about 10%, about 0.01% to about 5%, about 0.02% to about 4.5%, about 0.03% to about 4%, about 0.04% to about 3.5%, about 0.05% to about 3%, about 0.06% to about 2.5%, about 0.07% to about 2%, about 0.08% to about 1.5%, about 0.09% to about 1%, about 0.1% to about 0.9% w/w, w/v, or v/v of the pharmaceutical formulations described herein.

In some embodiments, the amount of each of the active and/or inactive pharmaceutical ingredients provided in the pharmaceutical compositions of the invention, such as a hydrocortisone, hydrocortisone prodrug, i.e., hydrocortisone ester, or pharmaceutically acceptable salts of thereof, and/or an antioxidant, is equal to or less than, or no more than 10 g, 9.5 g, 9.0 g, 8.5 g, 8.0 g, 7.5 g, 7.0 g, 6.5 g, 6.0 g, 5.5 g, 5.0 g, 4.5 g, 4.0 g, 3.5 g, 3.0 g, 2.5 g, 2.0 g, 1.5 g, 1.0 g, 0.95 g, 0.9 g, 0.85 g, 0.8 g, 0.75 g, 0.7 g, 0.65 g, 0.6 g, 0.55 g, 0.5 g, 0.45 g, 0.4 g, 0.35 g, 0.3 g, 0.25 g, 0.2 g, 0.15 g, 0.1 g, 0.09 g, 0.08 g, 0.07 g, 0.06 g, 0.05 g, 0.04 g, 0.03 g, 0.02 g, 0.01 g, 0.009 g, 0.008 g, 0.007 g, 0.006 g, 0.005 g, 0.004 g, 0.003 g, 0.002 g, 0.001 g, 0.0009 g, 0.0008 g, 0.0007 g, 0.0006 g, 0.0005 g, 0.0004 g, 0.0003 g, 0.0002 g, or 0.0001 g in a pharmaceutical formulation described herein.

In some embodiments, the amount of each of the active and/or inactive pharmaceutical ingredients provided in the pharmaceutical compositions of the invention, such as a hydrocortisone, hydrocortisone prodrug, i.e., hydrocortisone ester, or pharmaceutically acceptable salts of thereof, and/or an antioxidant, is more than 0.0001 g, 0.0002 g, 0.0003 g, 0.0004 g, 0.0005 g, 0.0006 g, 0.0007 g, 0.0008 g, 0.0009 g, 0.001 g, 0.0015 g, 0.002 g, 0.0025 g, 0.003 g, 0.0035 g, 0.004 g, 0.0045 g, 0.005 g, 0.0055 g, 0.006 g, 0.0065 g, 0.007 g, 0.0075 g, 0.008 g, 0.0085 g, 0.009 g, 0.0095 g, 0.01 g, 0.015 g, 0.02 g, 0.025 g, 0.03 g, 0.035 g, 0.04 g, 0.045 g, 0.05 g, 0.055 g, 0.06 g, 0.065 g, 0.07 g, 0.075 g, 0.08 g, 0.085 g, 0.09 g, 0.095 g, 0.1 g, 0.15 g, 0.2 g, 0.25 g, 0.3 g, 0.35 g, 0.4 g, 0.45 g, 0.5 g, 0.55 g, 0.6 g, 0.65 g, 0.7 g, 0.75 g, 0.8 g, 0.85 g, 0.9 g, 0.95 g, 1 g, 1.5 g, 2 g, 2.5 g, 3 g, 3.5, 4 g, 4.5 g, 5 g, 5.5 g, 6 g, 6.5 g, 7 g, 7.5 g, 8 g, 8.5 g, 9 g, 9.5 g, or 10 g in a pharmaceutical formulation described herein.

Each of the active pharmaceutical ingredients according to the invention is effective over a wide dosage range. For example, in the treatment of adult humans, dosages independently range from 0.01 to 1000 mg, from 0.5 to 100 mg, from 1 to 50 mg per day, and from 5 to 40 mg per day are examples of dosages that may be used. Effective dosages from 50 to 200 mg per week are also examples of dosages that may be used. In one embodiment, the effective weekly dosage is about 50 mg. In one embodiment, the effective weekly dosage is about 100 mg. In one embodiment, the effective weekly dosage is about 150 mg. In one embodiment, the effective weekly dosage is about 200 mg. In one embodiment, the effective weekly dosage is about 250 mg.

The exact dosage will depend upon the route of administration, the form in which the compound is administered, the gender and age of the subject to be treated, the body weight of the subject to be treated, and the preference and experience of the attending physician. The clinically-established dosages of hydrocortisone, hydrocortisone prodrug, i.e., hydrocortisone ester, or pharmaceutically acceptable salts of thereof, for example hydrocortisone phosphate, may also be used if appropriate.

In some embodiments, the concentration of hydrocortisone sodium phosphate ranges from 50 mg/mL to 200 mg/mL. In some embodiments, the concentration of BHT ranges from 0.01% to 0.1%. In some embodiments, the concentration of monothioglycerol ranges from 0.1 mg/mL to 10 mg/mL.

Pharmaceutical Compositions for Injection

In some embodiments, a pharmaceutical composition is provided for injection containing an active pharmaceutical ingredient or combination of active pharmaceutical ingredients, such as a hydrocortisone ester, for example hydrocortisone sodium phosphate, and a pharmaceutical excipient suitable for injection.

The forms in which the compositions of the present invention may be incorporated for administration by injection include aqueous or oil suspensions, or emulsions, with sesame oil, corn oil, cottonseed oil, or peanut oil, as well as elixirs, mannitol, dextrose, or a sterile aqueous solution, and similar pharmaceutical vehicles.

Aqueous solutions in saline are also conventionally used for injection. Ethanol, glycerol, propylene glycol and liquid polyethylene glycol (and suitable mixtures thereof), cyclodextrin derivatives, and vegetable oils may also be employed. The proper fluidity can be maintained, for example, by the use of a coating, such as lecithin, for the maintenance of the required particle size in the case of dispersion and by the use of surfactants. The prevention of the action of microorganisms can be brought about by various antibacterial and antifungal preservatives or preservative agents, for example, parabens, chlorobutanol, phenol, sorbic acid, and thimerosal.

Sterile injectable solutions are prepared by incorporating an active pharmaceutical ingredient or combination of active pharmaceutical ingredients in the required amounts in the appropriate solvent with various other ingredients as enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, certain desirable methods of preparation are vacuum-drying and freeze-drying techniques which yield a powder of the active ingredient plus any additional desired ingredient from a previously sterile-filtered solution thereof.

Administration of an active pharmaceutical ingredient or combination of active pharmaceutical ingredients or a pharmaceutical composition thereof can be effected by any method that enables delivery of the compounds to the site of action. These methods include oral routes, intraduodenal routes, parenteral injection (including intravenous, intraarterial, subcutaneous, intramuscular, intradermal, intravascular, intraperitoneal or infusion), topical (e.g., transdermal application), rectal administration, via local delivery by catheter or stent or through inhalation. The active pharmaceutical ingredient or combination of active pharmaceutical ingredients can also be administered intraadiposally or intrathecally.

An injector may be used to inject the pharmaceutical formulation described herein. The formulation may be injected subcutaneously or intramuscularly. In some embodiments, the injector is a single use device that is discarded or recycled after administering a single dose. In other embodiments, the injector is a multi-dose injector. Some injectors that are contemplated for use with the formulation described herein are disclosed in U.S. Pat. Nos. 8,021,335; 8,814,834; 8,945,063; and 10,300,207, all incorporated herein by reference.

Referring to FIGS. 5-11, there is shown an injector, generally designated 30, in accordance with an exemplary embodiment of the present invention. Injector 30 may be an auto-injector. Injector 30 may include a housing 32. An end cap 34 may be coupled to housing 30. Injector 30 may include a needle 74 fluidly coupled to a formulation container 72 (e.g., syringe). A plunger 70 may be movable relative to formulation container 72 to force formulation out of needle 74 during an injection. A ram 58 may be operatively associated with plunger 70 such that axial movement of ram 58 causes movement of plunger 70. An energy source 66 (e.g., biasing element, spring) may move plunger 70 when injector 30 is triggered.

Figure 8:
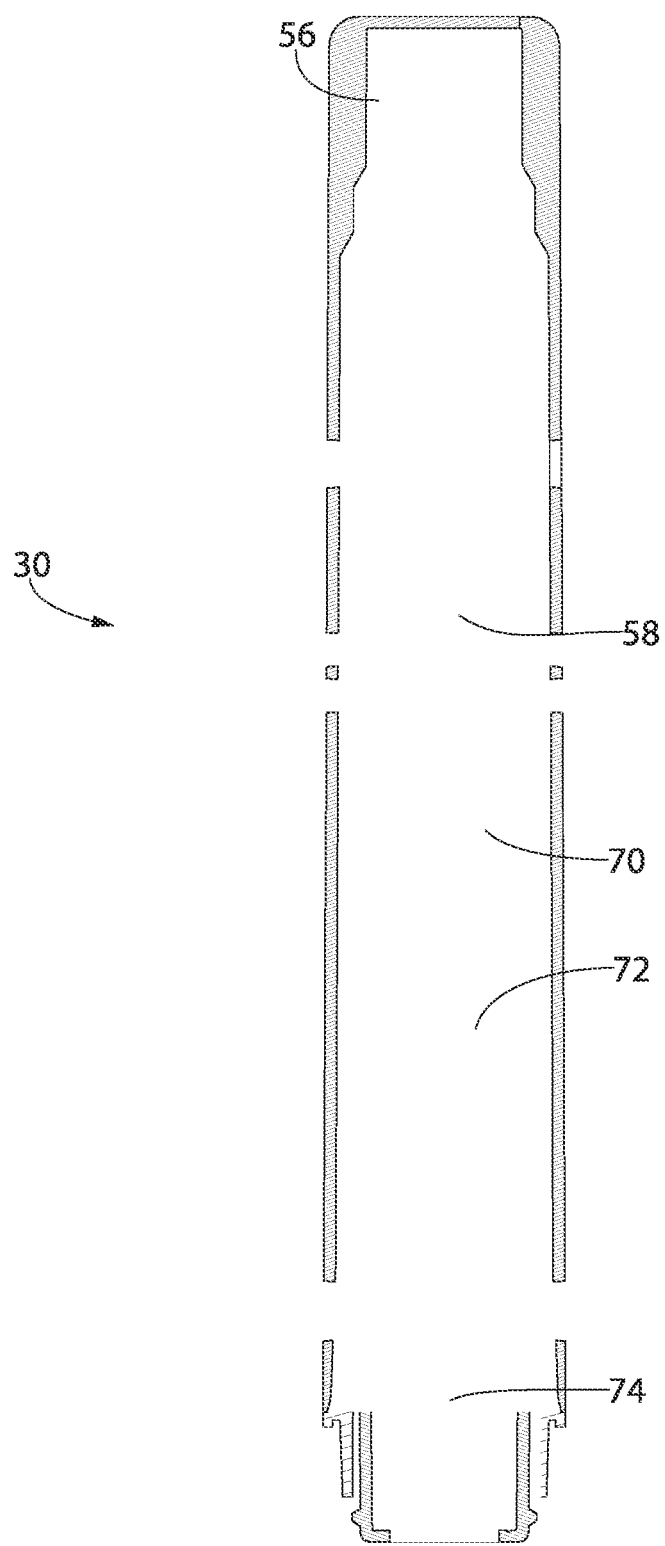
FIG. 8 is a sectional view of the injector of FIG. 6 with the needle guard in a retracted position.

A needle guard 78 may be movably coupled to housing 32. Needle guard 78 may be moveable between an extended position (FIG. 7) and a retracted position (FIG. 8). Needle guard 78 may be movable when a distal end of needle guard 78 is pressed against an injection site. Movement of needle guard 78 relative to housing 32 may trigger injector 30 to start an injection sequence.

Figure 9:
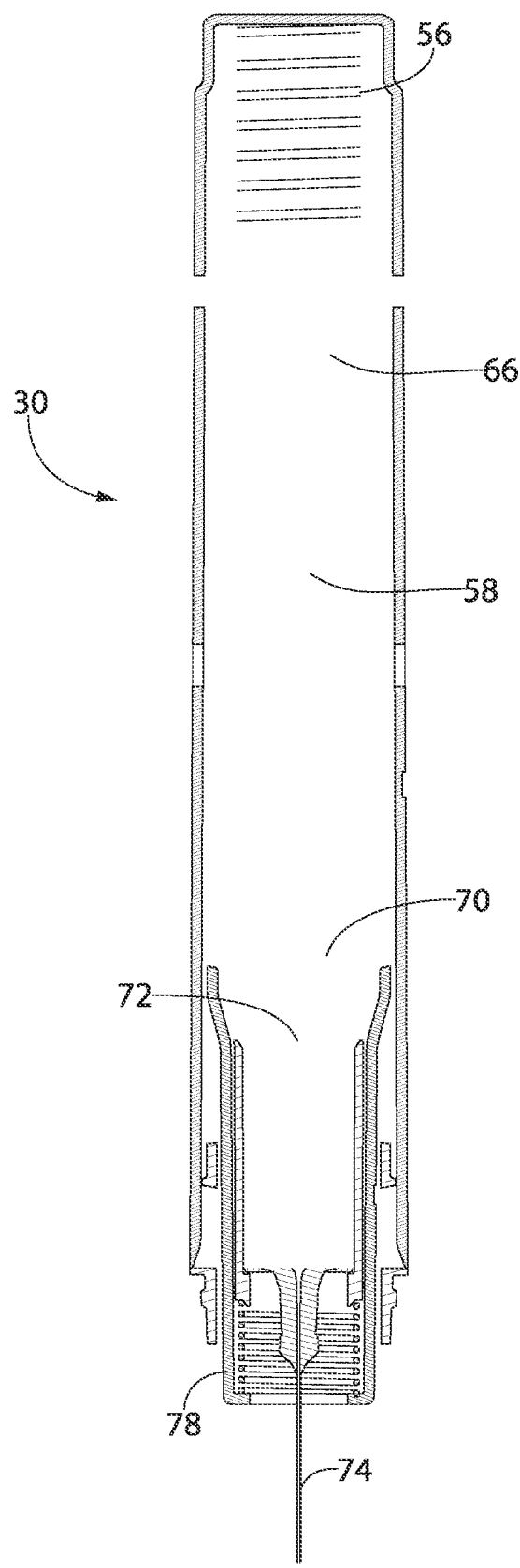
FIG. 9 is a sectional view of the injector of FIG. 6 with the medicament container in an injection position.
Figure 10:
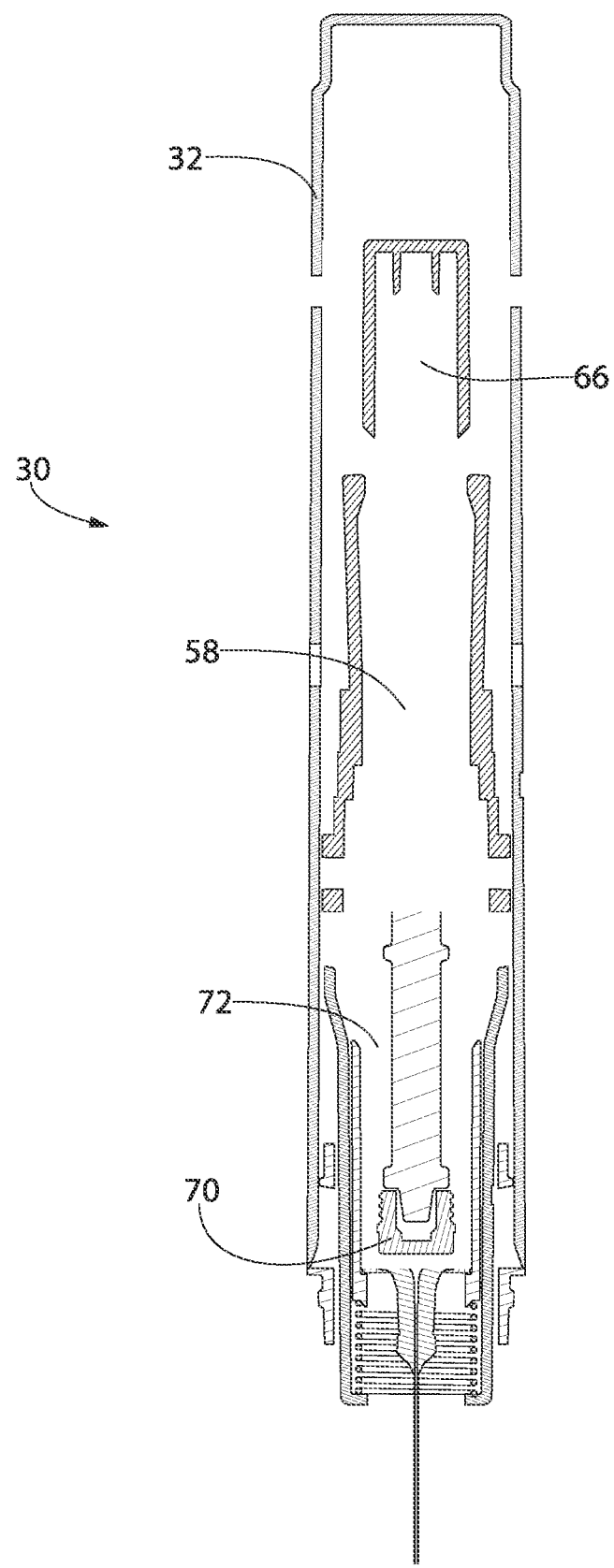
FIG. 10 is a sectional view of the injector of FIG. 6 after medicament has been injected.
Figure 11:
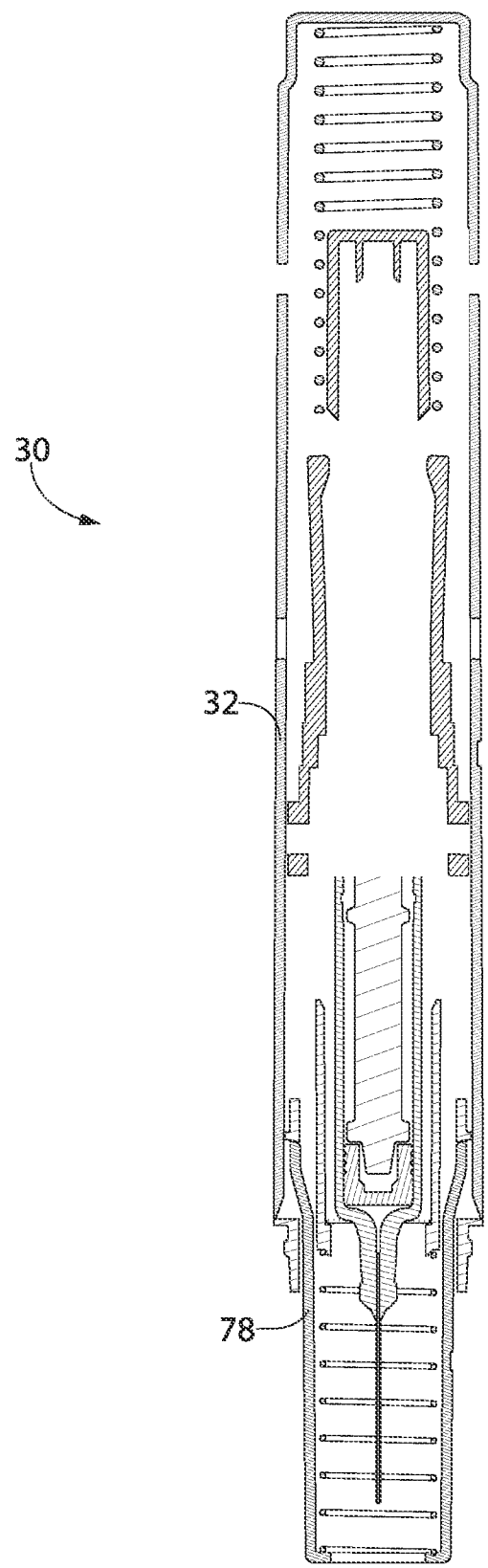
FIG. 11 is a sectional view of the injector of FIG. 6 after an injection with the needle guard in an extended position.

Formulation container 72 may be movable relative to housing 32 between a storage position (FIG. 7) and an injection position (FIG. 9). Formulation container 72 may be moved to the injection position after needle guard 78 triggers injector 30. A second energy source 56 (e.g., biasing element or spring) may move formulation container 72 from the storage position to the injection position. Energy source 66 may move ram 58 once formulation container 72 is in the injection position to dispense the formulation through needle 74. Needle guard 78 may return to the extended position (FIG. 11) once the formulation has been dispensed.

Kits

The invention also provides kits. The kits include an active pharmaceutical ingredient or combination of active pharmaceutical ingredients, either alone or in combination in suitable packaging, and written material that can include instructions for use, discussion of clinical studies and listing of side effects. Such kits may also include information, such as scientific literature references, package insert materials, clinical trial results, and/or summaries of these and the like, which indicate or establish the activities and/or advantages of the composition, and/or which describe dosing, administration, side effects, drug interactions, or other information useful to the health care provider. Such information may be based on the results of various studies, for example, studies using experimental animals involving in vivo models and studies based on human clinical trials. The kit may further contain another active pharmaceutical ingredient. In selected embodiments, an active pharmaceutical ingredient or combination of active pharmaceutical ingredients are provided as separate compositions in separate containers within the kit. In selected embodiments, an active pharmaceutical ingredient or combination of active pharmaceutical ingredients are provided as a single composition within a container in the kit. Suitable packaging and additional articles for use (e.g., measuring cup for liquid preparations, foil wrapping to minimize exposure to air, and the like) are known in the art and may be included in the kit. Kits described herein can be provided, marketed and/or promoted to health providers, including physicians, nurses, pharmacists, formulary officials, and the like. Kits may also, in selected embodiments, be marketed directly to the consumer.

In some embodiments, the invention provides a kit including a composition including a therapeutically effective amount of an active pharmaceutical ingredient (e.g., a hydrocortisone sodium phosphate) or combination of active pharmaceutical ingredients or a pharmaceutically acceptable salt, solvate, hydrate, cocrystal, or prodrug thereof. These compositions are typically pharmaceutical compositions. The kit is for co-administration of the active pharmaceutical ingredient or combination of active pharmaceutical ingredients, either simultaneously or separately.

In some embodiments, the invention provides for a kit including a composition including a therapeutically effective amount of hydrocortisone sodium phosphate alone or in combination with active pharmaceutical ingredients or a pharmaceutically acceptable salt, solvate, hydrate, cocrystal, or prodrug in an oil combined with an antioxidant in a prefilled syringe (PFS) or vial. In some embodiments, the prefilled syringe or the vial are transparent. The kit includes suitable packaging for protecting the prefilled syringe or vial from light. In some embodiments this includes an autoinjector. In other embodiments, this includes an autoinjector with a viewing window to allow inspection of the drug prior to injection. In yet other embodiments, the autoinjector is in a carton to prevent light access to the drug.

The prefilled syringe or the vial may include one dose or multiple doses. In some embodiments, a prefilled syringe or vial including multiple doses is bigger, i.e., has a larger volume than a prefilled syringe or vial including only one dose. In some embodiments, the surface area to the volume ratio of a prefilled syringe or vial gets smaller as the prefilled syringe or vial gets larger in volume.

Such kits may include information, such as scientific literature references, package insert materials, clinical trial results, and/or summaries of these and the like, which indicate or establish the activities and/or advantages of the composition, and/or which describe dosing, administration, side effects, drug interactions, or other information useful to the health care provider and/or the patient. Such information may instruct the user to keep the prefilled syringe or prefilled syringe and autoinjector in a carton to protect the pharmaceutical ingredients from light.

In some embodiments, the invention provides a kit including (1) a composition including a therapeutically effective amount of an active pharmaceutical ingredient (e.g., a hydrocortisone sodium phosphate) or combination of active pharmaceutical ingredients or a pharmaceutically acceptable salt, solvate, hydrate, cocrystal, or prodrug thereof, and (2) a diagnostic test for determining whether a patient is in need of hydrocortisone sodium phosphate administration.

Dosages and Dosing Regimens

The amounts of the pharmaceutical compositions administered using the methods herein, such as the dosages of hydrocortisone sodium phosphate, will be dependent on the subject, e.g., human or mammal being treated, the severity of the disorder or condition, the rate of administration, the disposition of the active pharmaceutical ingredients and the discretion of the prescribing physician. Dosage in the range of 50 to 100 mg per week for administration to a human may be adequate to achieve an effective therapeutic level. At times, dosages of 50 to 100 mg per week over several weeks may be required to achieve the desired therapeutic level. However, an effective dosage is in the range of about 0.001 to about 100 mg per kg body weight per day, such as about 1 to about 35 mg/kg/day, in single or divided doses. For a 70 kg human, this would amount to about 0.05 to 7 g/day, such as about 0.05 to about 2.5 g/day. In some instances, dosage levels below the lower limit of the aforesaid range may be more than adequate, while in other cases still larger doses may be employed without causing any harmful side effect— e.g., by dividing such larger doses into several small doses for administration throughout the day. The dosage of the pharmaceutical compositions and active pharmaceutical ingredients may be provided in units of mg/kg of body mass or in mg/m$^2$ of body surface area.

In some embodiments, a pharmaceutical composition or active pharmaceutical ingredient is administered in multiple doses. In an embodiment, a pharmaceutical composition is administered in multiple doses. Dosing may be once, twice, three times, four times, five times, six times, or more than six times per day. Dosing may be once a month, once every two weeks, once a week, or once every other day. In other embodiments, a pharmaceutical composition is administered about once per day to about 6 times per day. In some embodiments, a pharmaceutical composition is administered once daily, while in other embodiments, a pharmaceutical composition is administered twice daily, and in other embodiments a pharmaceutical composition is administered three times daily.

Administration of the active pharmaceutical ingredients may continue as long as necessary. In selected embodiments, a pharmaceutical composition is administered for more than 1, 2, 3, 4, 5, 6, 7, 14, or 28 day(s). Other embodiments require the pharmaceutical composition is administered for more than 1, 2, 3, 4, 5, 6, 7, 14, or 28 week(s). In some embodiments, a pharmaceutical composition is administered for less than, or no more than 28, 14, 7, 6, 5, 4, 3, 2, or 1 day(s). In some embodiments, a pharmaceutical composition is administered chronically on an ongoing basis—e.g., for the treatment of chronic effects. In some embodiments, the administration of a pharmaceutical composition continues for less than, or no more than about 7 days. In yet another embodiment the administration continues for more than about 6, 10, 14, 28 days, two months, six months, or one year. In some cases, continuous dosing is achieved and maintained as long as necessary.

In some embodiments, an effective dosage of an active pharmaceutical ingredient disclosed herein is in the range of about 1 mg to about 500 mg, about 10 mg to about 300 mg, about 20 mg to about 250 mg, about 25 mg to about 200 mg, about 50 mg to 200 mg, about 10 mg to about 200 mg, about 20 mg to about 150 mg, about 30 mg to about 120 mg, about 10 mg to about 90 mg, about 20 mg to about 80 mg, about 30 mg to about 70 mg, about 40 mg to about 60 mg, about 45 mg to about 55 mg, about 50 mg to about 100 mg, about 48 mg to about 52 mg, about 50 mg to about 150 mg, about 60 mg to about 140 mg, about 70 mg to about 130 mg, about 80 mg to about 120 mg, about 90 mg to about 110 mg, about 95 mg to about 105 mg, about 150 mg to about 250 mg, about 160 mg to about 240 mg, about 170 mg to about 230 mg, about 180 mg to about 220 mg, about 190 mg to about 210 mg, about 195 mg to about 205 mg, or about 198 to about 202 mg. In some embodiments, an effective dosage of an active pharmaceutical ingredient disclosed herein is less than, or no more than about 25 mg, less than, or no more than about 50 mg, less than, or no more than about 75 mg, less than, or no more than about 100 mg, less than, or no more than about 125 mg, less than, or no more than about 150 mg, less than, or no more than about 175 mg, less than, or no more than about 200 mg, less than, or no more than about 225 mg, or less than, or no more than about 250 mg. In some embodiments, an effective dosage of an active pharmaceutical ingredient disclosed herein is greater than about 25 mg, greater than about 50 mg, greater than about 75 mg, greater than about 100 mg, greater than about 125 mg, greater than about 150 mg, greater than about 175 mg, greater than about 200 mg, greater than about 225 mg, or greater than about 250 mg.

In some embodiments, an effective dosage of an active pharmaceutical ingredient disclosed herein is in the range of about 0.01 mg/kg to about 200 mg/kg, or about 0.1 to 100 mg/kg, or about 1 to 50 mg/kg. In some embodiments, an active pharmaceutical ingredient is administered at a dosage of 10 to 200 mg BID, including 50, 60, 70, 80, 90, 100, 150, or 200 mg BID. In some embodiments, an active pharmaceutical ingredient is administered at a dosage of 10 to 500 mg BID, including 1, 5, 10, 15, 25, 50, 75, 100, 150, 200, 300, 400, or 500 mg BID.

In some instances, dosage levels below the lower limit of the aforesaid ranges may be more than adequate, while in other cases still larger doses may be employed without causing any harmful side effect, e.g., by dividing such larger doses into several small doses for administration throughout the day. As those skilled in the art will appreciate, the dosage actually administered will depend upon the condition being treated, the age, health and weight of the recipient, the type of concurrent treatment, if any, and the frequency of treatment. Moreover, the effective dosage amount may be determined by one skilled in the art on the basis of routine empirical activity testing to measure the bioactivity of the compound(s) in a bioassay, and thus establish the appropriate dosage to be administered.

An effective amount of the combination of the active pharmaceutical ingredient may be administered in either single or multiple doses by any of the accepted modes of administration of agents having similar utilities, including rectal, buccal, intranasal and transdermal routes, by intra-arterial injection, intravenously, intraperitoneally, parenterally, intramuscularly, subcutaneously, intradermally, orally, topically, or as an inhalant.

In some embodiments, the compositions described herein further include controlled-release, sustained release, or extended-release therapeutic dosage forms for administration of the compounds described herein, which involves incorporation of the compounds into a suitable delivery system in the formation of certain compositions. This dosage form controls release of the compound(s) in such a manner that an effective concentration of the compound(s) in the bloodstream may be maintained over an extended period of time, with the concentration in the blood remaining relatively constant, to improve therapeutic results and/or minimize side effects. Additionally, a controlled-release system would provide minimum peak to trough fluctuations in blood plasma levels of the compound.

The following clauses describe certain embodiments.

Clause 1. A pharmaceutical formulation comprising hydrocortisone, a hydrocortisone prodrug, and/or a pharmaceutically acceptable salt of any one thereof, and one or more inactive ingredients.

Clause 2. The pharmaceutical formulation of clause 1, wherein the hydrocortisone prodrug is a hydrocortisone ester.

Clause 3. The pharmaceutical formulation of clause 1 or 2, wherein the hydrocortisone prodrug or pharmaceutically acceptable salt thereof is selected from hydrocortisone sodium phosphate, hydrocortisone sodium succinate, hydrocortisone hydrogen succinate, hydrocortisone butyrate, hydrocortisone acetate.

Clause 4. The pharmaceutical formulation of clause 1 or 2, wherein the hydrocortisone prodrug or pharmaceutically acceptable salt thereof is hydrocortisone sodium phosphate.

Clause 5. The pharmaceutical formulation of clause 4, wherein the concentration of hydrocortisone sodium phosphate in the pharmaceutical formulation is between about 5 mg/mL and about 100 mg/mL.

Clause 6. The pharmaceutical formulation of clause 4, wherein the concentration of hydrocortisone sodium phosphate in the pharmaceutical formulation is between about 50 mg/mL and about 100 mg/mL.

Clause 7. The pharmaceutical formulation of clause 4, wherein the concentration of hydrocortisone sodium phosphate in the pharmaceutical formulation is between about 25 mg/mL and about 75 mg/mL.

Clause 8. The pharmaceutical formulation of clause 4, wherein the concentration of hydrocortisone sodium phosphate in the pharmaceutical formulation is about 50 mg/mL, about 51 mg/mL, about 52 mg/mL, about 53 mg/mL, about 54 mg/mL, about 55 mg/mL, about 56 mg/mL, about 57 mg/mL, about 58 mg/mL, about 59 mg/mL, about 60 mg/mL, about 61 mg/mL, about 62 mg/mL, about 63 mg/mL, about 64 mg/mL, about 65 mg/mL, about 66 mg/mL, about 67 mg/mL, about 68 mg/mL, about 69 mg/mL, or about 70 mg/mL.

Clause 9. The pharmaceutical formulation of any one of clauses 1 to 8, wherein the one or more inactive ingredients are selected from a buffer agent, a chelating agent, an antioxidant, a pH adjustor, and a solvent.

Clause 10. The pharmaceutical formulation of clause 9, wherein the buffer agent is selected from monobasic sodium phosphate anhydrous and dibasic sodium phosphate anhydrous.

Clause 11. The pharmaceutical formulation of clause 9, wherein the chelating agent is disodium EDTA.

Clause 12. The pharmaceutical formulation of clause 9, wherein the antioxidant is monothioglycerol.

Clause 13. The pharmaceutical formulation of clause 9, wherein the pH adjustor is selected from sodium hydroxide and HCl.

Clause 14. The pharmaceutical formulation of clause 9, wherein the solvent is water.

Clause 101. An aqueous pharmaceutical formulation comprising from about 50 to about 150 mg/mL hydrocortisone sodium phosphate, from about 2.5 to about 12.5 mg/mL monothioglycerol, and water.

Clause 102. An aqueous pharmaceutical formulation comprising from about 60 to about 135 mg/mL hydrocortisone sodium phosphate, from about 5 to about 10 mg/mL monothioglycerol, and water.

Clause 201. The aqueous pharmaceutical formulation of clause 101 or 102, comprising from about 50 to about 60 mg/mL hydrocortisone sodium phosphate, from about 60 to about 70 mg/mL hydrocortisone sodium phosphate, or from about 70 to about 80 mg/mL hydrocortisone sodium phosphate.

Clause 301. The aqueous pharmaceutical formulation of clause 101 or 102, comprising from about 60 to about 65 mg/mL hydrocortisone sodium phosphate, or from about 65 to about 70 mg/mL hydrocortisone sodium phosphate.

Clause 401. The aqueous pharmaceutical formulation of clauses 101 or 102, comprising from about 120 to about 130 mg/mL hydrocortisone sodium phosphate, from about 130 to about 140 mg/mL hydrocortisone sodium phosphate, or from about 140 to about 150 mg/mL hydrocortisone sodium phosphate.

Clause 501. The aqueous pharmaceutical formulation of clauses 101 or 102, comprising from about 130 to about 135 mg/mL hydrocortisone sodium phosphate, or from about 135 to about 140 mg/mL hydrocortisone sodium phosphate.

Clause 601. The aqueous pharmaceutical formulation of clauses 101 or 102, comprising about 50 mg/mL hydrocortisone sodium phosphate, about 55 mg/mL hydrocortisone sodium phosphate, about 60 mg/mL hydrocortisone sodium phosphate, about 65 mg/mL hydrocortisone sodium phosphate, about 70 mg/mL hydrocortisone sodium phosphate, about 75 mg/mL hydrocortisone sodium phosphate, about 80 mg/mL hydrocortisone sodium phosphate, about 85 mg/mL hydrocortisone sodium phosphate, about 90 mg/mL hydrocortisone sodium phosphate, about 95 mg/mL hydrocortisone sodium phosphate, about 100 mg/mL hydrocortisone sodium phosphate, about 105 mg/mL hydrocortisone sodium phosphate, about 110 mg/mL hydrocortisone sodium phosphate, about 115 mg/mL hydrocortisone sodium phosphate, about 120 mg/mL hydrocortisone sodium phosphate, about 125 mg/mL hydrocortisone sodium phosphate, about 130 mg/mL hydrocortisone sodium phosphate, about 135 mg/mL hydrocortisone sodium phosphate, about 140 mg/mL hydrocortisone sodium phosphate, about 145 mg/mL hydrocortisone sodium phosphate, or about 150 mg/mL hydrocortisone sodium phosphate.

Clause 701. An aqueous pharmaceutical formulation comprising about 60 mg/mL hydrocortisone sodium phosphate, from about 2.5 to about 12.5 mg/mL monothioglycerol, and water.

Clause 702. An aqueous pharmaceutical formulation comprising about 61 mg/mL hydrocortisone sodium phosphate, from about 2.5 to about 12.5 mg/mL monothioglycerol, and water.

Clause 703. An aqueous pharmaceutical formulation comprising about 62 mg/mL hydrocortisone sodium phosphate, from about 2.5 to about 12.5 mg/mL monothioglycerol, and water.

Clause 704. An aqueous pharmaceutical formulation comprising about 63 mg/mL hydrocortisone sodium phosphate, from about 2.5 to about 12.5 mg/mL monothioglycerol, and water.

Clause 705. An aqueous pharmaceutical formulation comprising about 64 mg/mL hydrocortisone sodium phosphate, from about 2.5 to about 12.5 mg/mL monothioglycerol, and water.

Clause 706. An aqueous pharmaceutical formulation comprising about 65 mg/mL hydrocortisone sodium phosphate, from about 2.5 to about 12.5 mg/mL monothioglycerol, and water.

Clause 707. An aqueous pharmaceutical formulation comprising about 66 mg/mL hydrocortisone sodium phosphate, from about 2.5 to about 12.5 mg/mL monothioglycerol, and water.

Clause 708. An aqueous pharmaceutical formulation comprising about 67 mg/mL hydrocortisone sodium phosphate, from about 2.5 to about 12.5 mg/mL monothioglycerol, and water.

Clause 709. An aqueous pharmaceutical formulation comprising about 68 mg/mL hydrocortisone sodium phosphate, from about 2.5 to about 12.5 mg/mL monothioglycerol, and water.

Clause 710. An aqueous pharmaceutical formulation comprising about 69 mg/mL hydrocortisone sodium phosphate, from about 2.5 to about 12.5 mg/mL monothioglycerol, and water.

Clause 711. An aqueous pharmaceutical formulation comprising about 70 mg/mL hydrocortisone sodium phosphate, from about 2.5 to about 12.5 mg/mL monothioglycerol, and water.

Clause 801. An aqueous pharmaceutical formulation comprising about 67 mg/mL hydrocortisone sodium phosphate, from about 2.5 to about 12.5 mg/mL monothioglycerol, and water.

Clause 802. An aqueous pharmaceutical formulation comprising about 67.1 mg/mL hydrocortisone sodium phosphate, from about 2.5 to about 12.5 mg/mL monothioglycerol, and water.

Clause 803. An aqueous pharmaceutical formulation comprising about 67.2 mg/mL hydrocortisone sodium phosphate, from about 2.5 to about 12.5 mg/mL monothioglycerol, and water.

Clause 804. An aqueous pharmaceutical formulation comprising about 67.3 mg/mL hydrocortisone sodium phosphate, from about 2.5 to about 12.5 mg/mL monothioglycerol, and water.

Clause 805. An aqueous pharmaceutical formulation comprising about 67.4 mg/mL hydrocortisone sodium phosphate, from about 2.5 to about 12.5 mg/mL monothioglycerol, and water.

Clause 806. An aqueous pharmaceutical formulation comprising about 67.5 mg/mL hydrocortisone sodium phosphate, from about 2.5 to about 12.5 mg/mL monothioglycerol, and water.

Clause 807. An aqueous pharmaceutical formulation comprising about 67.6 mg/mL hydrocortisone sodium phosphate, from about 2.5 to about 12.5 mg/mL monothioglycerol, and water.

Clause 808. An aqueous pharmaceutical formulation comprising about 67.7 mg/mL hydrocortisone sodium phosphate, from about 2.5 to about 12.5 mg/mL monothioglycerol, and water.

Clause 809. An aqueous pharmaceutical formulation comprising about 67.8 mg/mL hydrocortisone sodium phosphate, from about 2.5 to about 12.5 mg/mL monothioglycerol, and water.

Clause 810. An aqueous pharmaceutical formulation comprising about 67.9 mg/mL hydrocortisone sodium phosphate, from about 2.5 to about 12.5 mg/mL monothioglycerol, and water.

Clause 811. An aqueous pharmaceutical formulation comprising about 68 mg/mL hydrocortisone sodium phosphate, from about 2.5 to about 12.5 mg/mL monothioglycerol, and water.

Clause 901. An aqueous pharmaceutical formulation comprising about 130 mg/mL hydrocortisone sodium phosphate, from about 2.5 to about 12.5 mg/mL monothioglycerol, and water.

Clause 902. An aqueous pharmaceutical formulation comprising about 131 mg/mL hydrocortisone sodium phosphate, from about 2.5 to about 12.5 mg/mL monothioglycerol, and water.

Clause 903. An aqueous pharmaceutical formulation comprising about 132 mg/mL hydrocortisone sodium phosphate, from about 2.5 to about 12.5 mg/mL monothioglycerol, and water.

Clause 904. An aqueous pharmaceutical formulation comprising about 133 mg/mL hydrocortisone sodium phosphate, from about 2.5 to about 12.5 mg/mL monothioglycerol, and water.

Clause 905. An aqueous pharmaceutical formulation comprising about 134 mg/mL hydrocortisone sodium phosphate, from about 2.5 to about 12.5 mg/mL monothioglycerol, and water.

Clause 906. An aqueous pharmaceutical formulation comprising about 135 mg/mL hydrocortisone sodium phosphate, from about 2.5 to about 12.5 mg/mL monothioglycerol, and water.

Clause 907. An aqueous pharmaceutical formulation comprising about 136 mg/mL hydrocortisone sodium phosphate, from about 2.5 to about 12.5 mg/mL monothioglycerol, and water.

Clause 908. An aqueous pharmaceutical formulation comprising about 137 mg/mL hydrocortisone sodium phosphate, from about 2.5 to about 12.5 mg/mL monothioglycerol, and water.

Clause 909. An aqueous pharmaceutical formulation comprising about 138 mg/mL hydrocortisone sodium phosphate, from about 2.5 to about 12.5 mg/mL monothioglycerol, and water.

Clause 910. An aqueous pharmaceutical formulation comprising about 139 mg/mL hydrocortisone sodium phosphate, from about 2.5 to about 12.5 mg/mL monothioglycerol, and water.

Clause 911. An aqueous pharmaceutical formulation comprising about 140 mg/mL hydrocortisone sodium phosphate, from about 2.5 to about 12.5 mg/mL monothioglycerol, and water.

Clause 1001. An aqueous pharmaceutical formulation comprising about 134 mg/mL hydrocortisone sodium phosphate, about 134.1 mg/mL hydrocortisone sodium phosphate, about 134.2 mg/mL hydrocortisone sodium phosphate, about 134.3 mg/mL hydrocortisone sodium phosphate, about 134.4 mg/mL hydrocortisone sodium phosphate, about 134.5 mg/mL hydrocortisone sodium phosphate, about 134.6 mg/mL hydrocortisone sodium phosphate, about 134.7 mg/mL hydrocortisone sodium phosphate, about 134.8 mg/mL hydrocortisone sodium phosphate, about 134.9 mg/mL hydrocortisone sodium phosphate, or about 135 mg/mL hydrocortisone sodium phosphate, from about 2.5 to about 12.5 mg/mL monothioglycerol, and water.

Clause 1101. The aqueous pharmaceutical formulation of any one of clauses 101 to 1001, comprising from about 2.5 to about 3.5 mg/mL monothioglycerol, from about 3.5 to about 4.5 mg/mL monothioglycerol, from about 4.5 to about 5.5 mg/mL monothioglycerol, from about 5.5 to about 6.5 mg/mL monothioglycerol, from about 6.5 to about 7.5 mg/mL monothioglycerol, from about 7.5 to about 8.5 mg/mL monothioglycerol, from about 8.5 to about 9.5 mg/mL monothioglycerol, from about 9.5 to about 10.5 mg/mL monothioglycerol, from about 10.5 to about 11.5 mg/mL monothioglycerol, or from about 11.5 to about 12.5 mg/mL monothioglycerol.

Clause 1201. The aqueous pharmaceutical formulation of any one of clauses 101 to 1001, comprising from about 4 to about 4.25 mg/mL monothioglycerol, from about 4.25 to about 4.5 mg/mL monothioglycerol, from about 4.5 to about 4.75 mg/mL monothioglycerol, from about 4.75 to about 5 mg/mL monothioglycerol, from about 5 to about 5.25 mg/mL monothioglycerol, from about 5.25 to about 5.5 mg/mL monothioglycerol, from about 5.5 to about 5.75 mg/mL monothioglycerol, or from about 5.75 to about 6 mg/mL monothioglycerol.

Clause 1301. The aqueous pharmaceutical formulation of any one of clauses 101 to 1001, comprising from about 9 to about 9.25 mg/mL monothioglycerol, from about 9.25 to about 9.5 mg/mL monothioglycerol, from about 9.5 to about 9.75 mg/mL monothioglycerol, from about 9.75 to about 10 mg/mL monothioglycerol, from about 10 to about 10.25 mg/mL monothioglycerol, from about 10.25 to about 10.5 mg/mL monothioglycerol, from about 10.5 to about 10.75 mg/mL monothioglycerol, or from about 10.75 to about 11 mg/mL monothioglycerol.

Clause 1401. The aqueous pharmaceutical formulation of any one of clauses 101 to 1001, comprising about 4.5 mg/mL monothioglycerol.

Clause 1402. The aqueous pharmaceutical formulation of any one of clauses 101 to 1001, comprising about 4.6 mg/mL monothioglycerol.

Clause 1403. The aqueous pharmaceutical formulation of any one of clauses 101 to 1001, comprising about 4.7 mg/mL monothioglycerol.

Clause 1404. The aqueous pharmaceutical formulation of any one of clauses 101 to 1001, comprising about 4.8 mg/mL monothioglycerol.

Clause 1405. The aqueous pharmaceutical formulation of any one of clauses 101 to 1001, comprising about 4.9 mg/mL monothioglycerol.

Clause 1406. The aqueous pharmaceutical formulation of any one of clauses 101 to 1001, comprising about 5 mg/mL monothioglycerol.

Clause 1407. The aqueous pharmaceutical formulation of any one of clauses 101 to 1001, comprising about 5.1 mg/mL monothioglycerol.

Clause 1408. The aqueous pharmaceutical formulation of any one of clauses 101 to 1001, comprising about 5.2 mg/mL monothioglycerol.

Clause 1409. The aqueous pharmaceutical formulation of any one of clauses 101 to 1001, comprising about 5.3 mg/mL monothioglycerol.

Clause 1410. The aqueous pharmaceutical formulation of any one of clauses 101 to 1001, comprising about 5.4 mg/mL monothioglycerol.

Clause 1411. The aqueous pharmaceutical formulation of any one of clauses 101 to 1001, comprising about 5.5 mg/mL monothioglycerol.

Clause 1501. The aqueous pharmaceutical formulation of any one of clauses 101 to 1001, comprising about 9.5 mg/mL monothioglycerol.

Clause 1502. The aqueous pharmaceutical formulation of any one of clauses 101 to 1001, comprising about 9.6 mg/mL monothioglycerol.

Clause 1503. The aqueous pharmaceutical formulation of any one of clauses 101 to 1001, comprising about 9.7 mg/mL monothioglycerol.

Clause 1504. The aqueous pharmaceutical formulation of any one of clauses 101 to 1001, comprising about 9.8 mg/mL monothioglycerol.

Clause 1505. The aqueous pharmaceutical formulation of any one of clauses 101 to 1001, comprising about 9.9 mg/mL monothioglycerol.

Clause 1506. The aqueous pharmaceutical formulation of any one of clauses 101 to 1001, comprising about 10 mg/mL monothioglycerol.

Clause 1601. The aqueous pharmaceutical formulation of any one of clauses 101 to 1001, comprising about 10.1 mg/mL monothioglycerol.

Clause 1602. The aqueous pharmaceutical formulation of any one of clauses 101 to 1001, comprising about 10.2 mg/mL monothioglycerol.

Clause 1603. The aqueous pharmaceutical formulation of any one of clauses 101 to 1001, comprising about 10.3 mg/mL monothioglycerol.

Clause 1604. The aqueous pharmaceutical formulation of any one of clauses 101 to 1001, comprising about 10.4 mg/mL monothioglycerol.

Clause 1605. The aqueous pharmaceutical formulation of any one of clauses 101 to 1001, comprising about 10.5 mg/mL monothioglycerol.

Clause 1701. The aqueous pharmaceutical formulation of any one of clauses 101 to 1606, further comprising from about 0.5 to about 2.5 mg/mL monobasic sodium phosphate.

Clause 1702. The aqueous pharmaceutical formulation of any one of clauses 101 to 1606, further comprising about 0.5 mg/mL monobasic sodium phosphate.

Clause 1703. The aqueous pharmaceutical formulation of any one of clauses 101 to 1606, further comprising about 0.6 mg/mL monobasic sodium phosphate.

Clause 1704. The aqueous pharmaceutical formulation of any one of clauses 101 to 1606, further comprising about 0.7 mg/mL monobasic sodium phosphate.

Clause 1705. The aqueous pharmaceutical formulation of any one of clauses 101 to 1606, further comprising about 0.8 mg/mL monobasic sodium phosphate.

Clause 1706. The aqueous pharmaceutical formulation of any one of clauses 101 to 1606, further comprising about 0.9 mg/mL monobasic sodium phosphate.

Clause 1707. The aqueous pharmaceutical formulation of any one of clauses 101 to 1606, further comprising about 1 mg/mL monobasic sodium phosphate.

Clause 1708. The aqueous pharmaceutical formulation of any one of clauses 101 to 1606, further comprising about 1.1 mg/mL monobasic sodium phosphate.

Clause 1709. The aqueous pharmaceutical formulation of any one of clauses 101 to 1606, further comprising about 1.2 mg/mL monobasic sodium phosphate.

Clause 1710. The aqueous pharmaceutical formulation of any one of clauses 101 to 1606, further comprising about 1.3 mg/mL monobasic sodium phosphate.

Clause 1711. The aqueous pharmaceutical formulation of any one of clauses 101 to 1606, further comprising about 1.4 mg/mL monobasic sodium phosphate.

Clause 1712. The aqueous pharmaceutical formulation of any one of clauses 101 to 1606, further comprising about 1.5 mg/mL monobasic sodium phosphate.

Clause 1713. The aqueous pharmaceutical formulation of any one of clauses 101 to 1606, further comprising about 1.6 mg/mL monobasic sodium phosphate.

Clause 1714. The aqueous pharmaceutical formulation of any one of clauses 101 to 1606, further comprising about 1.7 mg/mL monobasic sodium phosphate.

Clause 1715. The aqueous pharmaceutical formulation of any one of clauses 101 to 1606, further comprising about 1.8 mg/mL monobasic sodium phosphate.

Clause 1716. The aqueous pharmaceutical formulation of any one of clauses 101 to 1606, further comprising about 1.9 mg/mL monobasic sodium phosphate.

Clause 1717. The aqueous pharmaceutical formulation of any one of clauses 101 to 1606, further comprising about 2 mg/mL monobasic sodium phosphate.

Clause 1718. The aqueous pharmaceutical formulation of any one of clauses 101 to 1606, further comprising about 2.1 mg/mL monobasic sodium phosphate.

Clause 1719. The aqueous pharmaceutical formulation of any one of clauses 101 to 1606, further comprising about 2.2 mg/mL monobasic sodium phosphate.

Clause 1720. The aqueous pharmaceutical formulation of any one of clauses 101 to 1606, further comprising about 2.3 mg/mL monobasic sodium phosphate.

Clause 1721. The aqueous pharmaceutical formulation of any one of clauses 101 to 1606, further comprising about 2.4 mg/mL monobasic sodium phosphate.

Clause 1722. The aqueous pharmaceutical formulation of any one of clauses 101 to 1606, further comprising about 2.5 mg/mL monobasic sodium phosphate.

Clause 1801. The aqueous pharmaceutical formulation of any one of clauses 101 to 1722, further comprising from about 5 to about 25 mg/mL dibasic sodium phosphate.

Clause 1802. The aqueous pharmaceutical formulation of any one of clauses 101 to 1722, further comprising about 5 mg/mL dibasic sodium phosphate.

Clause 1803. The aqueous pharmaceutical formulation of any one of clauses 101 to 1722, further comprising about 6 mg/mL dibasic sodium phosphate.

Clause 1804. The aqueous pharmaceutical formulation of any one of clauses 101 to 1722, further comprising about 7 mg/mL dibasic sodium phosphate.

Clause 1805. The aqueous pharmaceutical formulation of any one of clauses 101 to 1722, further comprising about 8 mg/mL dibasic sodium phosphate.

Clause 1806. The aqueous pharmaceutical formulation of any one of clauses 101 to 1722, further comprising about 9 mg/mL dibasic sodium phosphate.

Clause 1807. The aqueous pharmaceutical formulation of any one of clauses 101 to 1722, further comprising about 10 mg/mL dibasic sodium phosphate.

Clause 1808. The aqueous pharmaceutical formulation of any one of clauses 101 to 1722, further comprising about 11 mg/mL dibasic sodium phosphate.

Clause 1809. The aqueous pharmaceutical formulation of any one of clauses 101 to 1722, further comprising about 12 mg/mL dibasic sodium phosphate.

Clause 1810. The aqueous pharmaceutical formulation of any one of clauses 101 to 1722, further comprising about 13 mg/mL dibasic sodium phosphate.

Clause 1811. The aqueous pharmaceutical formulation of any one of clauses 101 to 1722, further comprising about 14 mg/mL dibasic sodium phosphate.

Clause 1812. The aqueous pharmaceutical formulation of any one of clauses 101 to 1722, further comprising about 15 mg/mL dibasic sodium phosphate.

Clause 1813. The aqueous pharmaceutical formulation of any one of clauses 101 to 1722, further comprising about 16 mg/mL dibasic sodium phosphate.

Clause 1814. The aqueous pharmaceutical formulation of any one of clauses 101 to 1722, further comprising about 17 mg/mL dibasic sodium phosphate.

Clause 1815. The aqueous pharmaceutical formulation of any one of clauses 101 to 1722, further comprising about 18 mg/mL dibasic sodium phosphate.

Clause 1816. The aqueous pharmaceutical formulation of any one of clauses 101 to 1722, further comprising about 19 mg/mL dibasic sodium phosphate.

Clause 1817. The aqueous pharmaceutical formulation of any one of clauses 101 to 1722, further comprising about 20 mg/mL dibasic sodium phosphate.

Clause 1818. The aqueous pharmaceutical formulation of any one of clauses 101 to 1722, further comprising about 21 mg/mL dibasic sodium phosphate.

Clause 1819. The aqueous pharmaceutical formulation of any one of clauses 101 to 1722, further comprising about 22 mg/mL dibasic sodium phosphate.

Clause 1820. The aqueous pharmaceutical formulation of any one of clauses 101 to 1722, further comprising about 23 mg/mL dibasic sodium phosphate.

Clause 1821. The aqueous pharmaceutical formulation of any one of clauses 101 to 1722, further comprising about 24 mg/mL dibasic sodium phosphate.

Clause 1822. The aqueous pharmaceutical formulation of any one of clauses 101 to 1722, further comprising about 25 mg/mL dibasic sodium phosphate.

Clause 1901. The aqueous pharmaceutical formulation of any one of clauses 101 to 1822, further comprising from about 0.1 to about 1 mg/mL disodium EDTA.

Clause 1902. The aqueous pharmaceutical formulation of any one of clauses 101 to 1822, further comprising about 0.1 mg/mL disodium EDTA.

Clause 1903. The aqueous pharmaceutical formulation of any one of clauses 101 to 1822, further comprising about 0.2 mg/mL disodium EDTA.

Clause 1904. The aqueous pharmaceutical formulation of any one of clauses 101 to 1822, further comprising about 0.3 mg/mL disodium EDTA.

Clause 1905. The aqueous pharmaceutical formulation of any one of clauses 101 to 1822, further comprising about 0.4 mg/mL disodium EDTA.

Clause 1906. The aqueous pharmaceutical formulation of any one of clauses 101 to 1822, further comprising about 0.5 mg/mL disodium EDTA.

Clause 1907. The aqueous pharmaceutical formulation of any one of clauses 101 to 1822, further comprising about 0.6 mg/mL disodium EDTA.

Clause 1908. The aqueous pharmaceutical formulation of any one of clauses 101 to 1822, further comprising about 0.7 mg/mL disodium EDTA.

Clause 1909. The aqueous pharmaceutical formulation of any one of clauses 101 to 1822, further comprising about 0.8 mg/mL disodium EDTA.

Clause 1910. The aqueous pharmaceutical formulation of any one of clauses 101 to 1822, further comprising about 0.9 mg/mL disodium EDTA.

Clause 1911. The aqueous pharmaceutical formulation of any one of clauses 101 to 1822, further comprising about 1 mg/mL disodium EDTA.

Clause 2001. The aqueous pharmaceutical formulation of any one of clauses 101 to 1911, wherein the pharmaceutical formulation has a pH from about 7.5 to about 9.5.

Clause 2002. The aqueous pharmaceutical formulation of any one of clauses 101 to 1911, wherein the pharmaceutical formulation has a pH from about 7.5 to about 8.

Clause 2003. The aqueous pharmaceutical formulation of any one of clauses 101 to 1911, wherein the pharmaceutical formulation has a pH from about 8 to about 8.5.

Clause 2004. The aqueous pharmaceutical formulation of any one of clauses 101 to 1911, wherein the pharmaceutical formulation has a pH from about 8.5 to about 9.

Clause 2101. The aqueous pharmaceutical formulation of any one of clauses 101 to 1911, wherein the pharmaceutical formulation has a pH of about 7.5.

Clause 2102. The aqueous pharmaceutical formulation of any one of clauses 101 to 1911, wherein the pharmaceutical formulation has a pH of about 7.6.

Clause 2103. The aqueous pharmaceutical formulation of any one of clauses 101 to 1911, wherein the pharmaceutical formulation has a pH of about 7.7.

Clause 2104. The aqueous pharmaceutical formulation of any one of clauses 101 to 1911, wherein the pharmaceutical formulation has a pH of about 7.8.

Clause 2105. The aqueous pharmaceutical formulation of any one of clauses 101 to 1911, wherein the pharmaceutical formulation has a pH of about 7.9.

Clause 2106. The aqueous pharmaceutical formulation of any one of clauses 101 to 1911, wherein the pharmaceutical formulation has a pH of about 8.

Clause 2107. The aqueous pharmaceutical formulation of any one of clauses 101 to 1911, wherein the pharmaceutical formulation has a pH of about 8.1.

Clause 2108. The aqueous pharmaceutical formulation of any one of clauses 101 to 1911, wherein the pharmaceutical formulation has a pH of about 8.2.

Clause 2109. The aqueous pharmaceutical formulation of any one of clauses 101 to 1911, wherein the pharmaceutical formulation has a pH of about 8.3.

Clause 2110. The aqueous pharmaceutical formulation of any one of clauses 101 to 1911, wherein the pharmaceutical formulation has a pH of about 8.4.

Clause 2111. The aqueous pharmaceutical formulation of any one of clauses 101 to 1911, wherein the pharmaceutical formulation has a pH of about 8.5.

Clause 2112. The aqueous pharmaceutical formulation of any one of clauses 101 to 1911, wherein the pharmaceutical formulation has a pH of about 8.6.

Clause 2113. The aqueous pharmaceutical formulation of any one of clauses 101 to 1911, wherein the pharmaceutical formulation has a pH of about 8.7.

Clause 2114. The aqueous pharmaceutical formulation of any one of clauses 101 to 1911, wherein the pharmaceutical formulation has a pH of about, 8.8.

Clause 2115. The aqueous pharmaceutical formulation of any one of clauses 101 to 1911, wherein the pharmaceutical formulation has a pH of about 8.9.

Clause 2116. The aqueous pharmaceutical formulation of any one of clauses 101 to 1911, wherein the pharmaceutical formulation has a pH of about 9.

Clause 2201. The aqueous pharmaceutical formulation of any one of clauses 1 to 2116, wherein the formulation comprises from no impurities to less than, or no more than 0.05% impurities upon formulation.

Clause 2202. The aqueous pharmaceutical formulation of any one of clauses 101 to 2116, wherein the formulation comprises from no impurities to less than, or no more than 0.04% impurities upon formulation.

Clause 2203. The aqueous pharmaceutical formulation of any one of clauses 101 to 2116, wherein the formulation comprises from no impurities to less than, or no more than 0.03% impurities upon formulation.

Clause 2204. The aqueous pharmaceutical formulation of any one of clauses 101 to 2116, wherein the formulation comprises from no impurities to less than, or no more than 0.02% impurities upon formulation.

Clause 2205. The aqueous pharmaceutical formulation of any one of clauses 101 to 2116, wherein the formulation comprises from no impurities to less than, or no more than 0.01% impurities upon formulation.

Clause 2206. The aqueous pharmaceutical formulation of any one of clauses 1 to 2116, wherein the formulation comprises from no impurities to less than, or no more than 0.1% impurities upon formulation.

Clause 2207. The aqueous pharmaceutical formulation of any one of clauses 101 to 2116, wherein the formulation comprises from no impurities to less than, or no more than 0.09% impurities upon formulation.

Clause 2208. The aqueous pharmaceutical formulation of any one of clauses 101 to 2116, wherein the formulation comprises from no impurities to less than, or no more than 0.08% impurities upon formulation.

Clause 2209. The aqueous pharmaceutical formulation of any one of clauses 101 to 2116, wherein the formulation comprises from no impurities to less than, or no more than 0.07% impurities upon formulation.

Clause 2210. The aqueous pharmaceutical formulation of any one of clauses 101 to 2116, wherein the formulation comprises from no impurities to less than, or no more than 0.06% impurities upon formulation.

Clause 2211. The aqueous pharmaceutical formulation of any one of clauses 1 to 2116, wherein the formulation comprises from no impurities to less than, or no more than 0.5% impurities upon formulation.

Clause 2212. The aqueous pharmaceutical formulation of any one of clauses 101 to 2116, wherein the formulation comprises from no impurities to less than, or no more than 0.45% impurities upon formulation.

Clause 2213. The aqueous pharmaceutical formulation of any one of clauses 101 to 2116, wherein the formulation comprises from no impurities to less than, or no more than 0.4% impurities upon formulation.

Clause 2214. The aqueous pharmaceutical formulation of any one of clauses 101 to 2116, wherein the formulation comprises from no impurities to less than, or no more than 0.35% impurities upon formulation.

Clause 2215. The aqueous pharmaceutical formulation of any one of clauses 101 to 2116, wherein the formulation comprises from no impurities to less than, or no more than 0.3% impurities upon formulation.

Clause 2216. The aqueous pharmaceutical formulation of any one of clauses 1 to 2116, wherein the formulation comprises from no impurities to less than, or no more than 0.25% impurities upon formulation.

Clause 2217. The aqueous pharmaceutical formulation of any one of clauses 101 to 2116, wherein the formulation comprises from no impurities to less than, or no more than 0.2% impurities upon formulation.

Clause 2218. The aqueous pharmaceutical formulation of any one of clauses 101 to 2116, wherein the formulation comprises from no impurities to less than, or no more than 0.15% impurities upon formulation.

Clause 2219. The aqueous pharmaceutical formulation of any one of clauses 101 to 2116, wherein the formulation comprises from no impurities to less than, or no more than 0.14% impurities upon formulation.

Clause 2220. The aqueous pharmaceutical formulation of any one of clauses 101 to 2116, wherein the formulation comprises from no impurities to less than, or no more than 0.13%, 0.12%, or 0.11% impurities upon formulation.

Clause 2301. The aqueous pharmaceutical formulation of any one of clauses 101 to 2205, wherein the formulation comprises from no impurities to less than, or no more than 0.07% impurities upon storage at 25° C. for about 3 months.

Clause 2302. The aqueous pharmaceutical formulation of any one of clauses 101 to 2205, wherein the formulation comprises from no impurities to less than, or no more than 0.06% impurities upon storage at 25° C. for about 3 months.

Clause 2303. The aqueous pharmaceutical formulation of any one of clauses 101 to 2205, wherein the formulation comprises from no impurities to less than, or no more than 0.05% impurities upon storage at 25° C. for about 3 months.

Clause 2304. The aqueous pharmaceutical formulation of any one of clauses 101 to 2205, wherein the formulation comprises from no impurities to less than, or no more than 0.04% impurities upon storage at 25° C. for about 3 months.

Clause 2305. The aqueous pharmaceutical formulation of any one of clauses 101 to 2205, wherein the formulation comprises from no impurities to less than, or no more than 0.03% impurities upon storage at 25° C. for about 3 months.

Clause 2306. The aqueous pharmaceutical formulation of any one of clauses 101 to 2205, wherein the formulation comprises from no impurities to less than, or no more than 0.02% impurities upon storage at 25° C. for about 3 months.

Clause 2307. The aqueous pharmaceutical formulation of any one of clauses 101 to 2205, wherein the formulation comprises from no impurities to less than, or no more than 0.01% impurities upon storage at 25° C. for about 3 months.

Clause 2308. The aqueous pharmaceutical formulation of any one of clauses 101 to 2205, wherein the formulation comprises from 0.01% impurities to less than, or no more than 0.07% impurities upon storage at 25° C. for about 3 months.

Clause 2309. The aqueous pharmaceutical formulation of any one of clauses 101 to 2205, wherein the formulation comprises from 0.01% impurities to less than, or no more than 0.06% impurities upon storage at 25° C. for about 3 months.

Clause 2310. The aqueous pharmaceutical formulation of any one of clauses 101 to 2205, wherein the formulation comprises from 0.01% impurities to less than, or no more than 0.05% impurities upon storage at 25° C. for about 3 months.

Clause 2311. The aqueous pharmaceutical formulation of any one of clauses 101 to 2205, wherein the formulation comprises from 0.01% impurities to less than, or no more than 0.04% impurities upon storage at 25° C. for about 3 months.

Clause 2312. The aqueous pharmaceutical formulation of any one of clauses 101 to 2205, wherein the formulation comprises from 0.01% impurities to less than, or no more than 0.03% impurities upon storage at 25° C. for about 3 months.

Clause 2313. The aqueous pharmaceutical formulation of any one of clauses 101 to 2205, wherein the formulation comprises from 0.01% impurities to less than, or no more than 0.02% impurities upon storage at 25° C. for about 3 months.

Clause 2314. The aqueous pharmaceutical formulation of any one of clauses 101 to 2205, wherein the formulation comprises from 0.01% impurities to less than, or no more than 0.1% impurities upon storage at 25° C. for about 3 months.

Clause 2315. The aqueous pharmaceutical formulation of any one of clauses 101 to 2205, wherein the formulation comprises from 0.01% impurities to less than, or no more than 0.15% impurities upon storage at 25° C. for about 3 months.

Clause 2316. The aqueous pharmaceutical formulation of any one of clauses 101 to 2205, wherein the formulation comprises from 0.01% impurities to less than, or no more than 0.2% impurities upon storage at 25° C. for about 3 months.

Clause 2317. The aqueous pharmaceutical formulation of any one of clauses 101 to 2205, wherein the formulation comprises from 0.01% impurities to less than, or no more than 0.25% impurities upon storage at 25° C. for about 3 months.

Clause 2318. The aqueous pharmaceutical formulation of any one of clauses 101 to 2205, wherein the formulation comprises from 0.01% impurities to less than, or no more than 0.3% impurities upon storage at 25° C. for about 3 months.

Clause 2319. The aqueous pharmaceutical formulation of any one of clauses 101 to 2205, wherein the formulation comprises from 0.01% impurities to less than, or no more than 0.35%, 0.4%, or 0.5% impurities upon storage at 25° C. for about 3 months.

Clause 2401. The aqueous pharmaceutical formulation of any one of claims 101 to 2307, wherein the formulation comprises from no impurities to less than, or no more than 0.20% impurities upon storage at 25° C. for about 6 months.

Clause 2402. The aqueous pharmaceutical formulation of any one of claims 101 to 2307, wherein the formulation comprises from no impurities to less than, or no more than 0.19% impurities upon storage at 25° C. for about 6 months.

Clause 2403. The aqueous pharmaceutical formulation of any one of claims 101 to 2307, wherein the formulation comprises from no impurities to less than, or no more than 0.18% impurities upon storage at 25° C. for about 6 months.

Clause 2404. The aqueous pharmaceutical formulation of any one of claims 101 to 2307, wherein the formulation comprises from no impurities to less than, or no more than 0.17% impurities upon storage at 25° C. for about 6 months.

Clause 2405. The aqueous pharmaceutical formulation of any one of claims 101 to 2307, wherein the formulation comprises from no impurities to less than, or no more than 0.16% impurities upon storage at 25° C. for about 6 months.

Clause 2406. The aqueous pharmaceutical formulation of any one of claims 101 to 2307, wherein the formulation comprises from no impurities to less than, or no more than 0.15% impurities upon storage at 25° C. for about 6 months.

Clause 2407. The aqueous pharmaceutical formulation of any one of claims 101 to 2307, wherein the formulation comprises from no impurities to less than, or no more than 0.14% impurities upon storage at 25° C. for about 6 months.

Clause 2408. The aqueous pharmaceutical formulation of any one of claims 101 to 2307, wherein the formulation comprises from no impurities to less than, or no more than 0.13% impurities upon storage at 25° C. for about 6 months.

Clause 2409. The aqueous pharmaceutical formulation of any one of claims 101 to 2307, wherein the formulation comprises from no impurities to less than, or no more than 0.12% impurities upon storage at 25° C. for about 6 months.

Clause 2410. The aqueous pharmaceutical formulation of any one of claims 101 to 2307, wherein the formulation comprises from no impurities to less than, or no more than 0.11% impurities upon storage at 25° C. for about 6 months.

Clause 2411. The aqueous pharmaceutical formulation of any one of claims 101 to 2307, wherein the formulation comprises from no impurities to less than, or no more than 0.10% impurities upon storage at 25° C. for about 6 months.

Clause 2412. The aqueous pharmaceutical formulation of any one of claims 101 to 2307, wherein the formulation comprises from no impurities to less than, or no more than 0.09% impurities upon storage at 25° C. for about 6 months.

Clause 2413. The aqueous pharmaceutical formulation of any one of claims 101 to 2307, wherein the formulation comprises from no impurities to less than, or no more than 0.08% impurities upon storage at 25° C. for about 6 months.

Clause 2414. The aqueous pharmaceutical formulation of any one of claims 101 to 2307, wherein the formulation comprises from no impurities to less than, or no more than 0.07% impurities upon storage at 25° C. for about 6 months.

Clause 2415. The aqueous pharmaceutical formulation of any one of claims 101 to 2307, wherein the formulation comprises from 0.01% impurities to less than, or no more than 0.20% impurities upon storage at 25° C. for about 6 months.

Clause 2416. The aqueous pharmaceutical formulation of any one of claims 101 to 2307, wherein the formulation comprises from 0.01% impurities to less than, or no more than 0.19% impurities upon storage at 25° C. for about 6 months.

Clause 2417. The aqueous pharmaceutical formulation of any one of claims 101 to 2307, wherein the formulation comprises from 0.01% impurities to less than, or no more than 0.18% impurities upon storage at 25° C. for about 6 months.

Clause 2418. The aqueous pharmaceutical formulation of any one of claims 101 to 2307, wherein the formulation comprises from 0.01% impurities to less than, or no more than 0.17% impurities upon storage at 25° C. for about 6 months.

Clause 2419. The aqueous pharmaceutical formulation of any one of claims 101 to 2307, wherein the formulation comprises from 0.01% impurities to less than, or no more than 0.16% impurities upon storage at 25° C. for about 6 months.

Clause 2420. The aqueous pharmaceutical formulation of any one of claims 101 to 2307, wherein the formulation comprises from 0.01% impurities to less than, or no more than 0.15% impurities upon storage at 25° C. for about 6 months.

Clause 2421. The aqueous pharmaceutical formulation of any one of claims 101 to 2307, wherein the formulation comprises from 0.01% impurities to less than, or no more than 0.14% impurities upon storage at 25° C. for about 6 months.

Clause 2422. The aqueous pharmaceutical formulation of any one of claims 101 to 2307, wherein the formulation comprises from 0.01% impurities to less than, or no more than 0.13% impurities upon storage at 25° C. for about 6 months.

Clause 2423. The aqueous pharmaceutical formulation of any one of claims 101 to 2307, wherein the formulation comprises from 0.01% impurities to less than, or no more than 0.12% impurities upon storage at 25° C. for about 6 months.

Clause 2424. The aqueous pharmaceutical formulation of any one of claims 101 to 2307, wherein the formulation comprises from 0.01% impurities to less than, or no more than 0.11% impurities upon storage at 25° C. for about 6 months.

Clause 2425. The aqueous pharmaceutical formulation of any one of claims 101 to 2307, wherein the formulation comprises from 0.01% impurities to less than, or no more than 0.10% impurities upon storage at 25° C. for about 6 months.

Clause 2426. The aqueous pharmaceutical formulation of any one of claims 101 to 2307, wherein the formulation comprises from 0.01% impurities to less than, or no more than 0.09% impurities upon storage at 25° C. for about 6 months.

Clause 2427. The aqueous pharmaceutical formulation of any one of claims 101 to 2307, wherein the formulation comprises from 0.01% impurities to less than, or no more than 0.08% impurities upon storage at 25° C. for about 6 months.

Clause 2428. The aqueous pharmaceutical formulation of any one of claims 101 to 2307, wherein the formulation comprises from 0.01% impurities to less than, or no more than 0.07% impurities upon storage at 25° C. for about 6 months.

Clause 2429. The aqueous pharmaceutical formulation of any one of claims 101 to 2307, wherein the formulation comprises from 0.01% impurities to less than, or no more than 0.25% impurities upon storage at 25° C. for about 6 months.

Clause 2430. The aqueous pharmaceutical formulation of any one of claims 101 to 2307, wherein the formulation comprises from 0.01% impurities to less than, or no more than 0.3% impurities upon storage at 25° C. for about 6 months.

Clause 2431. The aqueous pharmaceutical formulation of any one of claims 101 to 2307, wherein the formulation comprises from 0.01% impurities to less than, or no more than 0.35% impurities upon storage at 25° C. for about 6 months.

Clause 2432. The aqueous pharmaceutical formulation of any one of claims 101 to 2307, wherein the formulation comprises from 0.01% impurities to less than, or no more than 0.4% impurities upon storage at 25° C. for about 6 months.

Clause 2433. The aqueous pharmaceutical formulation of any one of claims 101 to 2307, wherein the formulation comprises from 0.01% impurities to less than, or no more than 0.45% impurities upon storage at 25° C. for about 6 months.

Clause 2434. The aqueous pharmaceutical formulation of any one of claims 101 to 2307, wherein the formulation comprises from 0.01% impurities to less than, or no more than 0.5% impurities upon storage at 25° C. for about 6 months.

Clause 2501. The aqueous pharmaceutical formulation of any one of clauses 101 to 2428, wherein upon storage at 40° C. for about 1 month, the formulation comprises from no impurities to less than, or no more than 0.35% impurities.

Clause 2601. The aqueous pharmaceutical formulation of any one of clauses 101 to 2428, wherein upon storage at 40° C. for about 2 months, the formulation comprises from no impurities to less than, or no more than 0.7% impurities.

Clause 2701. The aqueous pharmaceutical formulation of any one of clauses 101 to 2428, wherein upon storage at 40° C. for about 3 months, the formulation comprises from no impurities to less than, or no more than 1.5% impurities.

Clause 2801. The aqueous pharmaceutical formulation of any one of clauses 101 to 2428, wherein upon storage at 40° C. for about 6 months, the formulation comprises from no impurities to less than, or no more than 2% impurities.

Clause 2901. The aqueous pharmaceutical formulation of any one of clauses 2301 to 2801, wherein impurities concentration is measured upon storage against at least one pharmaceutically acceptable surface selected from a stopper surface, a needle surface, a needle tip cap surface, a needle shield surface, a septa surface, a syringe plunger surface, a glass syringe surface, a plastic syringe surface, (e.g. neoprene, polyisoprene, silicone), an injector surface, a rubber surface, and the like. Any surface may include any material known in the art, for example and without limitation, neoprene, polyisoprene, silicone, and the like.

Clause 3001. The aqueous pharmaceutical formulation of any one of clauses 2201 to 2901, wherein impurities comprise hydrocortisone.

Clause 3002. The aqueous pharmaceutical formulation of any one of clauses 2201 to 2901, wherein impurities consist essentially of hydrocortisone.

Clause 3003. The aqueous pharmaceutical formulation of any one of clauses 2201 to 2901, wherein the formulation comprises from no hydrocortisone to less than, or no more than 0.01% hydrocortisone; from no hydrocortisone to less than, or no more than 0.025% hydrocortisone; from no hydrocortisone to less than, or no more than 0.05% hydrocortisone; from no hydrocortisone to less than, or no more than 0.1% hydrocortisone; from no hydrocortisone to less than, or no more than 0.15% hydrocortisone; from no hydrocortisone to less than, or no more than 0.2% hydrocortisone; from no hydrocortisone to less than, or no more than 0.25% hydrocortisone; from no hydrocortisone to less than, or no more than 0.3% hydrocortisone; from no hydrocortisone to less than, or no more than 0.35% hydrocortisone; from no hydrocortisone to less than, or no more than 0.4% hydrocortisone; from no hydrocortisone to less than, or no more than 0.45% hydrocortisone; or from no hydrocortisone to less than, or no more than 0.5% hydrocortisone.

Clause 3101. The aqueous pharmaceutical formulation of any one of clauses 101 to 3003, wherein any formulation component concentration can be expressed as % w/v, using a conversion factor of 1 mg/mL=0.1% w/v.

Clause 3201. A method of treating a disease, condition, or disorder alleviated by administering hydrocortisone or hydrocortisone sodium phosphate in a patient in need thereof, the method comprising administering to the patient a therapeutically effective amount of the aqueous pharmaceutical formulation of any one of clauses 101 to 3101.

Clause 3301. The method of clause 3201, wherein the disease, condition, or disorder comprises one or more of swollen joints and/or tendons, painful joints and/or tendons, tennis elbow, and/or golfer's elbow.

Clause 3401. The method of clause 3201, wherein the disease, condition, or disorder comprises one or more of asthma, an allergic reaction, severe shock due to injury or infection, and/or or failure of the adrenal glands.

Clause 3501. The method of clause 3201, wherein the disease, condition, or disorder comprises inflammation.

Clause 3601. The method of clause 3201, wherein the disease, condition, or disorder comprises asthma, atopic dermatitis, contact dermatitis, drug hypersensitivity reactions, perennial or seasonal allergic rhinitis, serum sickness, and/or transfusion reactions.

Clause 3701. The method of clause 3201, wherein the disease, condition, or disorder comprises dermatologic diseases selected from bullous dermatitis herpetiformis, exfoliative erythroderma, mycosis fungoides, pemphigus, severe erythema multiforme (Stevens-Johnson syndrome).

Clause 3801. The method of clause 3201, wherein the disease, condition, or disorder comprises endocrine disorders selected from primary or secondary adrenocortical insufficiency, congenital adrenal hyperplasia, hypercalcemia associated with cancer, and/or nonsuppurative thyroiditis.

Clause 3901. The method of clause 3201, wherein the disease, condition, or disorder comprises gastrointestinal diseases.

Clause 4001. The method of clause 3201, wherein the disease, condition, or disorder comprises gastrointestinal diseases selected from regional enteritis (systemic therapy) and ulcerative colitis.

Clause 4101. The method of clause 3201, wherein the disease, condition, or disorder comprises hematologic disorders selected from acquired (autoimmune) hemolytic anemia, congenital (erythroid) hypoplastic anemia (Diamond-Blackfan anemia), idiopathic thrombocytopenic purpura in adults, pure red cell aplasia, selected cases of secondary thrombocytopenia.

Clause 4201. The method of clause 3201, wherein the disease, condition, or disorder comprises one or more of trichinosis with neurologic or myocardial involvement, tuberculous meningitis with subarachnoid block or impending block.

Clause 4301. The method of clause 3201, wherein the disease, condition, or disorder comprises neoplastic diseases.

Clause 4401. The method of clause 3201, wherein the disease, condition, or disorder comprises palliative management of leukemias and/or lymphomas.

Clause 4501. The method of clause 3201, wherein the disease, condition, or disorder comprises nervous system conditions selected from acute exacerbations of multiple sclerosis; cerebral edema associated with primary or metastatic brain tumor, or craniotomy.

Clause 4601. The method of clause 3201, wherein the disease, condition, or disorder comprises ophthalmic diseases selected from sympathetic ophthalmia, uveitis and ocular inflammatory conditions.

Clause 4701. The method of clause 3201, wherein the disease, condition, or disorder comprises renal diseases.

Clause 4801. The method of clause 3201, wherein the disease, condition, or disorder comprises inducing diuresis or remission of proteinuria in idiopathic nephrotic syndrome or that due to lupus erythematosus.

Clause 4901. The method of clause 3201, wherein the disease, condition, or disorder comprises respiratory diseases selected from berylliosis, fulminating or disseminated pulmonary tuberculosis, idiopathic eosinophilic pneumonias, symptomatic sarcoidosis.

Clause 5001. The method of clause 3201, wherein the disease, condition, or disorder comprises rheumatic disorders selected from acute gouty arthritis; acute rheumatic carditis; ankylosing spondylitis; psoriatic arthritis; rheumatoid arthritis, including juvenile rheumatoid arthritis.

Clause 5101. The method of clause 3201, wherein the disease, condition, or disorder comprises dermatomyositis, temporal arteritis, polymyositis, and systemic lupus erythematosus.

Clause 5201. The method of clause 3201, wherein the disease, condition, or disorder comprises adrenal insufficiency selected from primary adrenal insufficiency, acute adrenal insufficiency, and secondary adrenal insufficiency.

A number of patent and non-patent publications are cited herein in order to describe the state of the art to which this invention pertains. The entire disclosure of each of these publications is incorporated by reference herein.

The following examples describe the invention in further detail. These examples are provided for illustrative purposes only, and should in no way be considered as limiting the invention.

EXAMPLES

Example 1

Antioxidants, chelating agent, buffer agents used in the stability study are listed in the following table:
Inactive ingredients used in the formulation development;

Procedure for formulation preparation: add ~90% of water to a container; turn on the mixer; add Monobasic sodium phosphate anhydrous, Dibasic sodium phosphate anhydrous, Disodium EDTA, an antioxidant, or a third stabilizer, use a portion of water to rinse if needed, mix for at least 15 min or until dissolved; weigh hydrocortisone sodium phosphate and charge to the container from previous step, mix for at least 30 min and until dissolved; measure pH, adjust pH to approx. 8.0 using 0.1 N HCl or 0.1 N NaOH; Q.S. to final volume (weight) using water, mix for at least 15 min.

A stability indicating HPLC method was developed, suitable for monitoring hydrolysis of hydrocortisone sodium phosphate and other degradations based on literature methods for hydrocortisone prodrugs and other similar products. A detailed description of the HPLC method with information such as chromatography conditions and sample preparation, described herein. in 5.0 Analytical method development Primary Pack in Materials:

| Material | Description |
| --- | --- |
| Syringe Barrel | Ompi Article #7600007.6977, Syringe EZ-Fill 1 mL Long, 22G 5/8 3B, NS 4800GS, NE160, EB, IUP |
| Stopper | West Stoppers Item # 10149656, Article 2340 4432/50 Gry B2-40 Westar RU |

The pH effect was evaluated for Formulations F #1 to F #4 at 13.42% hydrocortisone sodium phosphate with disodium edetate and sodium formaldehyde included at level typically used in injectable products. The effect of drug concentration on stability was studied in F #5, which has a concentration at 6.71% (50 mg/mL hydrocortisone) in comparison to 13.42% (100 mg/mL hydrocortisone) for the other formulations.

TABLE 1

| Inactive ingredient | Functionality | Quality Standard | Level used in the study | FDA IIG Limit for IM |
| --- | --- | --- | --- | --- |
| Edetate disodium | Chelating agent | USP | 0.02% w/v | 10% w/v |
| Sodium sulfite | Antioxidant | USP | 0.2% w/v | 0.2% w/v |
| Sodium formaldehyde sulfoxylate | Antioxidant | USP-NF | 0.2% w/v | 0.2% w/v |
| Monothioglycerol | Antioxidant | USP-NF | 0.5% w/v | 0.5% w/v |
| Ascorbic acid | Antioxidant | USP | 0.2% w/v | 0.2% w/v |
| Methionine | Antioxidant | USP | 0.05% w/v | 0.05% w/v |
| Niacinamide | Stabilizer | USP | 2.5% w/v | 2.5% w/v |
| Creatinine | Stabilizer | USP | 0.8% w/v | 0.8% w/v |
| Hydroxylpropyl beta cyclodextrin | Stabilizer | USP-NF | 10% w/v | 33.33% w/v |
| Sodium phosphate dibasic | Buffer agent | USP-NF | 0.1-0.8% | 27.8% |
| Sodium phosphate monobasic | Buffer agent | USP-NF | 0.01-0.08% | 2.56% |

Prototype Formulations to Evaluate Off and Concentration:

TABLE 2

| Ingredient | F #1 | F#2 | F#3 | F#4 | F#5 |
|---|---|---|---|---|---|
| Hydrocortisone sodium phosphate (w/v) | 13.42% | 13.42% | 13.42% | 13.42% | 6.71% |
| Monobasic sodium phosphate anhydrous | 0.1% | 0.1% | 0.1% | 0.1% | 0.1% |
| Dibasic sodium phosphate anhydrous | 1.09% | 1.09% | 1.09% | 1.09% | 1.09% |
| Disodium EDTA | 0.02% | 0.02% | 0.02% | 0.02% | 0.02% |
| Sodium formaldehyde sulfoxylate | 0.2% | 0.2% | 0.2% | 0.2% | 0.2% |
| Sodium hydroxide/HCl | q.s. to pH 7.0 | q.s. to pH 7.5 | q.s. to pH 8.0 | q.s. to pH 8.5 | q.s. to pH 8.0 |
| Water | q.s. to 1 mL | q.s. to 1 mL | q.s. to 1 mL | q.s. to 1 mL | q.s. to 1 mL |

A second group of formulations were designed to study alternative antioxidants to sodium formaldehyde sulfoxylate, such as sodium sulfite, monothioglycerol, ascorbic acid, and methionine, whether better stabilization effect can be achieved (F #6-9):

Prototype formulations to evaluate the effect of antioxidants:

TABLE 3

| Ingredient | F #6 | F#7 | F#8 | F#9 |
|---|---|---|---|---|
| Hydrocortisone sodium phosphate | 13.42% | 13.42% | 13.42% | 13.42% |
| Monobasic sodium phosphate anhydrous | 0.1% | 0.1% | 0.1% | 0.1% |
| Dibasic sodium phosphate anhydrous | 1.09% | 1.09% | 1.09% | 1.09% |
| Disodium EDTA | 0.02% | 0.02% | 0.02% | 0.02% |
| Sodium sulfite | 0.2% | | | |
| Monothioglycerol | | 0.5% | | |
| Ascorbic acid | | | 0.2% | |
| Methionine | | | | 0.05% |
| Sodium hydroxide/HCl | q.s to pH 8.0 | q.s to pH 8.0 | q.s to pH 8.0 | q.s to pH 8.0 |
| Water | q.s to 1 mL | q.s to 1 mL | q.s to 1 mL | q.s to 1 mL |

As disclosed by U.S. Pat. No. 2,970,944, incorporated herein in its entirety, the stability of aqueous steroid phosphates including hydrocortisone sodium phosphates can be increased by incorporation of a small amount of a nitrogen containing compound such as niacinamide and creatinine. The main instability for steroid phosphates is the formation of precipitate during storage, which is due to the hydrolysis to form free hydrocortisone with much less aqueous solubility. It is possible that niacinamide and creatinine increase the solubility of hydrocortisone and thus, prevent precipitation after formation from hydrolysis.

The purpose to study Formulation F #10 to F #13 was to evaluate whether solubilizing agents like niacinamide, creatinine, hydroxylpropyl beta cyclodextrin can stabilize hydrocortisone sodium phosphate injection to maintain as clear solutions during stability test.

Prototype Formulations to Evaluate Solubilizing Agents

TABLE 4

| Ingredient | F #10 | F#11 | F#12 | F#13 | F#14 | F#15 |
|---|---|---|---|---|---|---|
| Hydrocortisone sodium phosphate | 13.42% w/v | 13.42% w/v | 13.42% w/v | 13.42% w/v | 13.42% w/v | 13.42% w/v |
| Monobasic sodium phosphate anhydrous | 0.1% w/v | 0.1% w/v | 0.1% w/v | 0.1% w/v | 0.1% w/v | 0.1% w/v |
| Dibasic sodium phosphate anhydrous | 1.09% w/v | 1.09% w/v | 1.09% w/v | 1.09% w/v | 1.09% w/v | 1.09% w/v |
| Disodium EDTA | 0.02% w/v | 0.02% w/v | 0.02% w/v | 0.02% w/v | 0.02% w/v | 0.02% w/v |
| Sodium formaldehyde sulfoxylate | 0.2% w/v | 0.2% w/v | 0.2% w/v | 0.2% w/v | 0.2% w/v | 0.2% w/v |
| Creatinine | 0.8% w/v | | | | | |
| Niacinamide | | 2.5% w/v | | | | |
| Hydroxypropyl beta cyclodextrin | | | 5.0% w/v | 10.0% w/v | | |
| Lactobionic acid | | | | | 0.2% w/v | |
| Sodium hydroxide/HCl | q.s to pH 8.0 | q.s to pH 8.0 | q.s to pH 8.0 | q.s to pH 8.0 | q.s to pH 8.0 | q.s to pH 8.0 |
| Water | q.s to 1 mL | q.s to 1 mL | q.s to 1 mL | q.s to 1 mL | q.s to 1 mL | q.s to 1 mL |

The needle shield in PFS is permeable to oxygen. Without wishing to be bound by any particular theory, it is believed that the use of barrier packaging such as foil pouch has the potential to enhance the stability of hydrocortisone sodium phosphate injection in PFS. The foil pouch to be evaluated is from Glenroy with film structure EFS 477-001. Two sets of formulation F #8 and F #15 PFS were packed with foil pouch purged with nitrogen, one PFS per pouch, while another set were packed the foil pouch with StabilOx oxygen scavenger, one PFS/two packs of oxygen scavenger per pouch, as described herein, to evaluate whether barrier packaging offer any stabilizing effect.

Specification of Glenroy Foil Pouch:
Criteria Details
Product Name Glenroy Foil Pouch
Supplier Item # EFS 477-001
Dimensions Width—3.246-inch, Length—9.75 inch, and Seal—⅜ inch
Material Construction Coated Polyester (PET)—0.48 mm, LDPE white—0.75 mm, Aluminum foil—0.5 mm, HPC—0.75 mm, LLDPE—1.25 mm Details of StabilOx, D 100-H60 Oxygen Absorber Packets:

TABLE 5

| Criteria | Details |
| --- | --- |
| Product Name | StabilOx ®, D-100-H60, is an oxygen absorbing packet in cut strip form. |
| Part Number | 02-02937CG10 |
| DESCRIPTION | StabilOx ®, D-100-H60 oxygen absorbers are designed to absorb a minimum of 100 cc of oxygen for modified atmosphere packaging of dry or semi-moist products with water activity less than 0.7 intended for storage and distribution at ambient or refrigerated temperatures down to 30 degrees F. The rate of absorption is dependent upon the equilibrium relative humidity and the composition of the atmosphere within the package. |
| Physical Attributes | 0.76" wide ± 0 .04" × 1.83" long ± 0.07", The D-100-H60 is active in air and will begin to react within one-half hour after removal of the protective barrier pouch |
| MATERIALS | Product contact surface is Tyvek ® and suitable for direct food contact |

Study of packaging control on stability of HCP injection in PFS:

TABLE 6

| Sublot# | F#-A | F#-B | F#-C |
| --- | --- | --- | --- |
| Formulation | | Formulation F#8 and F#15 | |
| Pouch | None | One PFS, Purging nitrogen, pouching | One PFS, Two oxygen scavengers, Pouching |

All the formulations were prepared together, filled in PFS and were placed on stability. There are different sets of formulations. Formulations for each set were prepared on a separate day, PFS were filled and the zero time analysis was conducted on the next day. Information on actual composition of 15 prototype formulations is described herein.

Stability program for the stability work are defined below:

TABLE 7

| Storage Condition | Intervals | | | | | | | | | Contingency samples |
| --- | --- | --- | --- | --- | --- | --- | --- | --- | --- | --- |
| | Initial | 1 M | 2 M | 3 M | 6 M | 9 M | 12 M | 18 M | 24 M | |
| 25° C. | | | | X | X | (X) | (X) | (X) | (X) | 5 |
| 40° C. | X | X | X | X | X | | — | | — | 2 |

X = Appearance, Color/Clarity, pH, Assay and Related substances (X) The decision to analyze these samples is to be made at 6 M time point Following HPLC method was developed to determine the potency of Hydrocortisone sodium Phosphate and the area % of Hydrocortisone impurity and other unknown impurities in Hydrocortisone sodium Phosphate injection. This method employs High Performance Liquid Chromatography (HPLC) to determine the potency of Hydrocortisone sodium Phosphate and the area % of Hydrocortisone impurity and other unknown impurities in Hydrocortisone sodium Phosphate injection.

Equipment and Materials:
HPLC: Waters Alliance 2695 with Waters 2998 PDA detector; a data handling system with Empower 2 software.
Reagents:
1) Trifluoroacetic acid
2) Distilled water
3) Acetonitrile, HPLC grade
4) Hydrocortisone sodium Phosphate standard (in-house)
5) Hydrocortisone impurity standard (in-house)
Chromatography conditions:
Column: Waters Sunfire C18, 250×4.6 mm, 5 μm
Column temperature: Ambient
Mobile Phase A: 0.2% v/v TFA in water
Mobile Phase B:0.2% v/v TFA in ACN
Diluent: Water: ACN (80:20)
Pump wash & Needle wash: Diluent
Flow Rate: 1.5 mL/min
Injection volume: 10 μL
Run time: 45 minutes
Detection wavelength: 254 nm
Elution technique: Gradient (Linear):

TABLE 8

| Time in Minutes | % Mobile Phase A | % Mobile Phase B |
| --- | --- | --- |
| 0.00 | 85 | 15 |
| 10.00 | 85 | 15 |
| 22.40 | 55 | 45 |
| 38.00 | 30 | 70 |
| 38.10 | 85 | 15 |
| 45.00 | 85 | 15 |

Preparation of Hydrocortisone Sodium Phosphate Standard Solution:
Prepared a 0.5 mg/mL solution of Hydrocortisone Sodium Phosphate using the diluent. Weighed required amount of standard in a clean empty and dry volumetric flask. Added ~80% volume diluent to the flask to dissolve standard. Sonicated, if necessary. Made up volume to the mark using diluent, mixed well and used in analysis. Prepared standards in duplicate.

Preparation of Hydrocortisone Impurity Stock Solution:

Prepared a stock solution of Hydrocortisone impurity using ACN for qualitative purpose.

Preparation of Peak Identification Solution:

Spiked the Hydrocortisone impurity stock solution to one of the two Hydrocortisone Sodium Phosphate standard solutions separately to prepare the Peak Identification solution. Injected this solution in HPLC sequence to find out the peak shape, peak symmetry and actual retention times of Hydrocortisone Sodium Phosphate and Hydrocortisone impurity on Chromatogram. Used this solution for qualitative purpose only.

Preparation of Hydrocortisone Sodium Phosphate Injection Test Solution:

Prepared a test solution of Hydrocortisone Sodium Phosphate injection in diluent. Weighed required amount of formulation equivalent to 0.5 mg/mL of Hydrocortisone Sodium Phosphate in a clean empty and dry volumetric flask. Added ~80% volume diluent to the flask to dissolve formulation. Sonicated, if necessary. Made up volume to the mark using diluent, mixed well and used in analysis. Prepared test solutions for zero time analysis in duplicate.

System Suitability Criteria for Analysis:

1) Accuracy of response between 2 HCP standards should be in 98-102%. The accuracy of response is calculated using following equation:

$$\% \text{ Accuracy of responce} = \left(\frac{\text{Peak area of } Std\,2}{\text{Peak area of } Std\,1}\right) \times \left(\frac{\text{Concentration of } Std\,1}{\text{Concentration of } Std\,2}\right) \times 100$$

2) % relative standard deviation of peak areas for 5 repeated injections of HCP standard should be less than 2%.

3) Chromatogram of blank (Diluent) should be without unwanted peaks or humps.
4) Note the retention times of Hydrocortisone Sodium Phosphate and Hydrocortisone impurity at zero time analysis. These retention times should not change more than 1 minute range (i.e. ±0.5 minutes)

Figure 2:
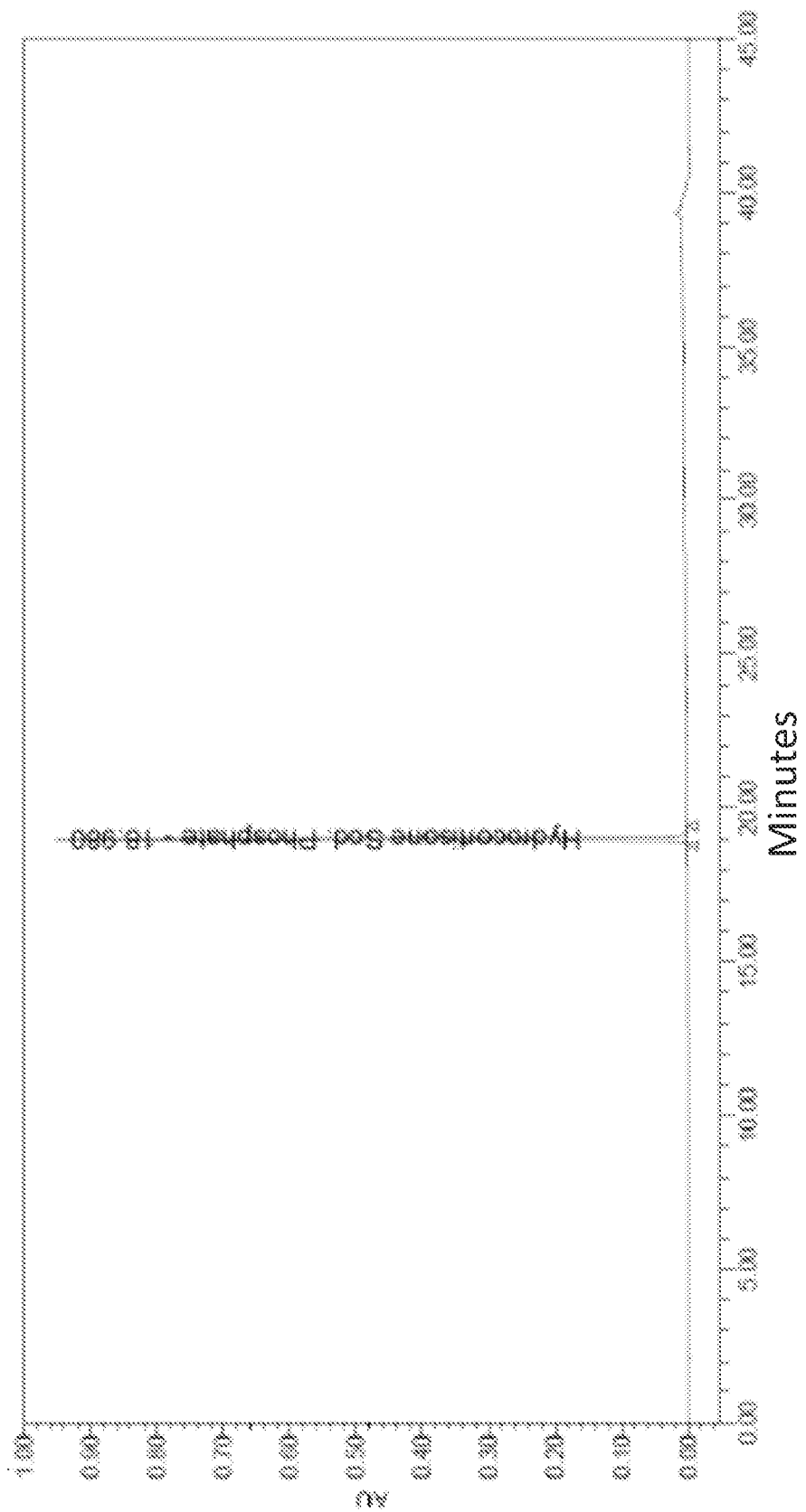
FIG. 2 illustrates a typical chromatogram of HCP using the developed analytical method described herein.

A typical chromatogram of HCP using the developed analytical method is as depicted in FIG. 2.

15 formulations were evaluated under stability study at 40° C. and 25° C. in PFS, to evaluate pH effect, combination of antioxidants, for 6 months. Results from stability data at 40° C. and 25° C.:

Optimum pH range 7.5 to 8.5, in agreement with USP monograph spec

Combinations of EDTA/Monothiolglycerol, EDTA/sulfite show better stability than the combination of EDTA/Rongalite, which is covered by a U.S. Pat. No. 10,456,355, incorporated in its entirety herein The addition of a third stabilizer, creatine significantly improve the stability of formulation containing EDTA/Rongalite The addition of creatinine as the third stability does not offer noticeable further stability improvement to EDTA/monothiolglycerol, EDTA/sulfite combination Three lead formulations having much better stability than the U.S. Pat. No. 10,456,355 formulation, with ~60% less degradation after 6 mon at 40° C., and with extrapolated shelf life at 24 months based on current stability trend (see FIG. 1). Formulation at 50 mg/mL has a viscosity close to water and injection time about 3 second for 2 mL fill. Addition of creatinine as the third stabilizer for EDTA/MTG and EDTA/sulfite offering no noticeable improvement based on 3 month data.

TABLE 9

| Formulation | Ingredient | Comment |
| --- | --- | --- |
| F#3 | EDTA/Rongalite | U.S. Pat. No. 10,456,355 |
| F#10 | EDTA/Rongalite/Creatinine | Improved on patented formulation |
| F#6 | EDTA/sulfite | Sulfite allergic concern |
| F#7 | EDTA/MTG | Best candidate |

TABLE 10

| | Total impurities at 25° C.: | | | |
| --- | --- | --- | --- | --- |
| Time (mon) | Rongalite/ EDTA | Rongalite/ EDTA/Creatinine | Sulfite/ EDTA | MTG/ EDTA |
| 0 | 0.00% | 0.00% | 0.09% | 0.00% |
| 3 | 0.20% | 0.09% | 0.04% | 0.06% |
| 6 | 0.61% | 0.12% | 0.21% | 0.12% |

TABLE 11

| Ingredients | Function | Composition per 1 mL | Composition per unit dose, 2 mL | FDA inactive ingredient database limit |
| --- | --- | --- | --- | --- |
| Hydrocortisone sodium phosphate | Active ingredient | 67.1 mg (50 mg hydrocortisone) | 134.2 mg (100 mg hydrocortisone) | — |
| Monobasic sodium phosphate anhydrous | Buffer agent | 1.0 mg | 2.0 mg | 1.2% w/v, IM |
| Dibasic sodium phosphate anhydrous | Buffer agent | 10.9 mg | 21.8 mg | 1.75% w/v, IM |
| Disodium edetate | Chelating agent | 0.2 mg | 0.4 mg | 10% w/v, IM |

TABLE 11-continued

| Ingredients | Function | Composition per 1 mL | Composition per unit dose, 2 mL | FDA inactive ingredient database limit |
|---|---|---|---|---|
| Monothioglycerol | Antioxidant | 5.0 mg | 10.0 mg | 0.5% w/v, IM |
| Sodium hydroxide/HCl | pH adjustor | Q.S pH (appr 8.0) | Q.S pH (appr 8.0) | — |
| Water | Solvent | Q.S. to 1 mL | Q.S. to 1 mL | — |

Figure 3A:
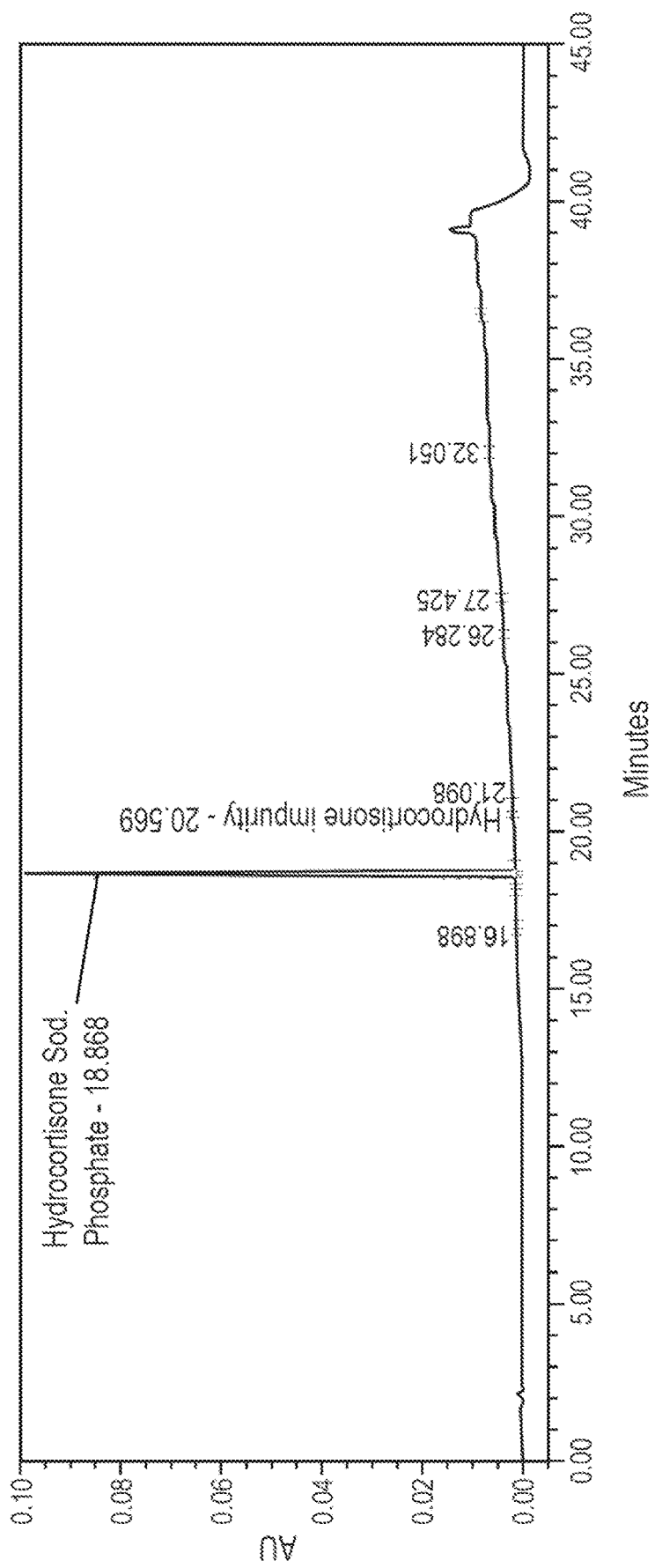
FIG. 3A illustrates the acid hydrolysis of HCP using 0.1 N HCl.
Figure 3B:
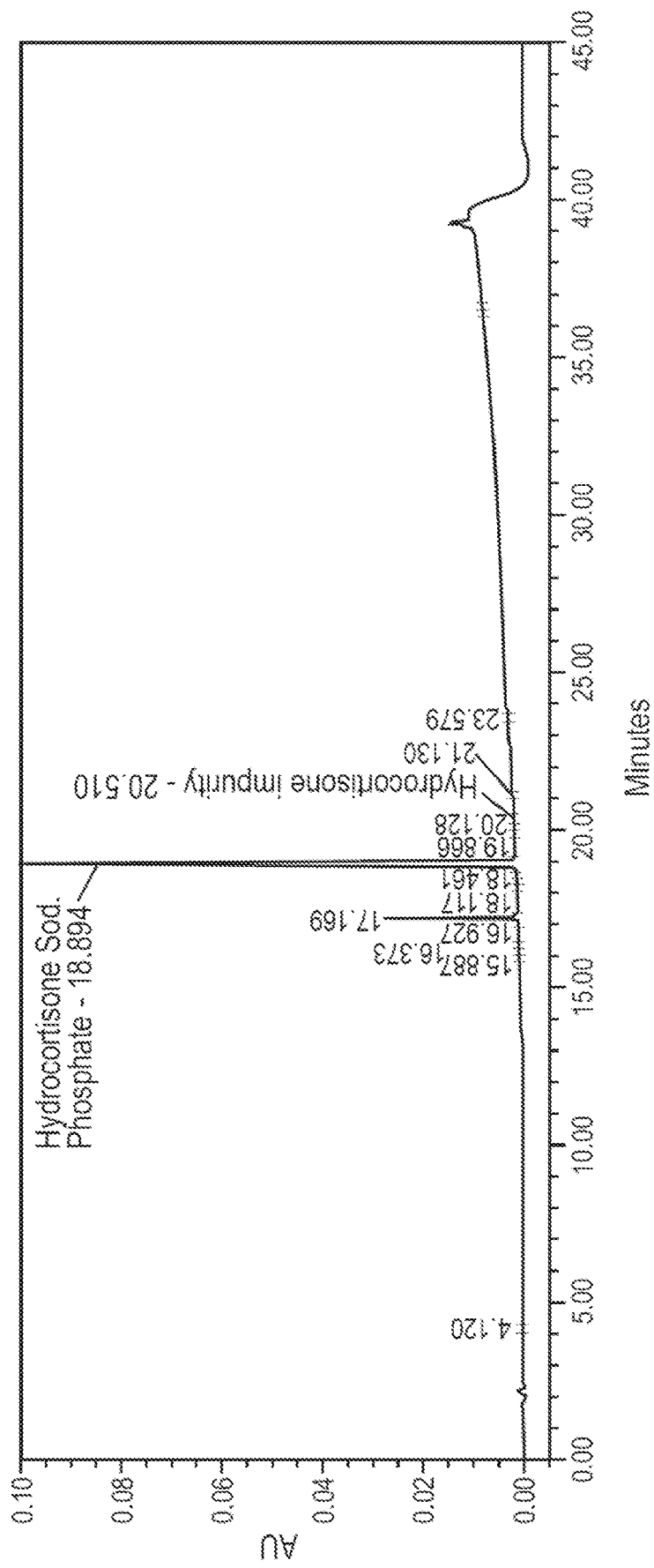
FIG. 3B illustrates alkali hydrolysis of HCP using 0.1 N NaOH.
Figure 3C:
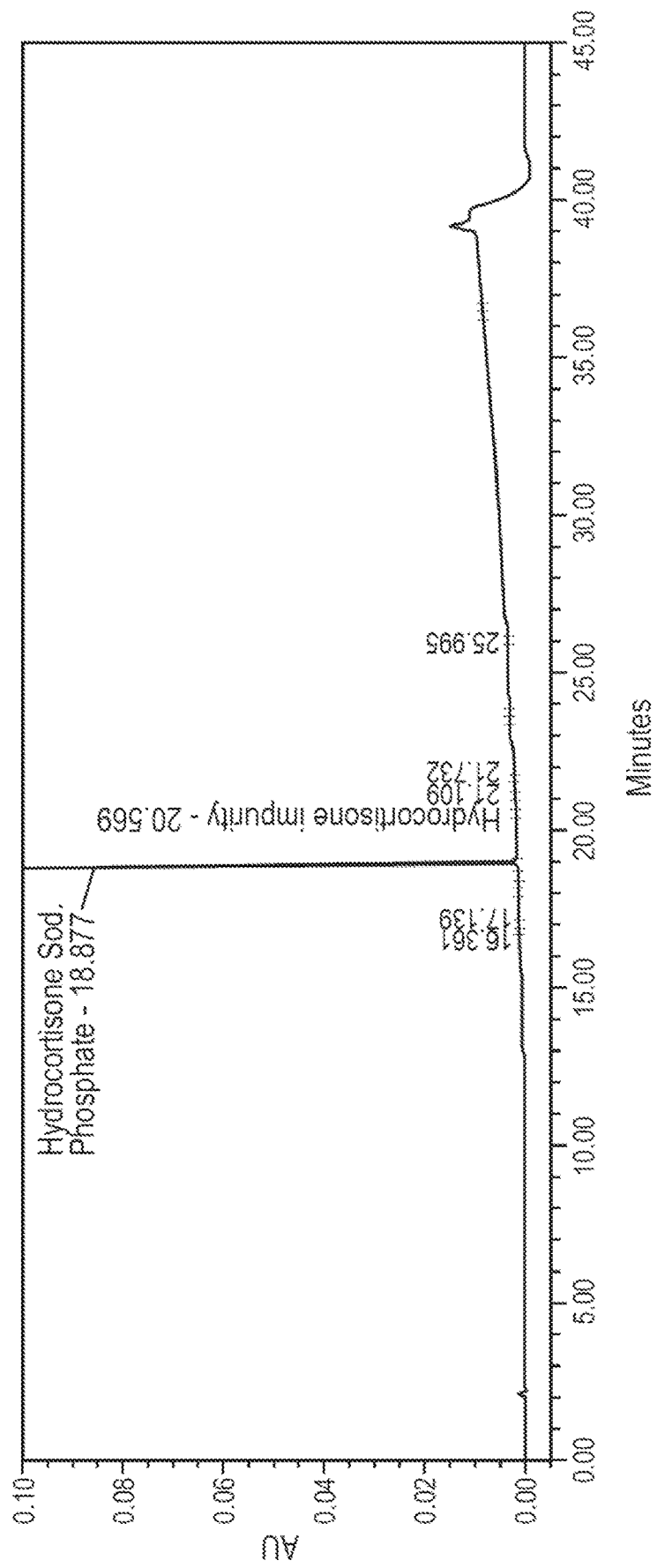
FIG. 3C illustrates the thermal degradation of HCP using dry heat.

To develop this method, Hydrocortisone sodium phosphate API was kept under stress conditions. These stress conditions included treatment with 0.1 N HCl, 0.1 N NaOH and dry heat. This was performed to investigate the nature of API and its compatibility with the stress conditions. It also helped generate degradation products to assess the specificity of the HPLC method under development. Information on degradation products and the conditions used to generate them was used to optimize the method for better resolution of such degradation products on chromatogram. FIGS. 3A-3C show chromatograms of HCP under stress conditions.

Forced degradation of HCP under 3 different stress conditions resulted in formation of Hydrocortisone, other common degradants. The proportions in which the degradants formed depended on the stress condition. Stress studies performed on the API were done for qualitative purpose only.

Preparation of HCP Prototype Formulations.

Following Tables 12 to 26 contain actual composition of HCP prototype formulations prepared for this study. Each Table also has values for density for each formulation prepared. Density has been calculated using gravimetry in the flask used to prepare formulation.

TABLE 12

Composition of HCP Formulation #1 Description:
Drug concentration: 13.42%, pH 7.0

| Ingredient | Amount w/v | Amount/50 mL | Actual amount |
|---|---|---|---|
| Hydrocortisone sodium phosphate (w/v) | 13.42% | 6.71 g | 6.7110 g |
| Monobasic sodium phosphate anhydrous | 0.1% | 50 mg | 50.3 mg |
| Dibasic sodium phosphate anhydrous | 1.09% | 545 mg | 545.4 mg |
| Disodium EDTA | 0.02% | 10 mg | 10.1 mg |
| Sodium formaldehyde sulfoxylate | 0.2% | 100 mg | 102.2 mg |
| Sodium hydroxide/HCl | q.s. to pH 7.0 | q.s. to pH 7.0 | 7.08 |
| Water | q.s. to 1 mL | q.s. to 50 mL | q.s. to 50 mL |

Density: 1.0602 g/mL

TABLE 13

Composition of HCP Formulation #2 Description:
Drug concentration: 13.42%, pH 7.5

| Ingredient | Amount w/v | Amount/50 mL | Actual amount |
|---|---|---|---|
| Hydrocortisone sodium phosphate (w/v) | 13.42% | 6.71 g | 6.7100 g |
| Monobasic sodium phosphate anhydrous | 0.1% | 50 mg | 50.0 mg |
| Dibasic sodium phosphate anhydrous | 1.09% | 545 mg | 545.1 mg |
| Disodium EDTA | 0.02% | 10 mg | 9.8 mg |
| Sodium formaldehyde sulfoxylate | 0.2% | 100 mg | 100.1 mg |
| Sodium hydroxide/HCl | q.s. to pH 7.5 | q.s. to pH 7.5 | 7.55 |
| Water | q.s. to 1 mL | q.s. to 50 mL | q.s. to 50 mL |

Density: 1.0587 g/mL

TABLE 14

Composition of HCP Formulation #3 Description:
Drug concentration: 13.42%, pH 8.0

| Ingredient | Amount w/v | Amount/50 mL | Actual amount |
|---|---|---|---|
| Hydrocortisone sodium phosphate (w/v) | 13.42% | 6.71 g | 6.7102 g |
| Monobasic sodium phosphate anhydrous | 0.1% | 50 mg | 50.9 mg |
| Dibasic sodium phosphate anhydrous | 1.09% | 545 mg | 545.6 mg |
| Disodium EDTA | 0.02% | 10 mg | 10.0 mg |
| Sodium formaldehyde sulfoxylate | 0.2% | 100 mg | 102.0 mg |
| Sodium hydroxide/HCl | q.s. to pH 8.0 | q.s. to pH 8.0 | 8.03 |
| Water | q.s. to 1 mL | q.s. to 50 mL | q.s. to 50 mL |

Density: 1.0597 g/mL

TABLE 15

Composition of HCP Formulation #4 Description:
Drug concentration: 13.42%, pH 8.5

| Ingredient | Amount w/v | Amount/50 mL | Actual amount |
|---|---|---|---|
| Hydrocortisone sodium phosphate (w/v) | 13.42% | 6.71 g | 6.7107 g |
| Monobasic sodium phosphate anhydrous | 0.1% | 50 mg | 50.7 mg |
| Dibasic sodium phosphate anhydrous | 1.09% | 545 mg | 544.9 mg |
| Disodium EDTA | 0.02% | 10 mg | 10.4 mg |
| Sodium formaldehyde sulfoxylate | 0.2% | 100 mg | 99.9 mg |
| Sodium hydroxide/HCl | q.s. to pH 8.5 | q.s. to pH 8.5 | 8.50 |
| Water | q.s. to 1 mL | q.s. to 50 mL | q.s. to 50 ml |

Density: 1.0602

TABLE 16

Composition of HCP Formulation #5 Description:
Drug concentration: 6.71%, pH 8.0

| Ingredient | Amount w/v | Amount/50 mL | Actual amount |
|---|---|---|---|
| Hydrocortisone sodium phosphate (w/v) | 6.71% | 3.355 g | 3.3556 g |
| Monobasic sodium phosphate anhydrous | 0.1% | 50 mg | 50.2 mg |
| Dibasic sodium phosphate anhydrous | 1.09% | 545 mg | 544.9 mg |
| Disodium EDTA | 0.02% | 10 mg | 9.9 mg |
| Sodium formaldehyde sulfoxylate | 0.2% | 100 mg | 100.7 mg |
| Sodium hydroxide/HCl | q.s. to pH 8.0 | q.s. to pH 8.0 | 8.03 |
| Water | q.s. to 1 mL | q.s. to 50 mL | q.s. to 50 mL |

Density: 1.0329 g/mL

TABLE 17

Composition of HCP Formulation #6 Description:
Drug concentration: 13.42%, pH 8.0, Effect of Sodium sulfite

| Ingredient | Amount w/v | Amount/50 mL | Actual amount |
|---|---|---|---|
| Hydrocortisone sodium phosphate (w/v) | 13.42% | 6.71 g | 6.7107 g |
| Monobasic sodium phosphate anhydrous | 0.1% | 50 mg | 50.4 mg |
| Dibasic sodium phosphate anhydrous | 1.09% | 545 mg | 545.2 mg |
| Disodium EDTA | 0.02% | 10 mg | 10.0 mg |
| Sodium sulfite | 0.2% | 100 mg | 100.0 mg |
| Sodium hydroxide/HCl | q.s. to pH 8.0 | q.s. to pH 8.0 | 8.04 |
| Water | q.s. to 1 mL | q.s. to 50 mL | q.s. to 50 mL |

Density: 1.0584 g/mL

TABLE 18

Composition of HCP Formulation #7
Description: Drug concentration: 13.42%,
pH 8.0, Effect of Monothioglycerol

| Ingredient | Amount w/v | Amount/ 50 mL | Actual amount |
|---|---|---|---|
| Hydrocortisone sodium phosphate (w/v) | 13.42% | 6.71 g | 6.7100 g |
| Monobasic sodium phosphate anhydrous | 0.1% | 50 mg | 50.5 mg |
| Dibasic sodium phosphate anhydrous | 1.09% | 545 mg | 545.2 mg |
| Disodium EDTA | 0.02% | 10 mg | 10.3 mg |
| Monothioglycerol | 0.5% | 250 mg | 256.6 mg |
| Sodium hydroxide/HCl | q.s. to pH 8.0 | q.s. to pH 8.0 | 8.15 |
| Water | q.s. to 1 mL | q.s. to 50 mL | q.s. to 50 mL |

Density: 1.0600 g/mL

TABLE 19

Composition of HCP Formulation #8
Description: Drug concentration: 13.42%,
pH 8.0, Effect of Ascorbic Acid.

| Ingredient | Amount w/v | Amount/ 200 mL | Actual amount |
|---|---|---|---|
| Hydrocortisone sodium phosphate (w/v) | 13.42% | 26.84 g | 26.838 g |
| Monobasic sodium phosphate anhydrous | 0.1% | 200 mg | 200.1 mg |
| Dibasic sodium phosphate anhydrous | 1.09% | 2.180 g | 2.1806 g |
| Disodium EDTA | 0.02% | 40 mg | 40.0 mg |
| Ascorbic acid | 0.2% | 400 mg | 400.2 mg |
| Sodium hydroxide/HCl | q.s. to pH 8.0 | q.s. to pH 8.0 | 7.98 |
| Water | q.s. to 1 mL | q.s. to 200 mL | q.s. to 200 mL |

Density: 1.0598 g/mL

Syringes of HCP Formulation #8 was divided into 3 sublots HCP F #8A, HCP F #8B and HCP F #8C.

HCP F #8A syringes were kept unpouched.

HCP F #8B syringes were pouched with Nitrogen purging.

HCP F #8C syringes were pouched with 2 Oxygen scavengers (no Nitrogen purging).

TABLE 20

Composition of HCP Formulation #9
Description: Drug concentration: 13.42%,
pH 8.0, Effect of Methoinine.

| Ingredient | Amount w/v | Amount/ 50 mL | Actual amount |
|---|---|---|---|
| Hydrocortisone sodium phosphate (w/v) | 13.42% | 6.71 g | 6.7113 g |
| Monobasic sodium phosphate anhydrous | 0.1% | 50 mg | 50.0 mg |
| Dibasic sodium phosphate anhydrous | 1.09% | 545 mg | 545.0 mg |
| Disodium EDTA | 0.02% | 10 mg | 10.2 mg |
| Methionine | 0.05% | 25 mg | 25.1 mg |
| Sodium hydroxide/HCl | q.s. to pH 8.0 | q.s. to pH 8.0 | 8.14 |
| Water | q.s. to 1 mL | q.s. to 50 mL | q.s. to 50 mL |

Density: 1.0592 g/mL

TABLE 21

Composition of HCP Formulation #10
Description: Drug concentration: 13.42%, pH 8.0, Effect of Creatinine.

| Ingredient | Amount w/v | Amount/ 50 mL | Actual amount |
|---|---|---|---|
| Hydrocortisone sodium phosphate (w/v) | 13.42% | 6.71 g | 6.7109 g |
| Monobasic sodium phosphate anhydrous | 0.1% | 50 mg | 50.2 mg |
| Dibasic sodium phosphate anhydrous | 1.09% | 545 mg | 545.5 mg |
| Disodium EDTA | 0.02% | 10 mg | 10.0 mg |
| Sodium formaldehyde sulfoxylate | 0.2% | 100 mg | 101.0 mg |
| Creatinine | 0.8% | 400 mg | 400.2 mg |
| Sodium hydroxide/HCl | q.s. to pH 8.0 | q.s. to pH 8.0 | 8.09 |
| Water | q.s. to 1 mL | q.s. to 50 mL | q.s. to 50 mL |

Density: 1.0610 g/mL

TABLE 22

Composition of HCP Formulation #11
Description: Drug concentration: 13.42%, pH 8.0, Effect of Niacinamide.

| Ingredient | Amount w/v | Amount/ 50 mL | Actual amount |
|---|---|---|---|
| Hydrocortisone sodium phosphate (w/v) | 13.42% | 6.71 g | 6.7107 g |
| Monobasic sodium phosphate anhydrous | 0.1% | 50 mg | 50.0 mg |
| Dibasic sodium phosphate anhydrous | 1.09% | 545 mg | 545.2 mg |
| Disodium EDTA | 0.02% | 10 mg | 10.4 mg |
| Sodium formaldehyde sulfoxylate | 0.2% | 100 mg | 100.9 mg |
| Niacinamide | 2.5% | 1.25 g | 1.2504 g |
| Sodium hydroxide/HCl | q.s. to pH 8.0 | q.s. to pH 8.0 | 7.98 |
| Water | q.s. to 1 mL | q.s. to 50 mL | q.s. to 50 mL |

Density: 1.0655 g/mL

TABLE 23

Composition of HCP Formulation #12
Description: Drug concentration: 13.42%, pH 8.0, Effect of 5% HP-β-cyclodextrin.

| Ingredient | Amount w/v | Amount/ 50 mL | Actual amount |
|---|---|---|---|
| Hydrocortisone sodium phosphate (w/v) | 13.42% | 6.71 g | 6.7106 g |
| Monobasic sodium phosphate anhydrous | 0.1% | 50 mg | 50.0 mg |
| Dibasic sodium phosphate anhydrous | 1.09% | 545 mg | 545.2 mg |
| Disodium EDTA | 0.02% | 10 mg | 9.9 mg |
| Sodium formaldehyde sulfoxylate | 0.2% | 100 mg | 100.9 mg |
| HP-β-cyclodextrin | 5.0% | 2.5 g | 2.5002 g |
| Sodium hydroxide/HCl | q.s. to pH 8.0 | q.s. to pH 8.0 | 8.06 |
| Water | q.s. to 1 mL | q.s. to 50 mL | q.s. to 50 mL |

Density: 1.0749 g/mL

TABLE 24

Composition of HCP Formulation #13
Description: Drug concentration: 13.42%, pH 8.0, Effect of 10% HP-β-cyclodextrin.

| Ingredient | Amount w/v | Amount/ 50 mL | Actual amount |
|---|---|---|---|
| Hydrocortisone sodium phosphate (w/v) | 13.42% | 6.71 g | 6.7098 g |
| Monobasic sodium phosphate anhydrous | 0.1% | 50 mg | 50.1 mg |
| Dibasic sodium phosphate anhydrous | 1.09% | 545 mg | 544.8 mg |
| Disodium EDTA | 0.02% | 10 mg | 10.3 mg |
| Sodium formaldehyde sulfoxylate | 0.2% | 100 mg | 100.9 mg |
| HP-β-cyclodextrin | 10.0% | 5.0 g | 5.0007 g |
| Sodium hydroxide/HCl | q.s. to pH 8.0 | q.s. to pH 8.0 | 7.98 |
| Water | q.s. to 1 mL | q.s. to 50 mL | q.s. to 50 mL |

Density: 1.0883 g/mL

TABLE 25

Composition of HCP Formulation #14
Description: Drug concentration: 13.42%, pH 8.0, Effect of Lactbionic acid.

| Ingredient | Amount w/v | Amount/ 50 mL | Actual amount |
|---|---|---|---|
| Hydrocortisone sodium phosphate (w/v) | 13.42% | 6.71 g | 6.7100 g |
| Monobasic sodium phosphate anhydrous | 0.1% | 50 mg | 49.9 mg |
| Dibasic sodium phosphate anhydrous | 1.09% | 545 mg | 545.3 mg |
| Disodium EDTA | 0.02% | 10 mg | 9.8 mg |
| Sodium formaldehyde sulfoxylate | 0.2% | 100 mg | 101.8 mg |
| Lactobionic Acid | 0.2% | 100 mg | 100.4 mg |
| Sodium hydroxide/HCl | q.s. to pH 8.0 | q.s. to pH 8.0 | 8.04 |
| Water | q.s. to 1 mL | q.s. to 50 mL | q.s. to 50 mL |

Density: 1.0607 g/mL

TABLE 26

Compositin of HCP Fomulation #15 (Previously HCP F #3)
Description: Drug concentration: 13.42%, pH 8.0.

| Ingredient | Amount w/v | Amount/ 200 mL | Actual amount |
|---|---|---|---|
| Hydrocortisone sodium phosphate (w/v) | 13.42% | 26.840 g | 26.838 g |
| Monobasic sodium phosphate anhydrous | 0.1% | 200 mg | 200.3 mg |
| Dibasic sodium phosphate anhydrous | 1.09% | 2.180 g | 2.1806 g |
| Disodium EDTA | 0.02% | 40 mg | 40.3 mg |
| Sodium formaldehyde sulfoxylate | 0.2% | 400 mg | 402.0 mg |
| Sodium hydroxide/HCl | q.s to pH 8.0 | q.s to pH 8.0 | 7.98 |
| Water | q.s to 1 mL | q.s to 200 mL | q.s to 200 mL |

Density: 1.0603 g/mL

Syringes of HCP Formulation #15 was divided into 3 sublots HCP F #15A, HCP F #15B and HCP F #15C.

HCP F #15A syringes were kept unpouched.

HCP F #15B syringes were pouched with Nitrogen purging.

HCP F #15C syringes were pouched with 2 Oxygen scavengers (no Nitrogen purging).

Stability data for HCP prototype formulations.

Following Tables 27 to 45 contain stability profile for HCP formulations 1 to 15 up to 6 month storage at 25° C. and 40° C. It has data on % assay, % peak area of HCP, % area of known impurity Hydrocortisone and other unknown impurities. Please note that the reporting threshold for Hydrocortisone impurity have been kept as 0.01% as it is a major degradant. For other impurities, it has been kept as 0.05% on chromatogram. Once the identification and qualification these unknown impurities is completed, a suitable identification threshold and qualification threshold can be used in future studies.

Stability data on following 4 unknown impurities have been kept in the table according to their formation. The sum of total other unknown impurities, which are lower in amounts have been taken into account when % peak area of HCP was calculated. Following formulas can be used to calculate impurities.

Sum of total impurities=100−% peak area of HCP

Sum of total unknown imp=100−(% peak of HCP+% peak of Hydrocortisone imp)

Sum of other unknown imp=100−(sum of % peak of HCP,Hydrocortisone & imp1to4)

Impurity 1 in the stability data tables has been identified as the peak of a degradation product that elutes at 5.00 minutes on chromatogram. The relative retention time for this impurity is 0.26. This impurity was observed during the alkali hydrolysis of HCP using 0.1N NaOH during method development. This impurity was also prevalent from early stages of the accelerated stability condition (40° C.) in formulations that had Sodium formaldehyde sulfoxylate in their composition as an antioxidant.

Impurity 2 in the stability data tables has been identified as the peak of a degradation product that elutes at 15.07 minutes on chromatogram. The relative retention time for this impurity is 0.79. This impurity was not observed during forced degradation of HCP in method development.

Impurity 3 in the stability data tables has been identified as the peak of a degradation product that elutes at 17.25 minutes on chromatogram. The relative retention time for this impurity is 0.91. This impurity was observed during the alkali hydrolysis of HCP using 0.1 N NaOH during method development.

Impurity 4 in the stability data tables has been identified as the peak of a degradation product that elutes at 23.64 minutes on chromatogram. The relative retention time for this impurity is 1.24. This impurity was observed during the thermal degradation of HCP using dry heat during method development.

Amounts of these 4 unknown impurities are more in formulations compared to those of other unknown impurities. Further investigation should be done on such unknown impurities to reduce the risk of their formation in future formulations.

TABLE 27

Stability profile of HCP Formulation #1
Description: Drug concentration: 13.42%, pH 7.0

| Duration | % Assay | % Impurity 1 RRT 0.26 | % Impurity 2 RRT 0.79 | % Impurity 3 RRT 0.91 | % Impurity 4 RRT 1.24 | % Hydrocortisone RRT 1.09 | % Peak area | pH of formulation |
|---|---|---|---|---|---|---|---|---|
| Storage condition: 25° C. | | | | | | | | |
| Initial | 101.27 | — | — | — | — | 0.0 | 100.0 | 7.08 |
| 3 M | 97.53 | — | — | — | 0.16 | 0.18 | 99.6 | 7.08 |
| 6 M | 95.30 | — | — | — | 0.28 | 0.28 | 99.2 | 7.04 |
| 9 M | | | | | | | | |
| 12 M | | | | | | | | |
| 18 M | | | | | | | | |
| 24 M | | | | | | | | |
| Storage condition: 40° C. | | | | | | | | |
| Initial | 101.27 | — | — | — | — | 0.0 | 100.0 | 7.08 |
| 1 M | 100.64 | — | — | — | 0.21 | 0.70 | 98.3 | 7.05 |
| 2 M | 91.53 | 0.13 | 0.11 | 0.05 | 0.93 | 0.87 | 96.5 | 6.99 |
| 3 M | 89.05 | 0.24 | 0.14 | 0.06 | 1.50 | 0.92 | 94.9 | 7.10 |
| 6 M | 80.32 | 0.63 | 0.23 | 0.14 | 3.42 | 1.40 | 89.6 | 7.04 |

TABLE 28

Stability profile of HCP Formulation #2
Description: Drug concentration: 13.42%, pH 7.5

| Duration | % Assay | % Impurity 1 RRT 0.26 | % Impurity 2 RRT 0.79 | % Impurity 3 RRT 0.91 | % Impurity 4 RRT 1.24 | % Hydrocortisone RRT 1.09 | % Peak area | pH of formulation |
|---|---|---|---|---|---|---|---|---|
| Storage condition: 25° C. | | | | | | | | |
| Initial | 100.85 | — | — | — | — | 0.0 | 100.0 | 7.61 |
| 3 M | 95.53 | — | — | — | 0.07 | 0.08 | 99.8 | 7.56 |
| 6 M | 95.80 | — | 0.80 | — | 0.10 | 0.10 | 99.5 | 7.51 |
| 9 M | | | | | | | | |
| 12 M | | | | | | | | |
| 18 M | | | | | | | | |
| 24 M | | | | | | | | |
| Storage condition: 40° C. | | | | | | | | |
| Initial | 100.85 | — | — | — | — | 0.0 | 100.0 | 7.61 |
| 1 M | 96.49 | — | 0.13 | 0.11 | 0.13 | 0.31 | 98.9 | 7.52 |
| 2 M | 95.21 | 0.27 | 0.22 | 0.09 | 0.44 | 0.30 | 97.7 | 7.50 |
| 3 M | 92.30 | 0.45 | 0.24 | 0.16 | 0.55 | 0.25 | 97.4 | 7.54 |
| 6 M | 86.72 | 1.36 | 0.41 | 0.22 | 1.36 | 0.41 | 94.1 | 7.44 |

TABLE 29

Stability profile of HCP Formulation #3
Description: Drug concentration: 13.42%, pH 8.0

| Duration | % Assay | % Impurity 1 RRT 0.26 | % Impurity 2 RRT 0.79 | % Impurity 3 RRT 0.91 | % Impurity 4 RRT 1.24 | % Hydrocortisone RRT 1.09 | % Peak area | pH of formulation |
|---|---|---|---|---|---|---|---|---|
| Storage condition: 25° C. | | | | | | | | |
| Initial | 100.62 | — | — | — | — | 0.0 | 100.0 | 8.17 |
| 3 M | 95.08 | — | 0.10 | — | — | 0.04 | 99.8 | 7.97 |
| 6 M | 95.84 | 0.14 | 0.16 | — | 0.05 | 0.05 | 99.4 | 7.88 |
| 9 M | | | | | | | | |
| 12 M | | | | | | | | |
| 18 M | | | | | | | | |
| 24 M | | | | | | | | |
| Storage condition: 40° C. | | | | | | | | |
| Initial | 100.62 | — | — | — | — | 0.0 | 100.0 | 8.17 |
| 1 M | 96.17 | — | 0.25 | 0.10 | 0.16 | 0.11 | 99.0 | 8.05 |
| 2 M | 95.58 | 0.72 | 0.36 | 0.18 | 0.21 | 0.14 | 97.7 | 7.89 |
| 3 M | 92.89 | 1.13 | 0.47 | 0.25 | 0.35 | 0.13 | 96.9 | 7.86 |
| 6 M | 85.66 | 2.30 | 0.57 | 0.45 | 0.75 | 0.16 | 94.3 | 7.75 |

TABLE 30

Stability profile of HCP Formulation #4
Description: Drug concentration: 13.42%, pH 8.5

| Duration | % Assay | % Impurity 1 RRT 0.26 | % Impurity 2 RRT 0.79 | % Impurity 3 RRT 0.91 | % Impurity 4 RRT 1.24 | % Hydrocortisone RRT 1.09 | % Peak area | pH of formulation |
|---|---|---|---|---|---|---|---|---|
| Storage condition: 25° C. | | | | | | | | |
| Initial | 100.41 | — | — | — | — | 0.0 | 100.0 | 8.54 |
| 3 M | 95.95 | — | 0.14 | — | — | 0.04 | 99.7 | 8.30 |
| 6 M | 95.36 | 0.19 | 0.23 | — | 0.06 | 0.03 | 99.3 | 8.06 |
| 9 M | | | | | | | | |
| 12 M | | | | | | | | |
| 18 M | | | | | | | | |
| 24 M | | | | | | | | |
| Storage condition: 40° C. | | | | | | | | |
| Initial | 100.41 | — | — | — | — | 0.0 | 100.0 | 8.54 |
| 1 M | 96.64 | — | 0.31 | 0.12 | 0.10 | 0.08 | 99.0 | 8.27 |
| 2 M | 94.39 | 0.80 | 0.44 | 0.21 | 0.12 | 0.09 | 98.0 | 8.07 |
| 3 M | 92.66 | 1.20 | 0.52 | 0.30 | 0.22 | 0.09 | 97.2 | 8.08 |
| 6 M | 88.67 | 2.42 | 0.63 | 0.55 | 0.55 | 0.12 | 94.4 | 7.88 |

TABLE 31

Stability profile of HCP Formulation #5
Description: Drug concentration: 13.42%, pH 8.5

| Duration | % Assay | % Impurity 1 RRT 0.26 | % Impurity 2 RRT 0.79 | % Impurity 3 RRT 0.91 | % Impurity 4 RRT 1.24 | % Hydrocortisone RRT 1.09 | % Peak area | pH of formulation |
|---|---|---|---|---|---|---|---|---|
| Storage condition: 25° C. | | | | | | | | |
| Initial | 99.63 | — | — | — | — | 0.0 | 100.0 | 8.02 |
| 3 M | 88.39 | — | 0.12 | — | — | 0.06 | 99.7 | 7.99 |
| 6 M | 92.41 | 0.12 | 0.19 | — | 0.06 | 0.10 | 99.3 | 7.76 |
| 9 M | | | | | | | | |
| 12 M | | | | | | | | |
| 18 M | | | | | | | | |
| 24 M | | | | | | | | |
| Storage condition: 40° C. | | | | | | | | |
| Initial | 99.63 | — | — | — | — | 0.0 | 100.0 | 8.02 |
| 1 M | 91.10 | — | 0.29 | 0.10 | 0.10 | 0.15 | 99.0 | 7.88 |
| 2 M | 88.86 | 0.93 | 0.55 | 0.16 | 0.23 | 0.20 | 97.5 | 7.79 |

TABLE 31-continued

Stability profile of HCP Formulation #5
Description: Drug concentration: 13.42%, pH 8.5

| Duration | % Assay | % Impurity 1 RRT 0.26 | % Impurity 2 RRT 0.79 | % Impurity 3 RRT 0.91 | % Impurity 4 RRT 1.24 | % Hydrocortisone RRT 1.09 | % Peak area | pH of formulation |
|---|---|---|---|---|---|---|---|---|
| 3 M | 87.25 | 1.37 | 0.71 | 0.22 | 0.42 | 0.17 | 96.3 | 7.78 |
| 6 M | 79.67 | 3.11 | 1.16 | 0.35 | 0.84 | 0.22 | 92.6 | 7.64 |

TABLE 32

Stability profile of HCP Formulation #4
Description: Drug concentration: 13.42%, pH 8.0, Effect of Sodium sulfite

| Duration | % Assay | % Impurity 1 RRT 0.26 | % Impurity 2 RRT 0.79 | % Impurity 3 RRT 0.91 | % Impurity 4 RRT 1.24 | % Hydrocortisone RRT 1.09 | % Peak area | pH of formulation |
|---|---|---|---|---|---|---|---|---|
| Storage condition: 25° C. | | | | | | | | |
| Initial | 103.37 | — | — | — | — | 0.0 | 99.9 | 8.34 |
| 3 M | 101.28 | — | — | — | — | 0.00 | 99.9 | 8.50 |
| 6 M | 99.59 | — | — | 0.07 | 0.06 | 0.02 | 99.8 | 8.40 |
| 9 M | | | | | | | | |
| 12 M | | | | | | | | |
| 18 M | | | | | | | | |
| 24 M | | | | | | | | |
| Storage condition: 40° C. | | | | | | | | |
| Initial | 103.37 | — | — | — | — | 0.0 | 99.9 | 8.34 |
| 1 M | 100.02 | — | — | 0.29 | — | 0.07 | 99.5 | 8.44 |
| 2 M | 99.71 | — | — | 0.45 | 0.13 | 0.07 | 99.2 | 8.41 |
| 3 M | 99.46 | — | — | 0.75 | 0.19 | 0.07 | 98.9 | 8.47 |
| 6 M | 95.26 | 0.06 | — | 1.16 | 0.26 | 0.06 | 98.2 | 8.46 |

TABLE 33

Stability profile of HCP Formulation #7
Description: Drug concentration: 13.42%, pH 8.0, Effect of Monothioglycerol

| Duration | % Assay | % Impurity 1 RRT 0.26 | % Impurity 2 RRT 0.79 | % Impurity 3 RRT 0.91 | % Impurity 4 RRT 1.24 | % Hydrocortisone RRT 1.09 | % Peak area | pH of formulation |
|---|---|---|---|---|---|---|---|---|
| Storage condition: 25° C. | | | | | | | | |
| Initial | 103.06 | — | — | — | — | 0.0 | 100.0 | 8.56 |
| 3M | 98.87 | — | — | 0.05 | — | 0.00 | 99.9 | 8.65 |
| 6M | 99.58 | — | — | 0.00 | — | 0.03 | 99.9 | 8.58 |
| 9M | | | | | | | | |
| 12M | | | | | | | | |
| 18M | | | | | | | | |
| 24M | | | | | | | | |
| Storage condition: 40° C. | | | | | | | | |
| Initial | 103.06 | — | — | — | — | 0.0 | 100.0 | 8.56 |
| 1M | 100.27 | — | — | 0.27 | — | 0.07 | 99.7 | 8.59 |
| 2M | 101.01 | — | — | 0.51 | — | 0.10 | 99.3 | 8.51 |
| 3M | 99.27 | — | — | 0.84 | — | 0.12 | 98.9 | 8.49 |
| 6M | 97.99 | — | — | 1.39 | — | 0.12 | 98.2 | 8.58 |

TABLE 34

Description: Drug concentration: 13.42%, pH 8.0, Effect Ascorbic acid and unpouched sample

| Duration | % Assay | % Impurity 1 RRT 0.26 | % Impurity 2 RRT 0.79 | % Impurity 3 RRT 0.91 | % Impurity 4 RRT 1.24 | % Hydrocortisone RRT 1.09 | % Peak area | pH of formulation |
|---|---|---|---|---|---|---|---|---|
| Storage condition: 25° C. | | | | | | | | |
| Initial | 99.92 | — | — | — | — | 0.0 | 100.0 | 8.37 |
| 3M | 99.94 | — | — | — | 0.05 | 0.04 | 99.9 | 8.08 |
| 6M | 99.40 | — | — | 0.04 | 0.08 | 0.05 | 99.8 | 7.96 |
| 9M | | | | | | | | |
| 12M | | | | | | | | |
| 18M | | | | | | | | |
| 24M | | | | | | | | |
| Storage condition: 40° C. | | | | | | | | |
| Intial | 99.92 | — | — | — | — | 0.0 | 100.0 | 8.37 |
| 1M | 99.04 | — | — | 0.13 | — | 0.10 | 99.6 | 8.19 |
| 2M | 99.84 | — | — | 0.16 | 0.15 | 0.14 | 99.5 | 7.94 |
| 3M | 99.41 | — | — | 0.28 | 0.29 | 0.24 | 99.1 | 7.88 |
| 6M | 95.40 | — | — | 0.48 | 0.71 | 0.46 | 97.9 | 7.72 |

TABLE 35

Stability profile of HCP Formulation #8B
Description: Drug concentration: 13.42%, pH 8.0, Effect of Ascorbic acid and pouched with Nitrogen purging

| Duration | % Assay | % Impurity 1 RRT 0.26 | % Impurity 2 RRT 0.79 | % Impurity 3 RRT 0.91 | % Impurity 4 RRT 1.24 | % Hydrocortisone RRT 1.09 | % Peak area | pH of formulation |
|---|---|---|---|---|---|---|---|---|
| Storage condition: 25° C. | | | | | | | | |
| Initial | 99.92 | — | — | — | — | 0.0 | 100.0 | 8.37 |
| 3M | 100.16 | — | — | — | 0.07 | 0.04 | 99.8 | 7.97 |
| 6M | 98.25 | — | — | 0.03 | 0.10 | 0.06 | 99.8 | 7.82 |
| 9M | | | | | | | | |
| 12M | | | | | | | | |
| 18M | | | | | | | | |
| 24M | | | | | | | | |
| Storage condition: 40° C. | | | | | | | | |
| Initial | 99.92 | — | — | — | — | 0.0 | 100.0 | 8.37 |
| 1M | 99.74 | — | — | 0.11 | 0.11 | 0.10 | 99.5 | 8.47 |
| 2M | 99.63 | — | — | 0.18 | 0.17 | 0.16 | 99.4 | 7.94 |
| 3M | 99.55 | — | — | 0.25 | 0.28 | 0.22 | 99.1 | 7.90 |
| 6M | 98.84 | — | — | 0.45 | 0.70 | 0.44 | 98.0 | 7.72 |

TABLE 36

Stability profile of HCP Formulation #8C
Description: Drug concentration: 13.42%, pH 8.0, Effect of Ascorbic acid and pouched with 2 Oxygen scavengers.

| Duration | % Assay | % Impurity 1 RRT 0.26 | % Impurity 2 RRT 0.79 | % Impurity 3 RRT 0.91 | % Impurity 4 RRT 1.24 | % Hydrocortisone RRT 1.09 | % Peak area | pH of formulation |
|---|---|---|---|---|---|---|---|---|
| Storage condition: 25° C. | | | | | | | | |
| Initial | 99.92 | — | — | — | — | 0.0 | 100.0 | 8.37 |
| 3M | 101.20 | — | — | — | 0.05 | 0.04 | 99.9 | 8.12 |
| 6M | 100.06 | — | — | 0.03 | 0.07 | 0.05 | 99.9 | 7.89 |
| 9M | | | | | | | | |
| 12M | | | | | | | | |
| 18M | | | | | | | | |
| 24M | | | | | | | | |
| Storage condition: 40° C. | | | | | | | | |
| Initial | 99.92 | — | — | — | — | 0.0 | 100.0 | 8.37 |
| 1M | 99.73 | — | — | 0.11 | — | 0.10 | 99.6 | 8.06 |
| 2M | 99.96 | — | — | 0.23 | 0.18 | 0.15 | 99.4 | 8.03 |

TABLE 36-continued

Stability profile of HCP Formulation #8C
Description: Drug concentration: 13.42%, pH 8.0, Effect of Ascorbic acid and pouched with 2 Oxygen scavengers.

| Duration | % Assay | % Impurity 1 RRT 0.26 | % Impurity 2 RRT 0.79 | % Impurity 3 RRT 0.91 | % Impurity 4 RRT 1.24 | % Hydrocortisone RRT 1.09 | % Peak area | pH of formulation |
|---|---|---|---|---|---|---|---|---|
| 3M | 100.11 | — | — | 0.37 | 0.30 | 0.21 | 99.0 | 8.00 |
| 6M | 97.27 | — | — | 0.55 | 0.58 | 0.31 | 98.3 | 7.93 |

TABLE 37

Stability profile of HCP Formulation #9
Description: Drug concentration: 13.42%, pH 8.0, Effect of Methoinine.

| Duration | % Assay | % Impurity 1 RRT 0.26 | % Impurity 2 RRT 0.79 | % Impurity 3 RRT 0.91 | % Impurity 4 RRT 1.24 | % Hydrocortisone RRT 1.09 | % Peak area | pH of formulation |
|---|---|---|---|---|---|---|---|---|
| Storage condition: 25° C. | | | | | | | | |
| Initial | 102.86 | — | — | — | — | 0.0 | 100.0 | 8.61 |
| 3M | 97.89 | 0.05 | — | 0.04 | 0.06 | 0.00 | 99.7 | 8.38 |
| 6M | 98.37 | 0.07 | — | 0.06 | 0.08 | 0.02 | 99.6 | 8.26 |
| 9M | | | | | | | | |
| 12M | | | | | | | | |
| 18M | | | | | | | | |
| 24M | | | | | | | | |
| Storage condition: 40° C. | | | | | | | | |
| Initial | 102.86 | — | — | — | — | 0.0 | 100.0 | 8.61 |
| 1M | 96.11 | — | — | 0.22 | 0.34 | 0.05 | 99.4 | 8.19 |
| 2M | 99.09 | 0.05 | — | 0.39 | 0.14 | 0.07 | 99.0 | 8.29 |
| 3M | 97.52 | 0.06 | — | 0.56 | 0.24 | 0.08 | 98.7 | 8.29 |
| 6M | 95.08 | 0.07 | — | 0.95 | 0.42 | 0.10 | 97.6 | 8.16 |

TABLE 38

Stability profile of HCP Formulation #10
Description: Drug concentration: 13.42%, pH 8.0, Effect of Creatinine.

| Duration | % Assay | % Impurity 1 RRT 0.26 | % Impurity 2 RRT 0.79 | % Impurity 3 RRT 0.91 | % Impurity 4 RRT 1.24 | % Hydrocortisone RRT 1.09 | % Peak area | pH of formulation |
|---|---|---|---|---|---|---|---|---|
| Storage condition: 25° C. | | | | | | | | |
| Initial | 103.32 | — | — | — | — | 0.0 | 100.0 | 8.11 |
| 3M | 95.68 | — | 0.03 | — | — | 0.04 | 99.9 | 8.01 |
| 6M | 93.95 | — | 0.05 | — | — | 0.3 | 99.9 | 7.95 |
| 9M | | | | | | | | |
| 12M | | | | | | | | |
| 18M | | | | | | | | |
| 24M | | | | | | | | |
| Storage condition: 40° C. | | | | | | | | |
| Initial | 103.32 | — | — | — | — | 0.0 | 100.0 | 8.11 |
| 1M | 91.71 | 0.07 | 0.08 | 0.08 | — | 0.09 | 99.6 | 8.05 |
| 2M | 101.45 | 0.11 | 0.10 | 0.11 | — | 0.09 | 99.5 | 7.82 |
| 3M | 93.59 | 0.27 | 0.13 | 0.17 | 0.07 | 0.12 | 98.8 | 7.85 |
| 6M | 90.78 | 0.44 | 0.14 | 0.30 | 0.15 | 0.13 | 97.8 | 7.75 |

TABLE 39

Stability profile of HCP Formulation #11
Description: Drug concentration: 13.42%, pH 8.0, Effect of Niacinamide.

| Duration | % Assay | % Impurity 1 RRT 0.26 | % Impurity 2 RRT 0.79 | % Impurity 3 RRT 0.91 | % Impurity 4 RRT 1.24 | % Hydrocortisone RRT 1.09 | % Peak area | pH of formulation |
|---|---|---|---|---|---|---|---|---|
| Storage condition 25° C. | | | | | | | | |
| Initial | 100.15 | — | — | — | — | 0.0 | 100.0 | 8.11 |
| 3M | 95.69 | — | — | — | — | 0.05 | 99.9 | 8.01 |
| 6M | 93.72 | — | 0.06 | — | — | 0.05 | 99.8 | 7.95 |
| 9M | | | | | | | | |
| 12M | | | | | | | | |
| 18M | | | | | | | | |
| 24M | | | | | | | | |
| Storage condition: 40° C. | | | | | | | | |
| Initial | 100.15 | — | — | — | — | 0.0 | 100.0 | 7.95 |
| 1M | 92.79 | 0.14 | 0.15 | 0.07 | — | 0.15 | 99.4 | 7.95 |
| 2M | 94.22 | 0.33 | 0.20 | 0.13 | 0.19 | 0.16 | 98.8 | 7.77 |
| 3M | 91.85 | 0.76 | 0.33 | 0.14 | 0.40 | 0.16 | 97.5 | 7.88 |
| 6M | 88.89 | 1.09 | 0.38 | 0.32 | 0.69 | 0.16 | 96.2 | 7.78 |

TABLE 40

Stability profile of HCP Formulation #12
Description: Drug concentration: 13.42%, pH 8.0, Effect of 5% HP-8-cyclodextrin.

| Duration | % Assay | % Impurity 1 RRT 0.26 | % Impurity 2 RRT 0.79 | % Impurity 3 RRT 0.91 | % Impurity 4 RRT 1.24 | % Hydrocortisone RRT 1.09 | % Peak area | pH of formulation |
|---|---|---|---|---|---|---|---|---|
| Storage condition: 25° C. | | | | | | | | |
| Initial | 100.99 | — | — | — | — | 0.0 | 100.0 | 8.1 |
| 3M | 98.38 | — | 0.08 | — | — | 0.05 | 99.8 | 8.04 |
| 6M | 94.96 | — | 0.16 | — | 0.04 | 0.05 | 99.5 | 7.92 |
| 9M | | | | | | | | |
| 12M | | | | | | | | |
| 18M | | | | | | | | |
| 24M | | | | | | | | |
| Storage condition: 40° C. | | | | | | | | |
| Initial | 100.99 | — | — | — | — | 0.0 | 100.0 | 8.1 |
| 1M | 91.91 | 0.17 | 0.18 | 0.07 | — | 0.10 | 99.3 | 7.98 |
| 2M | 94.04 | 0.43 | 0.30 | 0.14 | 0.14 | 0.13 | 98.6 | 7.82 |
| 3M | 92.70 | 0.84 | 0.41 | 0.21 | 0.30 | 0.15 | 97.5 | 7.85 |
| 6M | 87.37 | 1.81 | 0.61 | 0.33 | 0.63 | 0.14 | 95.0 | 7.79 |

TABLE 41

Stability profile of HCP Formulation #13
Description: Drug concentration: 13.42%, pH 8.0, Effect of 10% HP-6-cyclodexrin.

| Duration | % Assay | % Impurity 1 RRT 0.26 | % Impurity 2 RRT 0.79 | % Impurity 3 RRT 0.91 | % Impurity 4 RRT 1.24 | % Hydrocortisone RRT 1.09 | % Peak area | pH of formulation |
|---|---|---|---|---|---|---|---|---|
| Storage condition: 25° C. | | | | | | | | |
| Initial | 99.99 | — | — | — | — | 0.0 | 100.0 | 8.01 |
| 3M | 96.97 | — | 0.09 | — | — | 0.05 | 99.8 | 8.00 |
| 6M | 95.41 | 0.08 | 0.15 | — | — | 0.06 | 99.5 | 7.90 |
| 9M | | | | | | | | |
| 12M | | | | | | | | |
| 18M | | | | | | | | |
| 24M | | | | | | | | |
| Storage condition: 40° C. | | | | | | | | |
| Initial | 99.99 | — | — | — | — | 0.0 | 100.0 | 8.01 |
| 1M | 94.62 | 0.15 | 0.19 | 0.08 | — | 0.13 | 99.2 | 8.02 |
| 2M | 94.66 | 0.36 | 0.27 | 0.12 | 0.12 | 0.13 | 98.8 | 7.79 |

TABLE 41-continued

Stability profile of HCP Formulation #13
Description: Drug concentration: 13.42%, pH 8.0, Effect of 10% HP-6-cyclodexrin.

| Duration | % Assay | % Impurity 1 RRT 0.26 | % Impurity 2 RRT 0.79 | % Impurity 3 RRT 0.91 | % Impurity 4 RRT 1.24 | % Hydrocortisone RRT 1.09 | % Peak area | pH of formulation |
|---|---|---|---|---|---|---|---|---|
| 3M | 92.40 | 0.88 | 0.44 | 0.20 | 0.30 | 0.15 | 97.4 | 7.90 |
| 6M | 88.55 | 1.54 | 0.56 | 0.30 | 0.58 | 0.14 | 95.5 | 7.78 |

TABLE 42

Stability profile of HCP Formulaton #14
Description: Drug concentration: 13.42%, pH 8.0, Effect of Lactbionic acid.

| Duration | % Assay | % Impurity 1 RRT 0.26 | % Impurity 2 RRT 0.79 | % Impurity 3 RRT 0.91 | % Impurity 4 RRT 1.24 | % Hydrocortisone RRT 1.09 | % Peak area | pH of formulation |
|---|---|---|---|---|---|---|---|---|
| Storage condition: 25° C. | | | | | | | | |
| Initial | 100.34 | — | — | — | — | 0.0 | 100.0 | 8.04 |
| 3M | 96.09 | — | 0.08 | — | — | 0.05 | 99.8 | 8.00 |
| 6M | 94.21 | 0.10 | 0.15 | — | 0.05 | 0.05 | 99.5 | 7.87 |
| 9M | | | | | | | | |
| 12M | | | | | | | | |
| 18M | | | | | | | | |
| 24M | | | | | | | | |
| Storage condition: 40° C. | | | | | | | | |
| Initial | 100.34 | — | — | — | — | 0.0 | 100.0 | 8.04 |
| 1M | 94.32 | 0.14 | 0.20 | 0.06 | — | 0.10 | 99.4 | 8.02 |
| 2M | 95.79 | 0.40 | 0.28 | 0.11 | 0.12 | 0.13 | 98.8 | 7.81 |
| 3M | 94.63 | 0.82 | 0.40 | 0.17 | 0.29 | 0.13 | 97.7 | 7.88 |
| 6M | 88.85 | 1.67 | 0.54 | 0.30 | 0.62 | 0.13 | 95.4 | 7.79 |

TABLE 43

Stability profile of HCP Formulation #15A
Description: Drug concentration: 13.42%, pH 8.0, unpouched sample.

| Duration | % Assay | % Impurity 1 RRT 0.26 | % Impurity 2 RRT 0.79 | % Impurity 3 RRT 0.91 | % Impurity 4 RRT 1.24 | % Hydrocortisone RRT 1.09 | % Peak area | pH of formulation |
|---|---|---|---|---|---|---|---|---|
| Storage condition: 25° C. | | | | | | | | |
| Initial | 102.24 | — | — | — | — | 0.0 | 100.0 | 7.98 |
| 3M | 95.80 | — | 0.09 | — | — | 0.04 | 99.8 | 7.90 |
| 6M | 94.80 | 0.12 | 0.16 | — | 0.06 | 0.05 | 99.4 | 7.87 |
| 9M | | | | | | | | |
| 12M | | | | | | | | |
| 18M | | | | | | | | |
| 24M | | | | | | | | |
| Storage condition: 40° C. | | | | | | | | |
| Initial | 101.24 | — | — | — | — | 0.0 | 100.0 | 7.98 |
| 1M | 93.50 | 0.34 | 0.26 | 0.11 | 0.08 | 0.13 | 98.8 | 7.94 |
| 2M | 93.67 | 0.98 | 0.44 | 0.22 | 0.33 | 0.15 | 97.4 | 7.90 |
| 3M | 91.42 | 1.11 | 0.46 | 0.23 | 0.40 | 0.15 | 96.9 | 7.81 |
| 6M | 87.07 | 2.06 | 0.58 | 0.38 | 0.72 | 0.16 | 94.7 | 7.79 |

TABLE 44

Stability profile of HCP Formulation #15B
Description: Drug concentration: 13.42%, pH 8.0, pouched with Nitrogen purging.

| Duration | % Assay | % Impurity 1 RRT 0.26 | % Impurity 2 RRT 0.79 | % Impurity 3 RRT 0.91 | % Impurity 4 RRT 1.24 | % Hydrocortisone RRT 1.09 | % Peak area | pH of formulation |
|---|---|---|---|---|---|---|---|---|
| Storage condition: 25° C. | | | | | | | | |
| Initial | 102.24 | — | — | — | — | 0.0 | 100.0 | 7.98 |
| 3M | 96.23 | — | 0.08 | — | — | 0.04 | 99.8 | 7.88 |
| 6M | 95.36 | 0.13 | 0.17 | — | 0.06 | 0.05 | 99.4 | 7.85 |
| 9M | | | | | | | | |
| 12M | | | | | | | | |
| 18M | | | | | | | | |
| 24M | | | | | | | | |
| Storage condition: 40° C. | | | | | | | | |
| Initial | 102.24 | — | — | — | — | 0.0 | 100.0 | 7.98 |
| 1M | 94.57 | 0.21 | 0.20 | 0.05 | 0.03 | 0.11 | 99.2 | 7.93 |
| 2M | 95.28 | 0.83 | 0.41 | 0.18 | 0.28 | 0.13 | 97.7 | 7.94 |
| 3M | 91.77 | 0.89 | 0.44 | 0.21 | 0.34 | 0.15 | 97.4 | 7.83 |
| 6M | 88.69 | 1.88 | 0.54 | 0.35 | 0.65 | 0.16 | 95.1 | 7.84 |

TABLE 45

Stability profile of HCP Formulation #15C
Description: Drug concentration: 13.42%, pH 8.0, pouched with 2 Oxygen scavengers.

| Duration | % Assay | % Impurity 1 RRT 0.26 | % Impurity 2 RRT 0.79 | % Impurity 3 RRT 0.91 | % Impurity 4 RRT 1.24 | % Hydrocortisone RRT 1.09 | % Peak area | pH of formulation |
|---|---|---|---|---|---|---|---|---|
| Storage condition 25° C. | | | | | | | | |
| Initial | 102.24 | — | — | — | — | 0.0 | 100.0 | 7.98 |
| 3M | 93.75 | — | 0.07 | — | — | 0.05 | 99.9 | 7.85 |
| 6M | 94.81 | 0.07 | .012 | — | — | 0.07 | 99.6 | 7.75 |
| 9M | | | | | | | | |
| 12M | | | | | | | | |
| 18M | | | | | | | | |
| 24M | | | | | | | | |
| Storage condition 40° C. | | | | | | | | |
| Initial | 102.24 | — | — | — | — | 0.0 | 100.0 | 7.98 |
| 1M | 94.04 | 0.20 | 0.20 | 0.07 | 0.02 | 0.12 | 99.2 | 7.98 |
| 2M | 94.34 | 0.58 | 0.27 | 0.19 | 0.21 | 0.24 | 98.2 | 7.96 |
| 3M | 92.25 | 0.57 | 0.27 | 0.21 | 0.26 | 0.27 | 98.2 | 7.82 |
| 6M | 90.92 | 1.02 | 0.24 | 0.37 | 0.66 | 0.39 | 96.7 | 7.81 |

TABLE 46

Summary of all HCP formulations after 6M of storage at 25° C. and 40° C.

| Form. # | pH | Drug conc. | Antioxidant or solublizing agent | Packing type | % Assay value of HCP 25° C. | % Assay value of HCP 40° C. |
|---|---|---|---|---|---|---|
| 1 | 7.0 | 13.42 | None | — | 95.30 | 80.32 |
| 2 | 7.5 | 13.42 | None | — | 95.80 | 86.72 |
| 3 | 8.0 | 13.42 | None | — | 95.84 | 85.66 |
| 4 | 8.5 | 13.42 | None | — | 95.36 | 88.67 |
| 5 | 8.0 | 6.71 | None | — | 92.41 | 79.67 |
| 6 | 8.0 | 13.42 | Sodium Sulfite | — | 99.59 | 95.26 |
| 7 | 8.0 | 13.42 | Monothioglycerol | — | 99.58 | 97.99 |
| 8A | 8.0 | 13.42 | Ascorbic acid | Unpouched | 99.40 | 95.40 |
| 8B | 8.0 | 13.42 | Ascorbic acid | N₂ purging | 98.25 | 98.84 |
| 8C | 8.0 | 13.42 | Ascorbic acid | O₂ scavenger | 100.06 | 97.27 |
| 9 | 8.0 | 13.42 | Methionine | — | 98.37 | 95.08 |
| 10 | 8.0 | 13.42 | Creatinine | — | 93.95 | 90.78 |
| 11 | 8.0 | 13.42 | Niacinamide | — | 93.72 | 88.89 |
| 12 | 8.0 | 13.42 | 5% HP-β-CD | — | 94.96 | 87.37 |
| 13 | 8.0 | 13.42 | 10% HP-β-CD | — | 95.41 | 88.55 |
| 14 | 8.0 | 13.42 | Lactobionic acid | — | 94.21 | 88.85 |
| 15A | 8.0 | 13.42 | None | Unpouched | 94.80 | 87.07 |
| 15B | 8.0 | 13.42 | None | N₂ purging | 95.35 | 86.69 |
| 15C | 8.0 | 13.42 | None | O₂ scavenger | 94.81 | 90.92 |

Without wishing to be bound by any particular theory, and after stability analysis of all HCP formulations for 6 months of storage at 25° C. and 40° C., HCP F #7 seems to be the most stable formulation. It contains 0.5% w/v Monothioglycerol as an antioxidant. Monothioglycerol is a liquid excipient.

Example 2: Exemplary Hydrocortisone Injection Formulation

| Ingredients | Function | Composition per 1 mL | Composition per unit dose, 2 mL | FDA inactive ingredient database limit |
|---|---|---|---|---|
| Hydrocortisone sodium phosphate | Active ingredient | 67.1 mg (50 mg hydrocortisone) | 134.2 mg (100 mg hydrocortisone) | — |
| Monobasic sodium phosphate anhydrous | Buffer agent | 1.0 mg | 2.0 mg | 1.2% w/v, IM |
| Dibasic sodium phosphate anhydrous | Buffer agent | 10.9 mg | 21.8 mg | 1.75% w/v, IM |
| Disodium edetate | Chelating agent | 0.2 mg | 0.4 mg | 10% w/v, IM |
| Monothioglycerol | Antioxidant | 5.0 mg | 10.0 mg | 0.5% w/v, IM |
| Sodium hydroxide/HCl | pH adjustor | Q.S. pH (appr 8.0) | Q.S pH (appr 8.0) | — |
| Water | Solvent | Q.S. to 1 mL | Q.S. to 1 mL | — |

Example 3: Stability Data for Example Formulations to Evaluate Alternative Antioxidants

| | Total Impurities (% area), 40° C. | | | | |
|---|---|---|---|---|---|
| Time (mon) | F#3, EDTA/Rongalite | F#6, EDTA/sulfite | F#7, EDTA/MTG | F#8, EDTA/ascorbic acid | F#9, EDTA/methionine |
| 0 | 0.00% | 0.09% | 0.00% | 0.00% | 0.00% |
| 1 | 0.97% | 0.53% | 0.35% | 0.42% | 0.50% |
| 2 | 2.14% | 0.77% | 0.74% | 0.52% | 0.98% |
| 3 | 3.05% | 1.07% | 1.13% | 0.93% | 1.31% |
| 6 | 5.72% | 1.80% | 1.78% | 2.08% | 2.42% |

Figure 4:
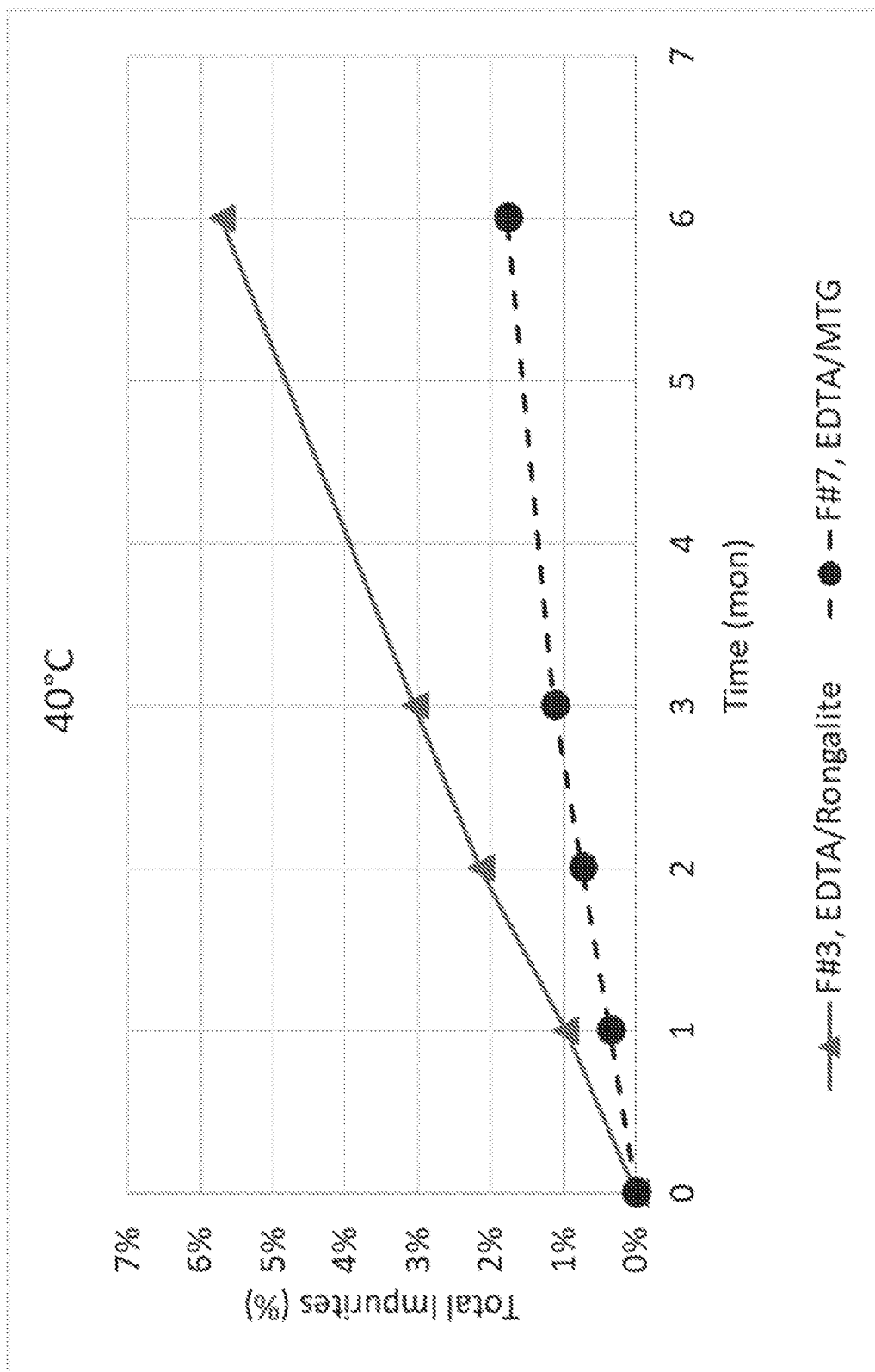
FIG. 4 illustrates the stability of two formulations (#3 and #7) over 6 months.
Figure 5:
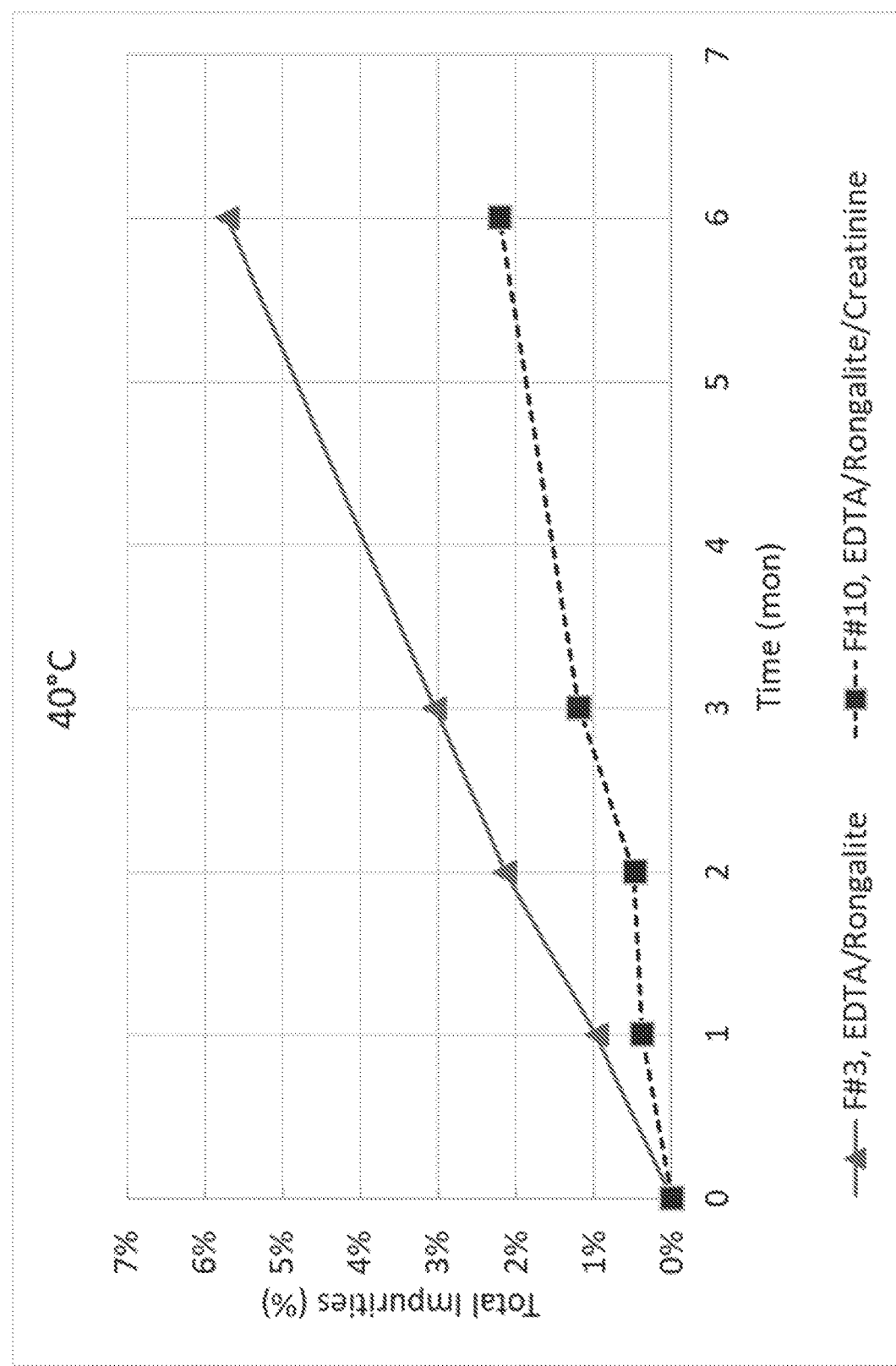
FIG. 5 illustrates the stability of two formulations (#3 and #10) over 6 months.
Figure 6:
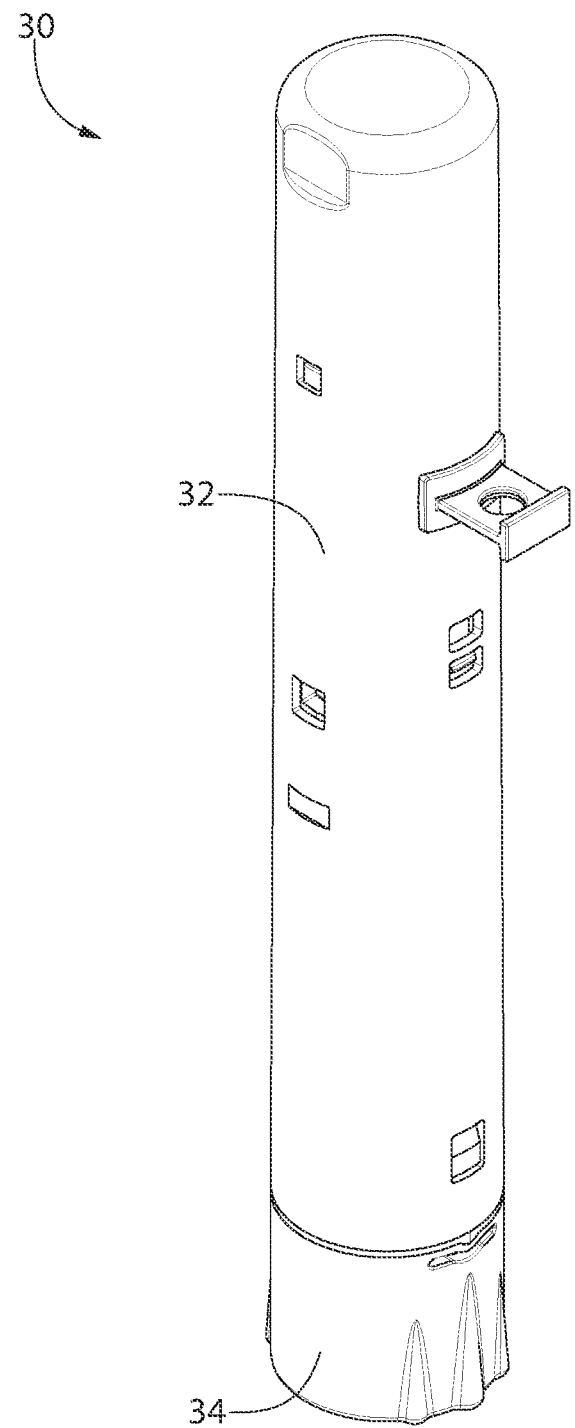
FIG. 6 is a perspective view of an injector in accordance with an exemplary embodiment of the present invention.
Figure 7:
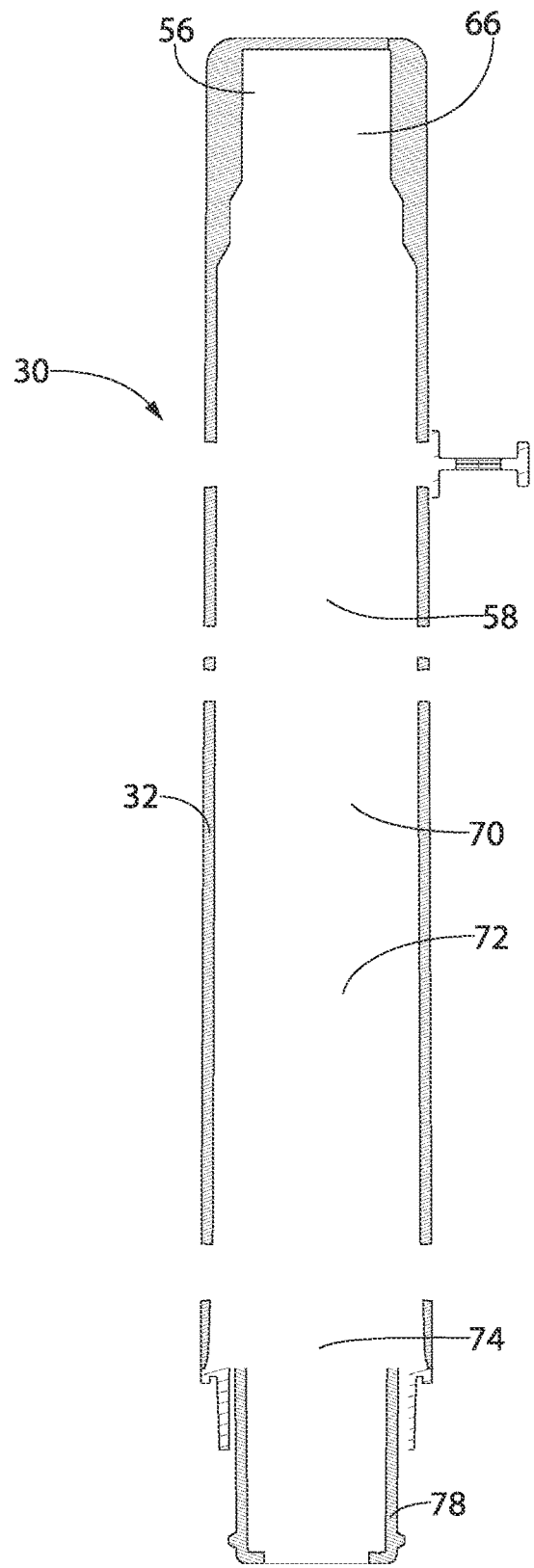
FIG. 7 is a sectional view of the injector of FIG. 6.

Also as shown in FIG. 4 which illustrates the stability of two formulations (#3 and #7) over 6 months.

| | Total Impurities (% area), 25° C. | | | | |
|---|---|---|---|---|---|
| Time (mon) | F#3, EDTA/Rongalite | F#6, EDTA/sulfite | F#7, EDTA/MTG | F#8, EDTA/ascorbic acid | F#9, EDTA/methionine |
| 0 | 0.00% | 0.09% | 0.00% | 0.00% | 0.00% |
| 3 | 0.20% | 0.04% | 0.06% | 0.15% | 0.31% |
| 6 | 0.61% | 0.21% | 0.12% | 0.17% | 0.42% |

Stability Data for Example Formulations to the third additive, Creatinine

| | Total Impurities (% area), 40° C. | |
|---|---|---|
| Time (mon) | F#3, EDTA/Rongalite | F#10, EDTA/Rongalite/Creatinine |
| 0 | 0.00% | 0.00% |
| 1 | 0.97% | 0.38% |
| 2 | 2.14% | 0.48% |
| 3 | 3.05% | 1.20% |
| 6 | 5.72% | 2.22% |

| | Total Impurities (% area), 25° C. | |
|---|---|---|
| Time (mon) | F#3, EDTA/Rongalite | F#10, EDTA/Rongalite/Creatinine |
| 0 | 0.00% | 0.00% |
| 3 | 0.20% | 0.09% |
| 6 | 0.61% | 0.12% |

Example 4: Formulation Concentrations

| Formulation: Component | Equivalent to: 50 mg/ml hydrocortisone | | Equivalent to: 100 mg/ml hydrocortisone | | Equivalent to: 100 mg/ml hydrocortisone | | Equivalent to: 100 mg/ml hydrocortisone | |
|---|---|---|---|---|---|---|---|---|
| Hydrocortisone sodium phosphate | 67.1 mg | 6.71% | 134.2 mg | 13.42% | 6710.0 mg | 13.42% | 2,013.0 g | 13.42% |

-continued

| Formulation: Component | Equivalent to: 50 mg/ml hydrocortisone | | Equivalent to: 100 mg/ml hydrocortisone | | Equivalent to: 100 mg/ml hydrocortisone | | Equivalent to: 100 mg/ml hydrocortisone | |
|---|---|---|---|---|---|---|---|---|
| Monobasic sodium phosphate | 1.0 mg | 0.10% | 1.0 mg | 0.10% | 50.0 mg | 0.10% | 19.5 g [1] | 0.13% [1] |
| Dibasic sodium phosphate | 10.9 mg | 1.09% | 10.9 mg | 1.09% | 545.0 mg | 1.09% | 205.5 g [2] | 1.37% [2] |
| Disodium EDTA | 0.2 mg | 0.02% | 0.2 mg | 0.02% | 10.0 mg | 0.02% | 3.0 g | 0.02% |
| Monothioglycerol | 5.0 mg | 0.50% | 5.0 mg | 0.50% | 250.0 mg | 0.50% | 75.0 g | 0.50% |
| Sodium hydroxide | | | | | | | | |
| Water (Q. S.) | 1 mL | | 1 mL | | 50 mL | | 15,900.0 g [3] | |

[1] Monobasic sodium phosphate dihydrate
[2] Dibasic sodium phosphate dihydrate
[3] Equivalent to 15 Liter

Example 5: Stability Data

| Analysis | Release (Time zero) limits | Stability acceptance limits | Time (months) 0 | Time (months) 3 | Time (months) 6 |
|---|---|---|---|---|---|
| Appearance & pH | | | | | |
| Appearance of Solution | Clear colorless to yellowish solution in a 2.25 mL glass syringe with grey stopper | Clear colorless to yellowish solution in a 2.25 mL glass syringe with grey stopper | Clear colorless to yellowish solution in a 2.25 mL glass syringe with grey stopper | Clear colorless to yellowish solution in a 2.25 mL glass syringe with grey stopper | Clear colorless to yellowish solution in a 2.25 mL glass syringe with grey stopper |
| pH | 7.5-8.5 | 7.5-8.5 | 8.0 | 8.0 | 8.0 |
| Assay & Impurities | | | | | |
| Assay of Hydrocortisone Sodium Phosphate | 127.5-140.9 (mg/mL) | 120.8-147.6 (mg/mL) | 137.2 | 139.0 | 136.6 |
| Assay of Hydrocortisone Equivalent | 95-105% of label claim | 90-110% of label claim | 102.2 | 103.6 | 101.8 |
| Specified Impurity, % | | | | | |
| Hydrocortisone | ≤0.5% | ≤2.0% | <0.05% | <0.05% | 0.05% |
| RRT 0.91 | ≤0.1% | ≤0.5% | <0.05% | <0.05% | <0.05% |
| Single Unspecified Impurity, % | | | | | |
| RRT 0.23 | ≤0.1% | ≤0.2% | — | 0.05% | 0.07% |
| RRT 1.03 | ≤0.1% | ≤0.2% | 0.05% | <0.05% | <0.05% |
| RRT 1.16 | ≤0.1% | ≤0.2% | — | — | 0.05% |
| Sum of Impurities, % | ≤1.0% | ≤3.0% | 0.05% | 0.05% | 0.16% |
| Sub-Visible Particles | | | | | |
| >10 μm | ≤6000 part. Per container | ≤6000 part. Per container | 433 | 95 | 200 |
| >25 μm | ≤600 part. Per container | ≤600 part. Per container | 4 | 1 | 2 |
| Uniformity of dosage | | | | | |
| Volume in container | 1.0-1.2 mL Individual delivered volume (mL): To be reported | 1.0-1.2 mL Individual delivered volume (mL): To be reported | Complies, 1.) 1.5 2.) 1.05 3.) 1.05 4.) 1.05 5.) 1.05 | Complies, 1.) 1.06 2.) 1.06 3.) 1.05 4.) 1.07 5.) 1.06 | To be added |
| Uniformity of dosage units | Acceptance value (AV) for 10 dosage units ≤15.0, if AV > 15.0, test the next 20 dosage units, AV for 30 dosage units ≤15.0, No individual content of any dosage unit is less than [0.75M] or more than [1.25M], Average volume: To be reported. | Acceptance value (AV) for 10 dosage units ≤15.0, if AV > 15.0, test the next 20 dosage units, AV for 30 dosage units ≤15.0, No individual content of any dosage unit is less than [0.75M] or more than [1.25M], Average volume: To be reported. | Complies after first step, Acceptance value = 2.0, Average Volume = 1.05 mL | Complies after first step, Acceptance value = 3.1, Average Volume = 1.05 mL | To be added |

| Analysis | Release (Time zero) limits | Stability acceptance limits | Time (months) 0 | Time (months) 3 | Time (months) 6 |
|---|---|---|---|---|---|
| | | Microbiological tests | | | |
| Sterility | Sterile | Sterile | Sterile | Not tested | Not tested |
| Bacterial Endotoxins | ≤1.25 EU/mg hydrocortisone | ≤1.25 EU/mg hydrocortisone | ≤1.25 EU/mg hydrocortisone | Not tested | Not tested |

Example 6

One unknown impurity peak (RRT 0.91) in hydrocortisone phosphate product was purified via preparative HPLC and characterized by LCMS, HPLC and NMR. Its structure was tentatively. proposed as phosphate migration isomer of hydrocortisone phosphate.

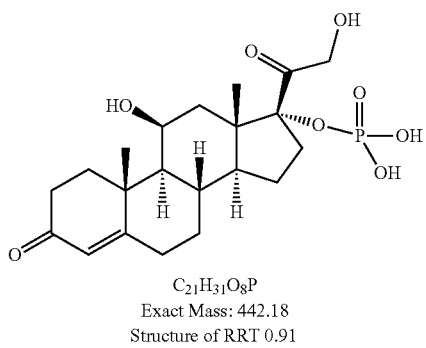

$C_{21}H_{31}O_8P$
Exact Mass: 442.18
Structure of RRT 0.91

While certain embodiments of the present invention have been described and/or exemplified above, various other embodiments will be apparent to those skilled in the art from the foregoing disclosure. The present invention is, therefore, not limited to the particular embodiments described and/or exemplified, but is capable of considerable variation and modification without departure from the scope and spirit of the appended claims.

The invention claimed is:

1. An aqueous pharmaceutical formulation comprising from 130 to 140 mg/mL hydrocortisone sodium phosphate, from 4.5 to 12.5 mg/mL monothioglycerol, from 0.5 to 2.5 mg/mL monobasic sodium phosphate, from 5 to 25 mg/mL dibasic sodium phosphate, from 0.1 to 1 mg/mL disodium EDTA, and water, and having a pH of 7.5 to 8.5, wherein the aqueous pharmaceutical formulation is stored in glass against at least one non-glass pharmaceutically acceptable surface selected from a stopper surface, a needle surface, a needle tip cap surface, a needle shield surface, a septa surface, a syringe plunger surface, a plastic syringe surface, an injector surface, or a rubber surface, and comprises:
 no more than 0.06% soluble impurities upon storage at 25° C. for about 3 months; or
 no more than 0.35% soluble impurities upon storage at 40° C. for about 1 month.

2. The aqueous pharmaceutical formulation of claim 1, comprising from 130 to 135 mg/mL hydrocortisone sodium phosphate.

3. The aqueous pharmaceutical formulation of claim 1, comprising 130 mg/mL hydrocortisone sodium phosphate, 135 mg/mL hydrocortisone sodium phosphate, or 140 mg/mL hydrocortisone sodium phosphate.

4. The aqueous pharmaceutical formulation of claim 1, comprising 130 mg/mL hydrocortisone sodium phosphate, 131 mg/mL hydrocortisone sodium phosphate, 132 mg/mL hydrocortisone sodium phosphate, 133 mg/mL hydrocortisone sodium phosphate, 134 mg/mL hydrocortisone sodium phosphate, about 135 mg/mL hydrocortisone sodium phosphate, 136 mg/mL hydrocortisone sodium phosphate, 137 mg/mL hydrocortisone sodium phosphate, 138 mg/mL hydrocortisone sodium phosphate, 139 mg/mL hydrocortisone sodium phosphate, or 140 mg/mL hydrocortisone sodium phosphate.

5. The aqueous pharmaceutical formulation of claim 1, comprising 134 mg/mL hydrocortisone sodium phosphate, 134.1 mg/mL hydrocortisone sodium phosphate, 134.2 mg/mL hydrocortisone sodium phosphate, 134.3 mg/mL hydrocortisone sodium phosphate, 134.4 mg/mL hydrocortisone sodium phosphate, 134.5 mg/mL hydrocortisone sodium phosphate, 134.6 mg/mL hydrocortisone sodium phosphate, 134.7 mg/mL hydrocortisone sodium phosphate, 134.8 mg/mL hydrocortisone sodium phosphate, 134.9 mg/mL hydrocortisone sodium phosphate, or 135 mg/mL hydrocortisone sodium phosphate.

6. The aqueous pharmaceutical formulation of claim 1, comprising from 4.5 to 5.5 mg/mL monothioglycerol.

7. The aqueous pharmaceutical formulation of claim 1, comprising 4.5 mg/mL monothioglycerol, 4.6 mg/mL monothioglycerol, 4.7 mg/mL monothioglycerol, 4.8 mg/mL monothioglycerol, 4.9 mg/mL monothioglycerol, 5 mg/mL monothioglycerol, 5.1 mg/mL monothioglycerol, 5.2 mg/mL monothioglycerol, 5.3 mg/mL monothioglycerol, 5.4 mg/mL monothioglycerol, or 5.5 mg/mL monothioglycerol.

8. The aqueous pharmaceutical formulation of claim 1, wherein the pharmaceutical formulation has a pH of 7.5, 7.6, 7.7, 7.8, 7.9, 8, 8.1, 8.2, 8.3, 8.4, or 8.5.

9. The aqueous pharmaceutical formulation of claim 1, wherein the aqueous pharmaceutical formulation comprises no more than 0.05% soluble impurities upon formulation.

10. The aqueous pharmaceutical formulation of claim 1, wherein the aqueous pharmaceutical formulation comprises less than 0.06% soluble impurities upon storage at 25° C. for about 3 months.

11. The aqueous pharmaceutical formulation of claim 1, wherein the formulation comprises no more than 0.12% soluble impurities upon storage at 25° C. for about 6 months.

12. The aqueous pharmaceutical formulation of claim 1, wherein upon storage at 25° C. for about 6 months, the formulation comprises less than 0.12% soluble impurities.

13. The aqueous pharmaceutical formulation of claim 1, wherein upon storage at 40° C. for about 3 months, the aqueous pharmaceutical formulation comprises no more than 1.13% soluble impurities.

14. A prefilled glass syringe comprising an aqueous pharmaceutical formulation comprising from 130 to 140 mg/mL hydrocortisone sodium phosphate, from 4.5 to 12.5 mg/mL monothioglycerol, from 0.5 to 2.5 mg/mL monobasic sodium phosphate, from 5 to 25 mg/mL dibasic sodium phosphate, from 0.1 to 1 mg/mL disodium EDTA, and water, and having a pH of 7.5 to 8.5, wherein the aqueous pharmaceutical formulation is stored against at least one non-glass pharmaceutically acceptable surface selected from a rubber syringe plunger surface, a metal needle surface, and a plastic needle shield surface, and comprises:
  no more than 0.06% soluble impurities upon storage at 25° C. for about 3 months; or
  no more than 0.35% soluble impurities upon storage at 40° C. for about 1 month.

* * * * *